(12) United States Patent
Dawson et al.

(10) Patent No.: US 12,276,657 B2
(45) Date of Patent: Apr. 15, 2025

(54) DETECTION OF PAR IN THE CSF OF PATIENTS WITH PARKINSON'S DISEASE

(71) Applicant: The Johns Hopkins University, Baltimore, MD (US)

(72) Inventors: Ted Dawson, Baltimore, MD (US); Valina Dawson, Baltimore, MD (US); Tae-In Kam, Baltimore, MD (US); Liana Rosenthal, Lutherville, MD (US); Shaida Andrabi, Birmingham, AL (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/049,773

(22) Filed: Oct. 26, 2022

(65) Prior Publication Data

US 2023/0176041 A1    Jun. 8, 2023

Related U.S. Application Data

(62) Division of application No. 16/616,748, filed as application No. PCT/US2018/035614 on Jun. 1, 2018, now abandoned.

(60) Provisional application No. 62/679,161, filed on Jun. 1, 2018, provisional application No. 62/514,316, filed on Jun. 2, 2017.

(51) Int. Cl.
    *G01N 33/53*    (2006.01)

(52) U.S. Cl.
    CPC ..  *G01N 33/5308* (2013.01); *G01N 2800/2835* (2013.01); *G01N 2800/52* (2013.01)

(58) Field of Classification Search
    CPC ............... C07K 16/44; C07K 2317/21; G01N 2333/91142; G01N 2500/20; G01N 2800/2835; G01N 2800/52; G01N 33/5308; G01N 33/6896
    See application file for complete search history.

(56) References Cited

U.S. PATENT DOCUMENTS

| | | |
|---|---|---|
| 2007/0292883 A1 | 12/2007 | Ossovskaya et al. |
| 2012/0122765 A1 | 5/2012 | Dawson et al. |
| 2013/0022982 A1 | 1/2013 | Wang et al. |
| 2017/0000836 A1 | 1/2017 | Shraibom et al. |
| 2022/0291240 A1* | 9/2022 | Dawson ................ A61P 25/00 |

FOREIGN PATENT DOCUMENTS

WO    WO 2009152607 A1    12/2009

OTHER PUBLICATIONS

Birchler et al., "A quantitative method for determining in vivo activation of PARP and biological activity of inhibitors of the enzyme," Society for Neuroscience Abstracts, 2000, vol. 26, pp. 1-2, Abstract No. 88.1.*
Wang et al., "Phosphorylated α-synuclein in Parkinson's disease," Sci. Transl. Med., 2012, vol. 4, issue 121, pp. 1-8.*
International Search Report for International Application No. PCT/US2018/035614, mailed Oct. 29, 2018, 4 pages.
Written Opinion of the International Searching Authority for International Application No. PCT/US2018/035614, mailed Oct. 29, 2018, 6 pages.
Sarnaik, et al. Influence of PARP-1 polymorphisms in patients after traumatic brain injury. J. Neurotrauma, Mar. 2010, vol. 27, No. 3, pp. 465-471.
Ida, et al. An enzyme-linked immunosorbent assay-based system for determining the physiological level of poly(ADP-ribose) in cultured cells. Anal Biochem. Feb. 1, 2016, vol. 494, pp. 76-81.
Mandir, et al. Poly(ADP-ribose) polymerase activation mediates 1-methyl-4-phenyl-1,2,3,6-tetrahydropyridine (MPTP)-induced parkinsonism. Proc. Natl. Acad. Sci. USA. May 1999. vol. 96, pp. 5774-5779.
Lee, et al. Parthanatos Mediates AIMP2 Activated Age Dependent Dopaminergic Neuronal Loss. Nat. Neurosci. Oct. 2013. vol. 16, Issue 10, pp. 1392-1400, including Corrigenda.
Lee, et al. Poly (ADP-ribose) in the pathogenesis of Parkinson's disease. BMB Reports. 2014. vol. 47, Issue 8, pp. 424-432.
EPO Extended European Search Report for EP Application 18810546.4, dated Jan. 29, 2021, 6 pages.
Jeelani et al., "Theranostics: a treasured tailor for tomorrow", J. Pharm. Bioallied Sci., 2014, 6(Supp 1): S6-S8.
Jimenez-Jimenez et al., "Cerebrospinal fluid biochemical studies in patients with Parkinson's disease: toward a potential search for biomarkers for this disease", Front. Cell Neruoscie., 2014, 8(369): 1-31.
Kam et al., "Poly(ADP-ribose) drives pathologic α-synuclein neurodegeneration in Parkinson's disease", Science, Nov. 2018, 362(6414):eaat8407, pp. 1-10.
Knappik et al., Fully synthetic human combinatorial antibody libraries (HuCAL) based on modular consensus frameworks and CDRs randomized with trinucleotides., J Mol Biol., (2000), pp. 57-86, vol. 296.
Prassler et al. HuCAL Platnium, a synthetic Fab library optimized for sequence diversity and superior performance in mammalian expression systems., J Mol Biol., (2011), pp. 261-278, vol. 413.
Kozbor et al. A human hybrid myeloma for production of human monoclonal antibodies., J Immunology., (1984), pp. 3001-3005, vol. 133.
Hughes et al. A new clinical scale for the staging of dementia., Br J Physchiatry., (1982), pp. 566-572, vol. 140.

* cited by examiner (Continued)

Primary Examiner — Galina M. Yakovleva
(74) Attorney, Agent, or Firm — DLA Piper LLP (US)

(57) ABSTRACT

Poly(ADP-ribose) (PAR) is a protein implicated in numerous neurodegenerative disease states including Parkinson's disease (PD). To date, no routine laboratory test has been developed to diagnosis, assess or monitor patients suffering from PD. Disclosed herein a novel method to assess the PAR concentration in the cerebral spinal fluid (CSF) of a patient and correlate that concentration to the medical condition of a patient with PD. Also disclosed is the use of PAR as a biomarker for PD.

10 Claims, 97 Drawing Sheets

DETECTION OF PAR IN THE CSF OF PATIENTS WITH PARKINSON'S DISEASE

This application claims priority to U.S. Provisional Application 62/514,316 filed on Jun. 2, 2017 and U.S. Provisional Application 62/679,161 filed on Jun. 1, 2018, both of which are incorporated by reference in their entirety for all purposes.

STATEMENT REGARDING FEDERALLY SPONSORED RESEARCH & DEVELOPMENT

This invention was made with government support under grant no. NS38377 and U01NS082133 awarded by the National Institutes of Health. The government has certain rights in the invention.

BACKGROUND OF THE INVENTION

Poly(ADP-ribose) ("PAR") polymerase-1 ("PARP-1") is an important nuclear enzyme that responds to DNA damage and is required for DNA repair. Upon activation, PARP-1 catalyzes the transfer of ADP-ribose from nicotinamide adenine dinucleotide ("NAD+") and conjugates PAR onto a variety of nuclear proteins such as histones, DNA polymerases, topoisomerases, and transcription factors as well as auto-modification of PARP-1 itself, thus regulating a variety of physiologic processes. Excessive activation of PARP-1 leads to an intrinsic cell death program, which has been designated parthanatos (or, alternatively, PARP-1-dependent cell death) to distinguish it from necrosis and apoptosis. Parthanatos is known to occur in many diseases and conditions such as stroke, Parkinson's disease, heart attack, diabetes, and ischemia reperfusion injury. PARP-1 inhibition or PARP-1 gene deletion is markedly protective in models of many cell injury paradigms, including stroke, trauma, ischemia-reperfusion injury, diabetes, and neurodegenerative diseases, indicating that parthanatos plays a prominent role in these disorders.

The mitochondrial protein apoptosis-inducing factor ("AIF") plays a pivotal role in parthanatos, during which AIF is released from the mitochondria and translocates to the nucleus. AIF is a mitochondrial oxidoreductase that, like cytochrome C, has two independent functions. The first is within mitochondria, involving cell survival, thought to be through assembly or stabilization of respiratory complex I. The second is as a promoter of parthanatos cell death. AIF is released into the cytoplasm following PARP-1 activation, ultimately entering the nucleus to induce cell death.

Parkinson's disease (PD) is an age-related neurodegenerative disease in which α-syn deposits as fibrils in intracytoplasmic inclusions in structures termed Lewy bodies and neurites. Recombinant α-syn can be aggregated in vitro to form fibrils similar in structure to those found in vivo, and these α-syn pre-formed fibrils (α-syn PFF) can spread in a prion-like manner: both in in vitro neuronal cultures and in vivo when injected into the mouse brain with accompanying phosphorylation of α-syn on serine 129, a marker of pathologic α-syn and neurotoxicity. While it is clear that aggregated α-syn underlies the pathology of PD, what drives abnormal aggregation of α-syn as well as the cell injury and death mechanisms that are activated by this aggregation are not yet known. Since poly (ADP-ribose) (PAR) polymerase-1 (PARP-1) and PAR play a major contributing role in cell death relevant to neurologic disorders, here the role for PARP-1 and PAR in pathologic α-syn induced neurodegeneration was evaluated.

Additionally, PD is a slowly progressive, neurodegenerative CNS disorder characterized by slow and decreased movement, muscular rigidity, resting tremor, postural instability, cognitive impairment and dementia. The major pathological feature of PD is selective degeneration of dopaminergic neurons in the substantia nigra pars compacta (SNpc) and loss of their terminals in the caudate and putamen. Loss of substantia nigra neurons, which project into the caudate nucleus and putamen, depletes dopamine in these areas. Evidence suggests that multiple factors, including genetic and environmental ones, contribute to the dopaminergic neurodegeneration in this neurodegenerative disease.

The medical treatment of PD is directed to stopping, slowing or reducing the extent of or minimizing the neurodegenerative process in nigrostriatal neurons (neuroprotective therapy) and eliminating the biochemical imbalance (symptomatic therapy). The main directions of symptomatic therapy in PD are to increase dopamine synthesis, or stimulate dopamine receptors activity and dopamine release from the presynaptic space, and to inhibit dopamine reuptake by presynaptic receptors and dopamine catabolism.

Because there is no known cure for PD at this time and different patients respond to treatment methods differently, it is important for a medical professional to carefully monitor disease progression in a patient. This allows the medical professional to adjust or alter the medical treatment the patient receives in the event that the current treatment is ineffective. The current method for monitoring PD progress is a subjective scale based on the level of disability and impairment experienced by a patient.

Thus there remains a need to more specifically to assess and monitor the treatment and progression of PD patients in order fine tune medical treatment. A need also exists for a quantitative as well as qualitative scale that eliminates or reduces the subjective component of the assessment.

BRIEF DESCRIPTION OF THE INVENTION

In a first aspect, disclosed herein is a method for determining a poly(ADP-ribose) (PAR) concentration in cerebral spinal fluid, the method comprising collecting a sample of cerebrospinal fluid (CSF) from a patient, performing a PAR-sandwich ELISA on the CSF sample, thereby determining the PAR concentration in the CSF.

In a second aspect, disclosed herein is a method for determining the therapeutic efficacy of a medical treatment for Parkinson's disease, the method comprising collecting a sample of cerebrospinal fluid (CSF) from a patient, measuring a poly(ADP-ribose) (PAR) concentration in the CSF sample, and comparing the PAR concentration in the patient to a PAR concentration in at least one control sample.

In yet another aspect, disclosed herein is a method for monitoring the disease progression of a patient with Parkinson's disease (PD), the method comprising collecting a sample of cerebrospinal fluid (CSF) from a patient, measuring a poly(ADP-ribose) (PAR) concentration in the CSF sample, and comparing the PAR concentration in the patient to a PAR concentration in at least one control sample, wherein the patient is receiving at least one medical treatment for PD.

In still yet another aspect, disclosed herein is a method of diagnosing a patient with Parkinson's disease, the method comprising collecting a sample of cerebrospinal fluid (CSF) from a patient, measuring a poly(ADP-ribose) (PAR) concentration in the CSF sample, and comparing the PAR concentration in the patient to a PAR concentration in at least one control sample.

In still yet another aspect, disclosed herein is a theranostic method for Parkinson's disease, the method comprising collecting a sample of cerebrospinal fluid (CSF) from a patient who is receiving at least one medical treatment for PD, measuring a poly(ADP-ribose) (PAR) concentration in the CSF sample, comparing the PAR concentration in the patient to a PAR concentration in at least one control sample.

In still yet another aspect, disclosed herein is the use of PAR in the CSF of a patient as a biomarker for PD.

DETAILED DESCRIPTION OF THE INVENTION

Figure 1:
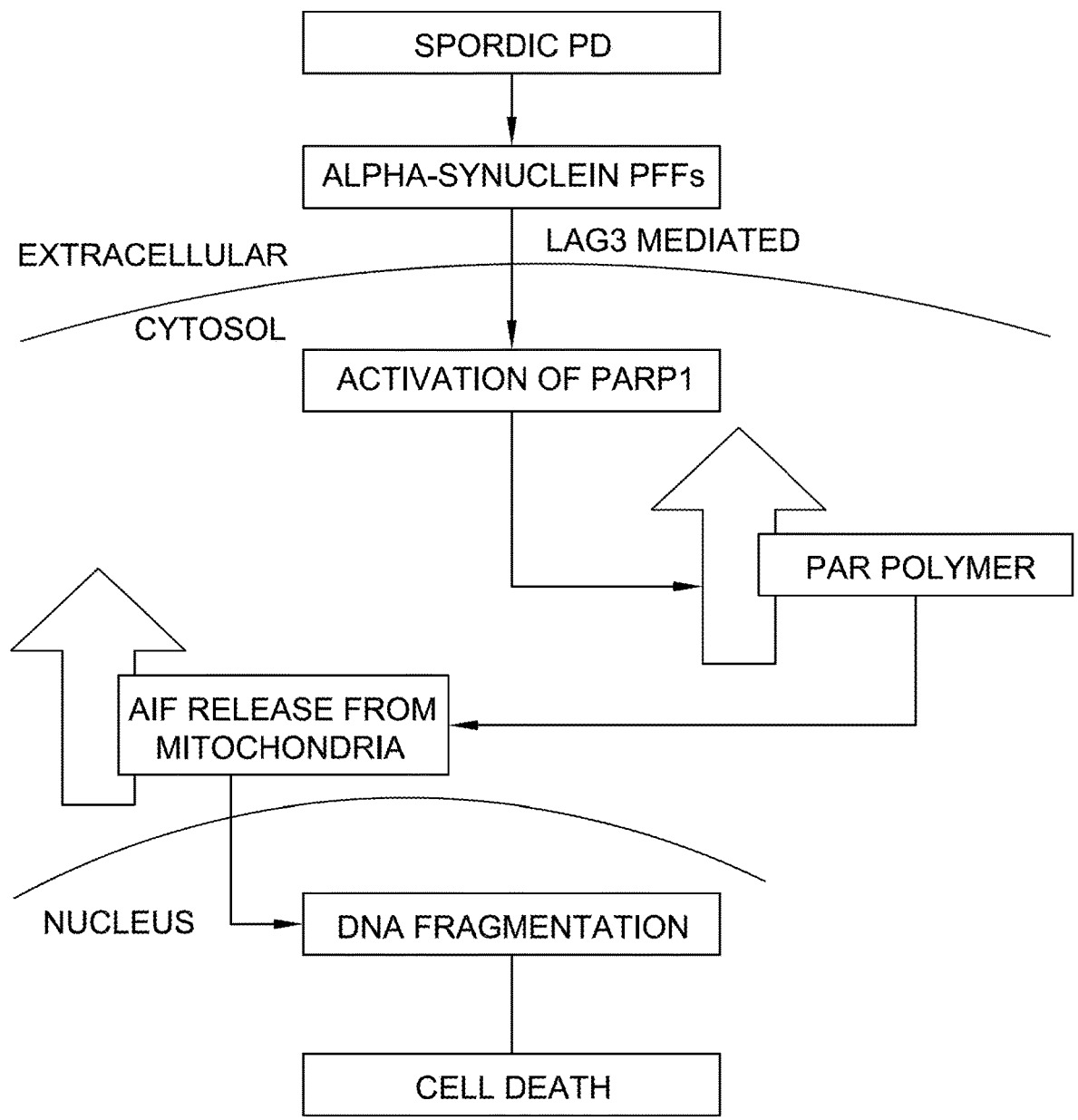
FIG. 1 is a schematic drawing of the processes in a cell illustrating the model of PAR-dependent AIF release in parthanatos.

Previously, it was discovered that a novel and useful mechanism for preventing cell death following activation of PARP-1 by administering agents that interfere with the PAR-AIF interaction (see US 20120122765 which is incorporated by reference in its entirety). Such mechanisms are useful in treating patients suffering from Parkinson's disease. In this regard, the identification of AIF as a PAR polymer-binding protein establishes that therapeutic compounds which inhibit the interaction of PAR polymer with AIF may be useful in mono or combination therapies as protective compounds against stressors which activate PARP-1.

In continuing this work, disclosed herein is a novel method for monitoring and assessing patients suffering from PD. Also disclosed is a novel method for monitoring and assessing the effectiveness of medical treatment administered to a patient suffering from PD. The theranostic methods disclosed herein enable a medical professional to better develop a treatment plan for a patient suffering from PD that has the best opportunity to slow or arrest the progression of the disease.

In one aspect, disclosed herein is a method for determining the poly(ADP-ribose) (PAR) concentration in cerebral spinal fluid, the method comprising: collecting a sample of cerebrospinal fluid (CSF) from a patient, performing a PAR-sandwich ELISA on the CSF sample, thereby determining the PAR concentration in the CSF.

In some embodiments, the method further comprises comparing the PAR concentration in the CSF sample to the PAR concentration in at least one control sample. The control sample can be a previously collected CSF sample from the same patient or from a different patient. In some aspects, more than one control sample is used. Each control sample can be from the same patient or a different patient selected independently from every other control sample.

In some aspects, the control sample is a prepared standard with a known concentration of PAR such that it would enable a comparison of the tested sample to the control sample, thereby allowing a determination of the PAR concentration in the tested sample. Prepared control standards, such as those shown in FIG. 2, may be used thereby allowing for a comparison of the tested sample to a generated control curve thus enabling quantification of the PAR concentration in the tested sample.

A description of the sandwich-ELISA is provided elsewhere herein. In some aspects, the capture antibody, the detection antibody, or both are anti-PAR antibodies. They may be monoclonal or polyclonal, and they may or may not be humanized. In some aspects, the antibody is an anti-PAR antibody prepared from a human combinatorial antibody library.

In some aspects the human combinatorial library is the HuCAL® Technology from Bio-RAD®. For examples of the HuCAL® Technology, see Knappik, A. et al., (2000). "Fully synthetic human combinatorial antibody libraries (HuCAL) based on modular consensus frameworks and CDRs randomized with trinucleotides," *J Mol Biol.*, 296: 57-86, and Prassler, J. et al., (2011). "HuCAL PLATINUM, a synthetic Fab library optimized for sequence diversity and superior performance in mammalian expression systems," *J Mol Biol.*, 413:261-78, both of which are incorporated by reference for their teachings thereof.

The detection antibody is conjugated to at least one agent suitable for detection by colorimetric or other assay. In some aspects, a second detection antibody specific for the first detection antibody is used, and the second detection antibody is conjugated to the agent that is suitable for detection by colorimetric or other assay. In some aspects the agent suitable for detection by colorimetric assay is biotin. Horseradish peroxidase (HRP) strongly binds to biotin and reacts with 3,3',5,5'-tetramethylbenzidine (TMB) to form a colored product. In some aspects, the colorimetric assay uses HRP and TMB to measure the concentration of PAR in a CSF sample of a patient.

In another aspect, disclosed herein is a method for determining the therapeutic efficacy of a medical treatment for Parkinson's disease, the method comprising: collecting a sample of cerebrospinal fluid (CSF) from a patient, measuring the poly(ADP-ribose) (PAR) concentration in the CSF sample, and comparing the PAR concentration in the patient to a PAR concentration in at least one control sample.

In some aspects, the control sample is a previously collected sample of CSF from the same patient. The previously collected sample of CSF may have been collected at any time in the past. For example the sample may have been collected 1 month, 2 months, 3 months, 4 months, 6 months, 9 months, 12 months, 15 months, 18 months, 21 months, 24 months, 27 months, 30 months, 33 months or 36 months prior to the currently collected sample. In some aspects, the sample is collected at any point during the lifetime of the patient. This sample collection can be done on regular or repeated basis as part of routine monitoring of the health of a patient. In some aspects, the control sample is taken from a healthy patient. Healthy as used herein means that the patient is not exhibiting any symptoms of a medical condition that might affect the results of the test. In some aspects, the healthy patient is not exhibiting any symptoms of PD or similar neurological condition.

It has been previously demonstrated that activation of PARP-1 and the accumulation of PAR are implicated in the neuropathologies of PD, so in some aspects disclosed herein, an increase in the PAR concentration in the CSF of a patient indicates that the patient either has PD or is at risk of developing PD. In some aspects, if the PAR concentration in a patient is higher than the control sample that was previously collected from the same patient, it is indicative that the PD in the patient is worsening. In some aspects, an increase in the PAR concentration in the patient compared to the control sample that was previously collected from the same patient, it is indicative that the medical treatment received by the patient is not arresting the progression of the disease.

In a patient previously diagnosed with PD, either using the methods and techniques disclosed herein or by another method, and the patient is receiving medical treatment for PD, when the PAR concentration in the patient increases as compared to the PAR concentration of a previously collected sample from the same patient, it is indicative that the medical treatment is not arresting the disease. In these instances a medical professional will make a decision as to whether or not to continue the same treatment or alter the treatment received by the patient.

In yet another aspect, disclosed herein is a method of monitoring the disease progression of a patient with PD, the method comprising: collecting a sample of cerebrospinal fluid (CSF) from the patient, measuring the poly(ADP-ribose) (PAR) concentration in the CSF sample, and comparing the PAR concentration in the patient to a PAR concentration in at least one control sample.

In some aspects, the control sample is a previously collected sample of CSF from the same patient. The previously collected sample of CSF may have been collected at any time in the past. For example the sample may have been collected 1 month, 2 months, 3 months, 4 months, 6 months, 9 months, 12 months, 15 months, 18 months, 21 months, 24 months, 27 months, 30 months, 33 months or 36 months prior to the currently collected sample. In some aspects, the sample is collected at any point during the lifetime of the patient. This sample collection can be done on regular or repeated basis as part of routine monitoring of the health and/or treatment of a patient.

When comparing the PAR concentration to a sample taken from the same patient at an earlier time period, an increase of the PAR concentration in the CSF is indicative that the condition of the patient is worsening. If the patient is receiving medical treatment, then an increased PAR concentration would indicate that the treatment is not effective in the patient. If the PAR concentration is the same or lower, it would indicate that the treatment the patient is receiving is effective in either slowing or arresting the progression of the disease. The PAR concentration is measured using a sandwich-ELISA as disclosed elsewhere herein.

In still yet another aspect, disclosed herein is a method for diagnosing, or determining that a patient is at risk of developing, PD, the method comprises: collecting a sample of cerebrospinal fluid (CSF) from the patient, measuring the poly(ADP-ribose) (PAR) concentration in the CSF sample, and comparing the PAR concentration in the patient to a PAR concentration in at least one control sample.

According to this method, in some aspects, a patient is diagnosed with PD, or is at risk of developing PD, if the PAR concentration in the CSF of the patient is greater than a predetermined concentration. In some aspects, that predetermined concentration is the PAR concentration in the CSF of a healthy patient. In some aspects, measuring the PAR concentration in the CSF of the patient is done using a sandwich-ELISA as disclosed elsewhere herein.

According to this method, if a patient has a PAR concentration higher than a control sample from either a healthy patient or a control sample previously taken from the same patient, then the patient is diagnosed with PD or is determined to be at risk of developing PD. If the PAR concentration in the CSF of the patient is lower than or equal to the PAR concentration in a negative control or a control sample of a healthy patient, then the patient does not currently have PD or the risk of developing PD is low at that time. Because the ultimate cause of PD is as yet unknown, it is not possible to conclude that a patient will never develop PD.

The term "theranostics" as used herein refers to the process by which an individualized treatment plan or therapy is developed for a specific patient. The word defines the ongoing clinical efforts to develop more specific, individualized treatments for various diseases, and to combine diagnostic and therapeutic capabilities into a single agent. The rationale arose from the fact that many diseases, such as PD and cancer, are immensely heterogeneous, and current treatments are effective for only limited patient populations or subpopulations and/or at only specific stages of disease progression. The hope was that a close combination of diagnosis and therapeutics could provide therapeutic protocols that are more specific to individuals and, therefore, more likely to offer improved prognoses.

There are no standard treatments for PD. An individualized treatment plan is developed for each patient based on their symptoms and overall health. Treatment options include medication, surgery, and life style modifications. Examples of medicaments used to treat PD include, but are not limited to, levodopa, dopamine agonists, amantadine, anticholinergics, COMT inhibitors, and MAO-B inhibitors. Surgical treatments include, but are not limited to, deep brain stimulation, thalamotomy, pallidotomy, and subthalamotomy. Lifestyle treatments include, but are not limited to, exercise and diet. Many patients often explore so-called "alternative medicine" which can include herbal and vitamin supplements. Additional treatments are always being studied in clinical trials. In some aspects, a patient is receiving at least one type of medical treatment specifically for PD. It is not uncommon for a patient to receive multiple different types of medical treatment in order to determine the optimal combination for the patient. Regardless of how many different types of medical treatment are being administered to the patient, the methods and techniques disclosed herein are suitable for assessing the PAR concentrations in the patient and determining the therapeutic efficiency of the medical treatment or combination of those treatments.

Also disclosed herein is a theranostic method that will aid medical professionals in developing an individualized treatment plan for a patient with PD. The method comprises collecting a sample of cerebrospinal fluid (CSF) from a patient who is receiving at least one medical treatment for PD, measuring the poly(ADP-ribose) (PAR) concentration in the CSF sample, and comparing the PAR concentration in the patient to a PAR concentration in at least one control sample.

The medical treatment may be any treatment disclosed elsewhere herein or it may be any other treatment administered by, or under the supervision of, a medical professional. In some aspects, if a patient has been administered a medicament for at least a time period where the medicament is expected to have an effect, and the PAR concentration in the patient has increased, then the method further comprises altering the manner in which the medicament is administered to the patient. Altering the manner in which the medicament is administered may comprise increasing or decreasing the dose of the medicament; it may comprise increasing or decreasing the frequency that the medicament is taken by or administered to the patient; it may include changing or eliminating a specific medicament being administered to the patient.

In another aspect, if the PAR concentration in the CSF of the patient has increased compared to a previously collected sample of CSF from the same patient, the medical professional may alter then medical treatment received by the patient to add in an additional form of treatment. For example, if the patient has only received one or more medicaments as treatment, then the medical professional may recommend a surgical alternative treatment. Alternatively, if the patient has received one medicament (e.g., levodopa), then the medical professional may recommend the addition of a second medicament (e.g., a dopamine agonist). The exact nature in which the medical professional alters the medical treatment of the patient will be individualized based on the medical needs of the patient and the professional judgment of the medical professional.

As used herein, the term "biomarker" refers to the definition established by the National Institutes of Health Biomarkers Definitions Working Group. It is "a characteristic that is objectively measured and evaluated as an indicator of normal biological processes, pathogenic processes, or pharmacologic responses to a therapeutic intervention." Also disclosed herein is the use of PAR in the CSF of a patient as a biomarker for PD. The methods disclosed elsewhere herein are suitable for either diagnosing a patient with PD or determining if a patient is at risk for PD. An elevated concentration of PAR in the CSF of a patient is indicative of PD or indicative that a patient is at risk of developing PD. If a patient is already exhibiting symptoms of PD, then an elevated concentration of PAR in the CSF of the patient suggests that the patient has PD. Symptoms of PD include, but are not limited to, tremors or shaking, changes in writing or speech patterns, loss of smell, difficulty sleeping, difficulty walking or moving, slowed movements, constipation, masked face, dizziness or fainting, or stooping or hunching over. These early warning signs of PD coupled with an elevated PAR concentration in the CSF of a patient suggest the patient has PD. Further testing may be necessary to confirm this diagnosis. Also disclosed herein is the use of PAR as a biomarker for PD. Detection of an elevated concentration of PD in the CSF of a patient indicates that the patient either has or is at risk of developing PD.

Figure 2:
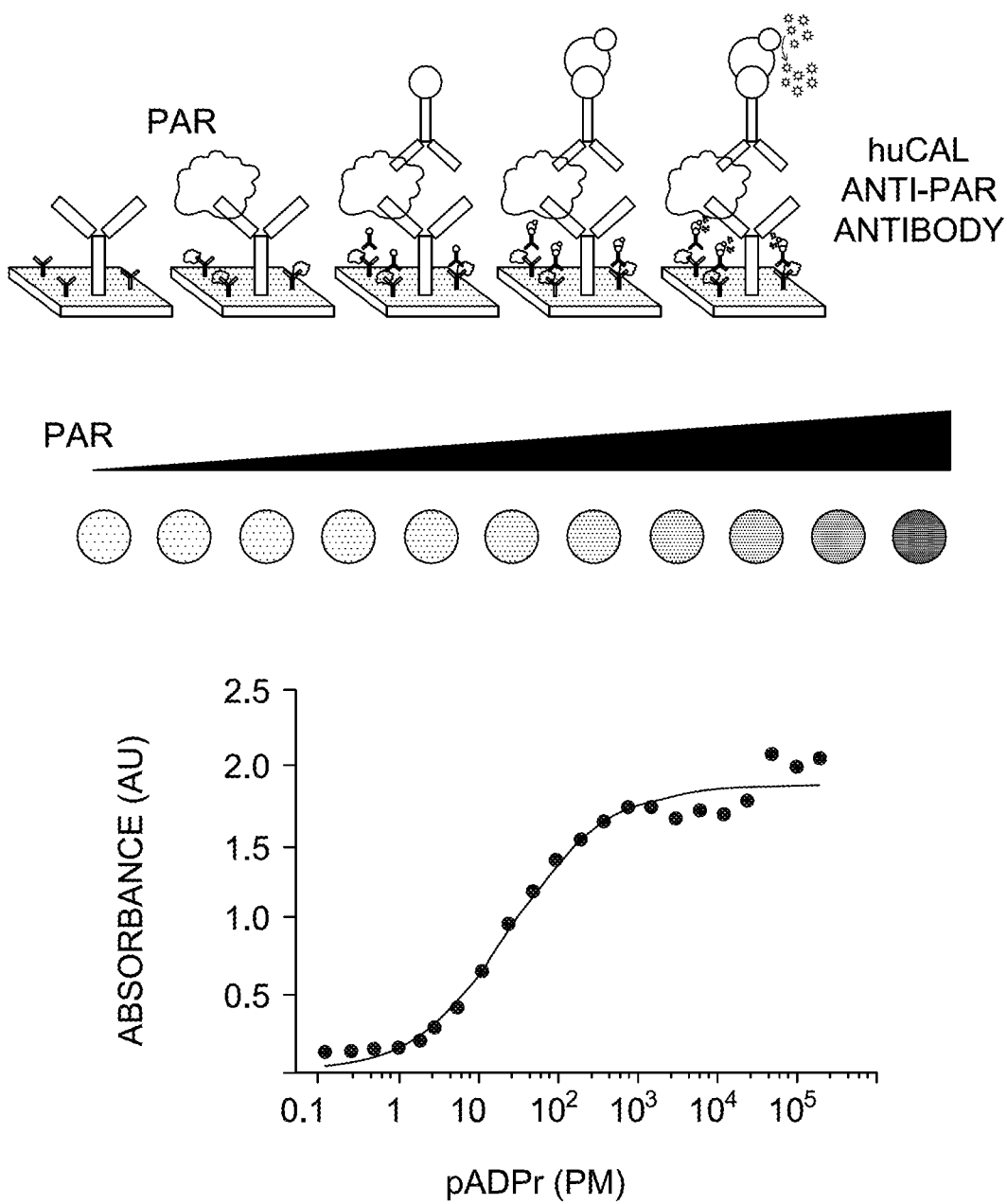
FIG. 2 is a schematic drawing of the sandwich ELISA assay with an anti-PAR antibody and a concentration curve.

As used herein, "sandwich ELISA," and illustrated in FIG. 2, is a variant of the traditional ELISA that is highly specific for sample antigen detection and quantification. The sandwich ELISA quantifies antigens between two layers of antibodies (i.e., a capture antibody and a detection antibody). The antigen to be measured must contain at least two antigenic epitopes capable of binding to the antibody, since at least two antibodies act in the sandwich. Either monoclonal or polyclonal antibodies can be used as the capture and detection antibodies in a sandwich ELISA system. Monoclonal antibodies recognize a single epitope that allows for the fine detection and quantification of small differences between antigens while polyclonal antibodies are often used as the capture antibody to trap as much of the antigen as possible. One advantage of sandwich ELISA is in the ease of sample preparation, meaning the sample does not have to be purified before analysis. Another advantage of sandwich ELISA is the sensitivity of the technique to detect and quantify specific antigens.

In some aspects of the sandwich ELISA as disclosed herein, the capture antibody is immobilized on a plate, chip or other physical structure. In the second step, the immobilized capture antibody is exposed to the sample that includes the target protein. As described herein, the target protein is PAR. After a predetermined time period, a first detection antibody is added to bind to the antigen that is bound to the immobilized capture antibody. In some embodiments, a second detection antibody is added to bind to the first detection antibody. In all embodiments, at least one of the detection antibodies will comprise a detectable substrate. The detectable substrate may be an enzyme that reacts with an additional reagent to form a detectable, and quantifiable, product, or detectable substrate may be detectable without further reaction. In some embodiments, the detectable substrate is biotin. In all embodiments, the detectable substrate will be detectable and quantifiable. In some embodiments, the detection of the substrate will be colorimetric.

Human antibodies suitable for use in the sandwich ELISA disclosed herein are known in the art. For example, human myeloma and mouse-human heteromyeloma cell lines for the production of human monoclonal antibodies have been described in the art (Kozbor J., Immunol. 133:3001, 1984.; Brodeur et al., "Monoclonal Antibody Production Techniques and Applications," Marcel Dekker, Inc., New York, 1987, both of which are incorporated by reference for their teachings thereof). In some aspects, the antibody is an anti-PAR antibody prepared from a human combinatorial antibody library (e.g., HuCAL® Technology from Bio-RAD®).

Figure 5:
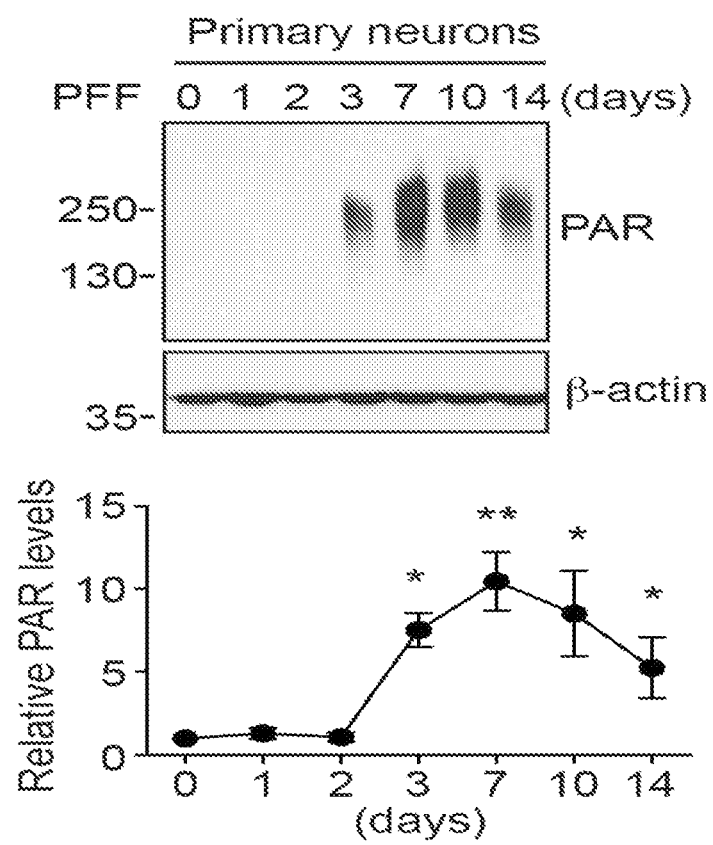
FIG. 5 shows activation of PARP-1 in α-syn PFF-treated primary cortical neurons. The representative western blot analysis (top) and quantification (bottom) of the levels of PAR accumulation. Bars represent mean±s.e.m. One-way ANOVA followed by Tukey's post hoc test (n=3-4).
Figure 6:
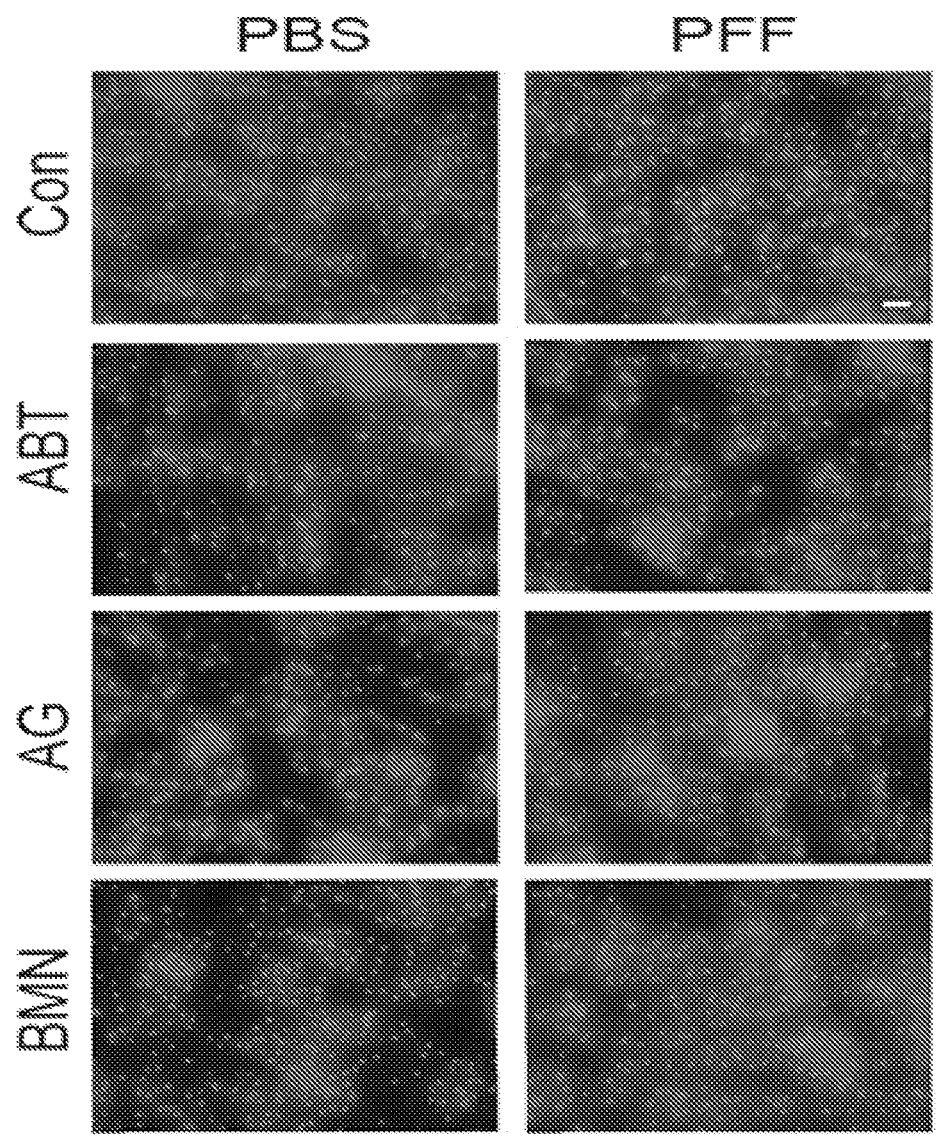
FIG. 6 shows representative images of Hoechst and propidium iodide (PI) staining from primary cortical neurons pre-incubated with either ABT-888 (10 μM), AG-014699 (1 μM) or BMN 673 (10 μM) for 1 h, and further incubated with α-syn PFF (5 μg/ml) for 14 days. Scale bar, 20 μm.
Figure 7:
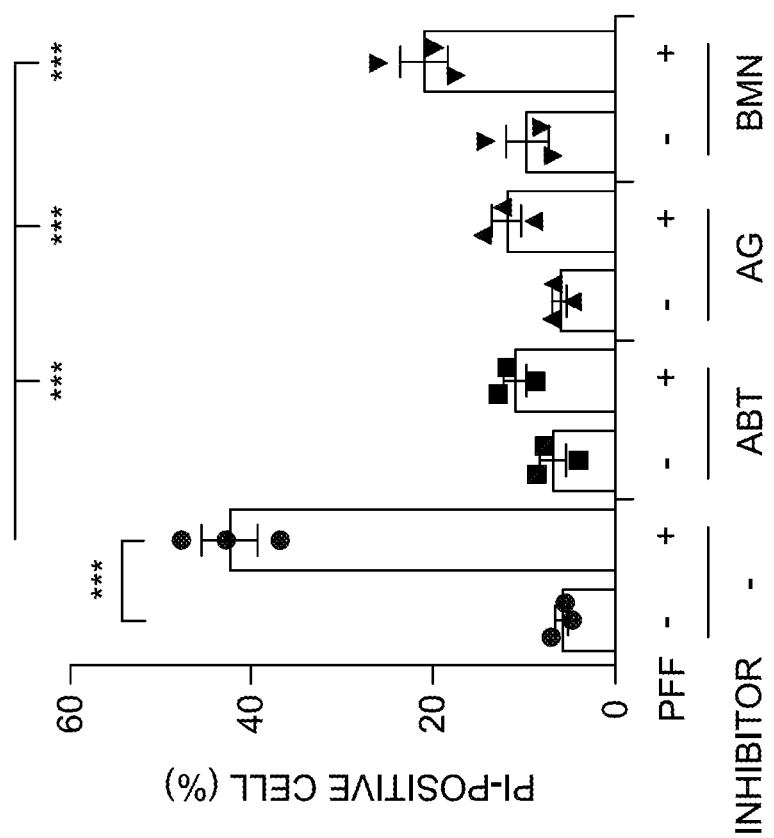
FIG. 7 shows quantification of cell death. Bars represent mean±s.e.m. One-way ANOVA followed by Tukey's post hoc test (n=3).
Figure 8:
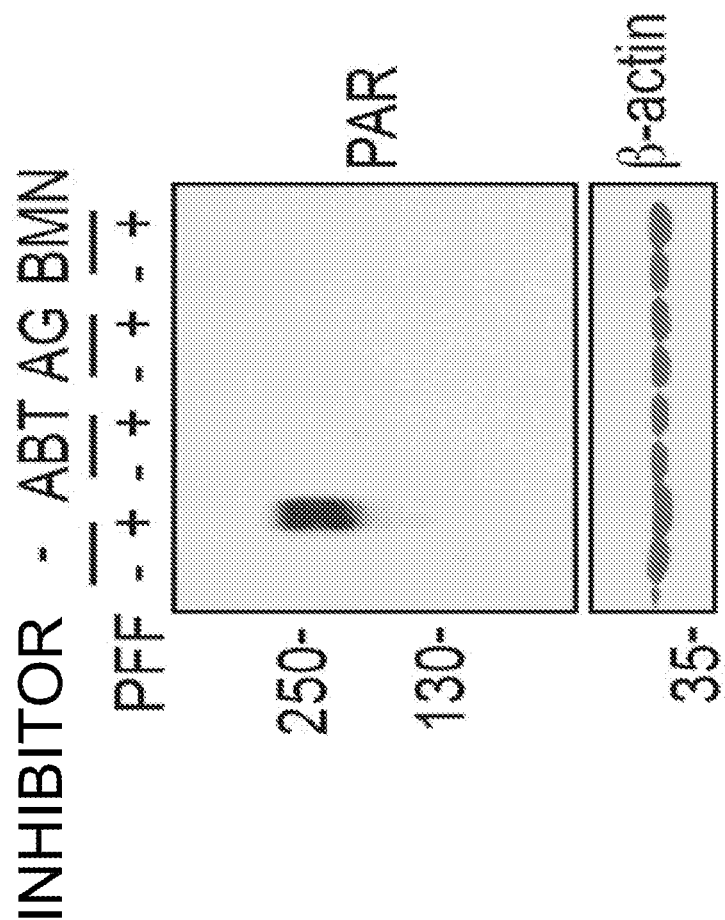
FIG. 8 shows inhibition of α-syn PFF-induced PAR accumulation was determined by western blot analysis.
Figure 9:
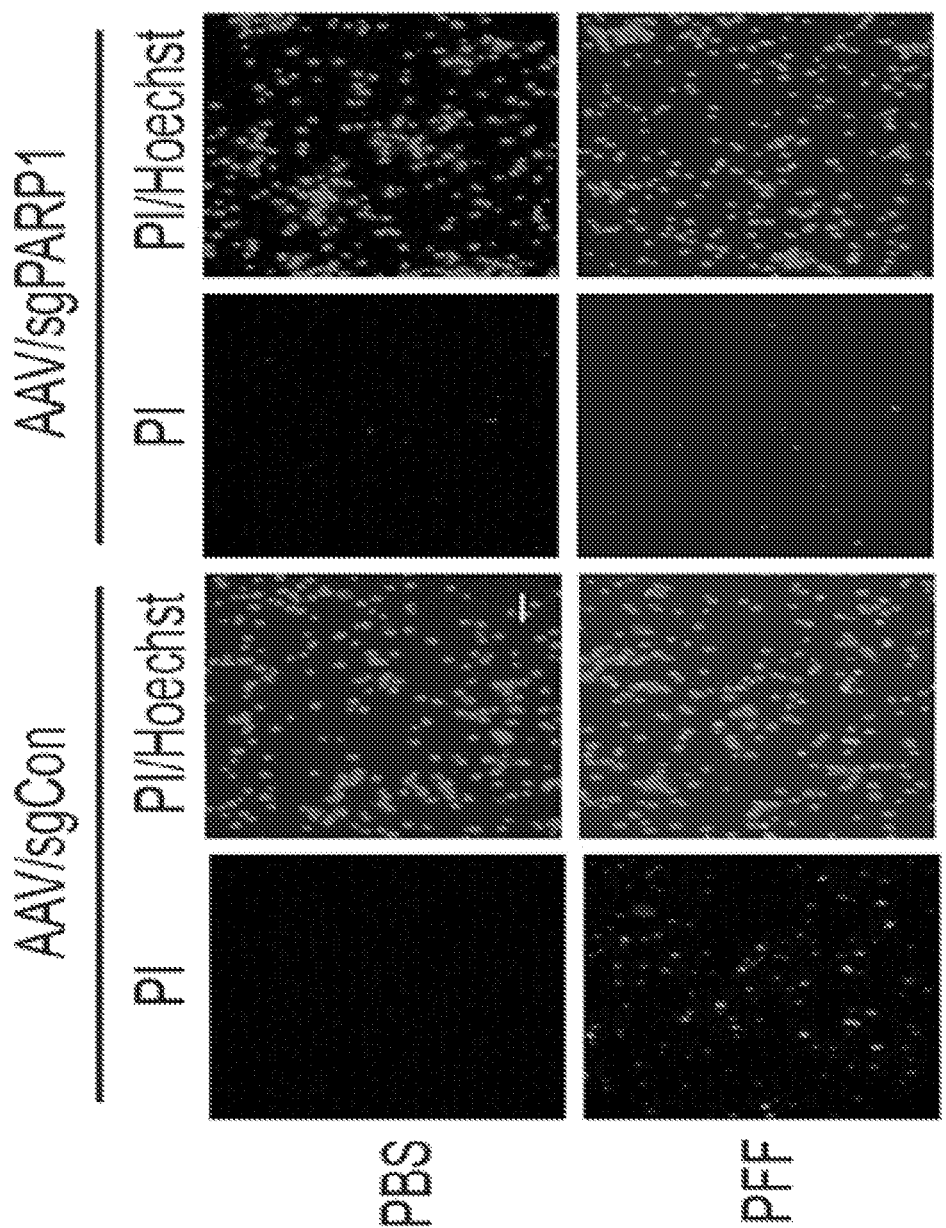
FIG. 9 shows representative images of Hoechst and propidium iodide (PI) staining from primary cortical neurons transduced with AAV-sgCon or AAV-sgPARP-1, and further incubated with α-syn PFF for 14 days. Scale bar, 20 μm.
Figure 10:
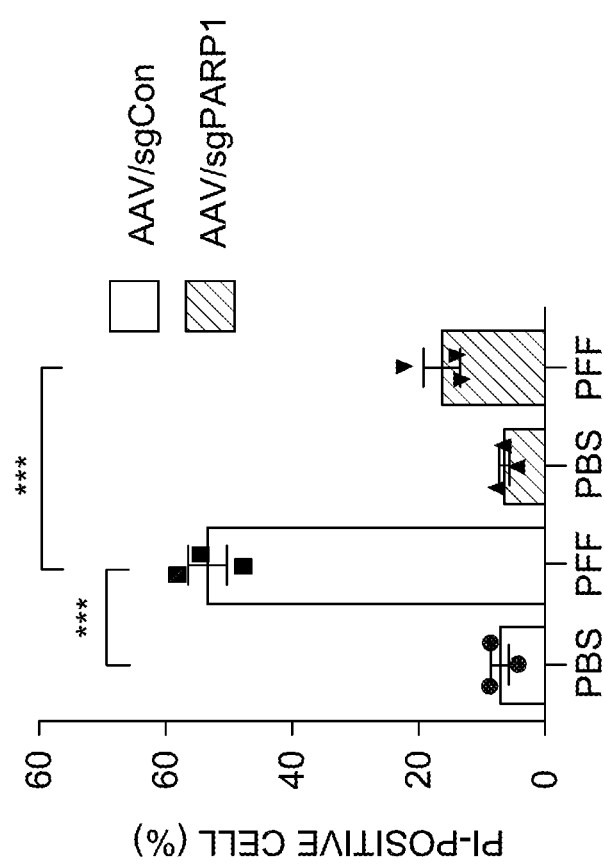
FIG. 10 shows quantification of cell death. Bars represent mean±s.e.m. (n=3).
Figure 11:
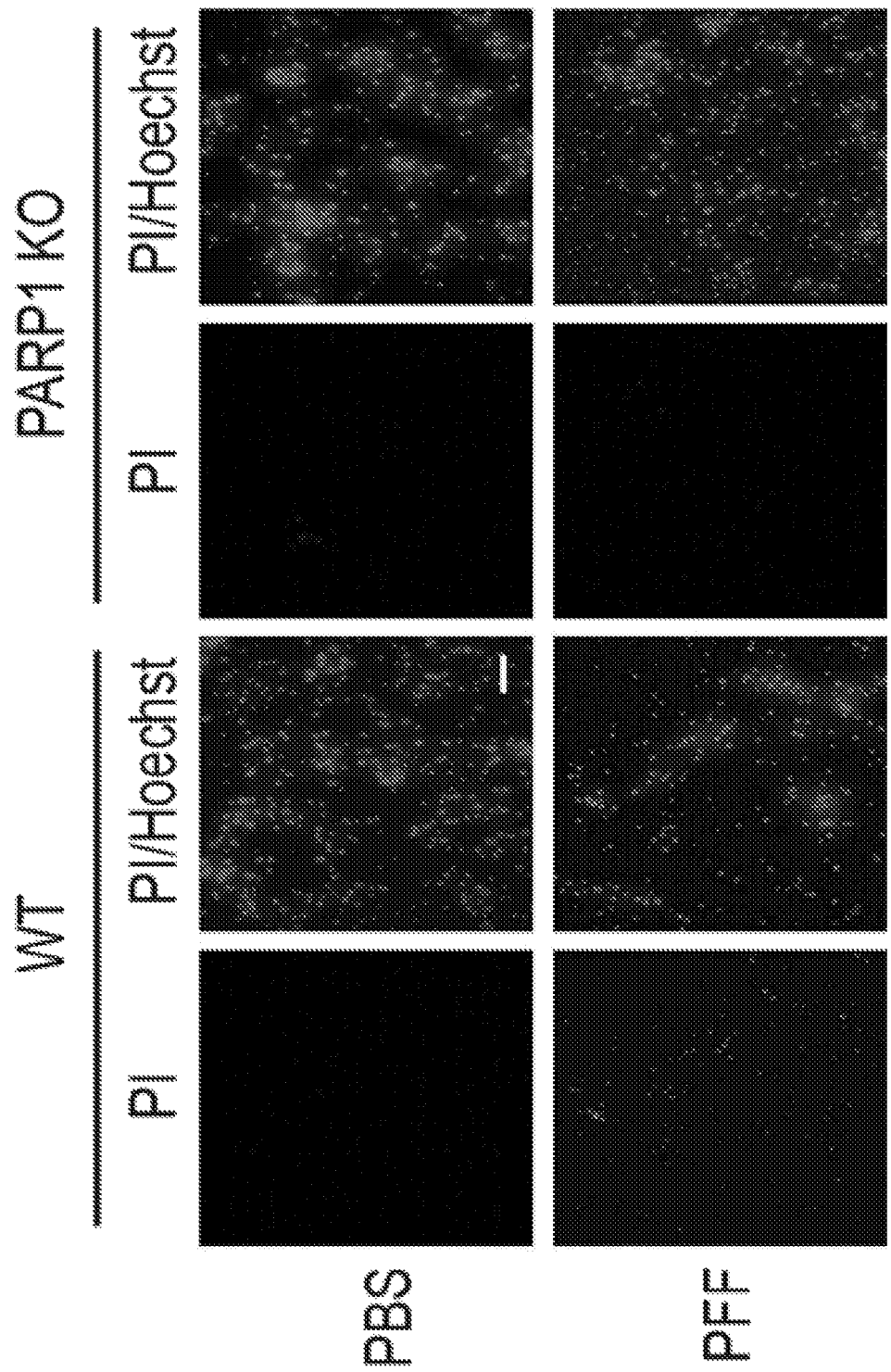
FIG. 11 shows representative images of Hoechst and propidium iodide (PI) staining from WT or PARP-1 KO primary cortical neurons, and further incubated with α-syn PFF for 14 days. Scale bar, 20 μm.
Figure 12:
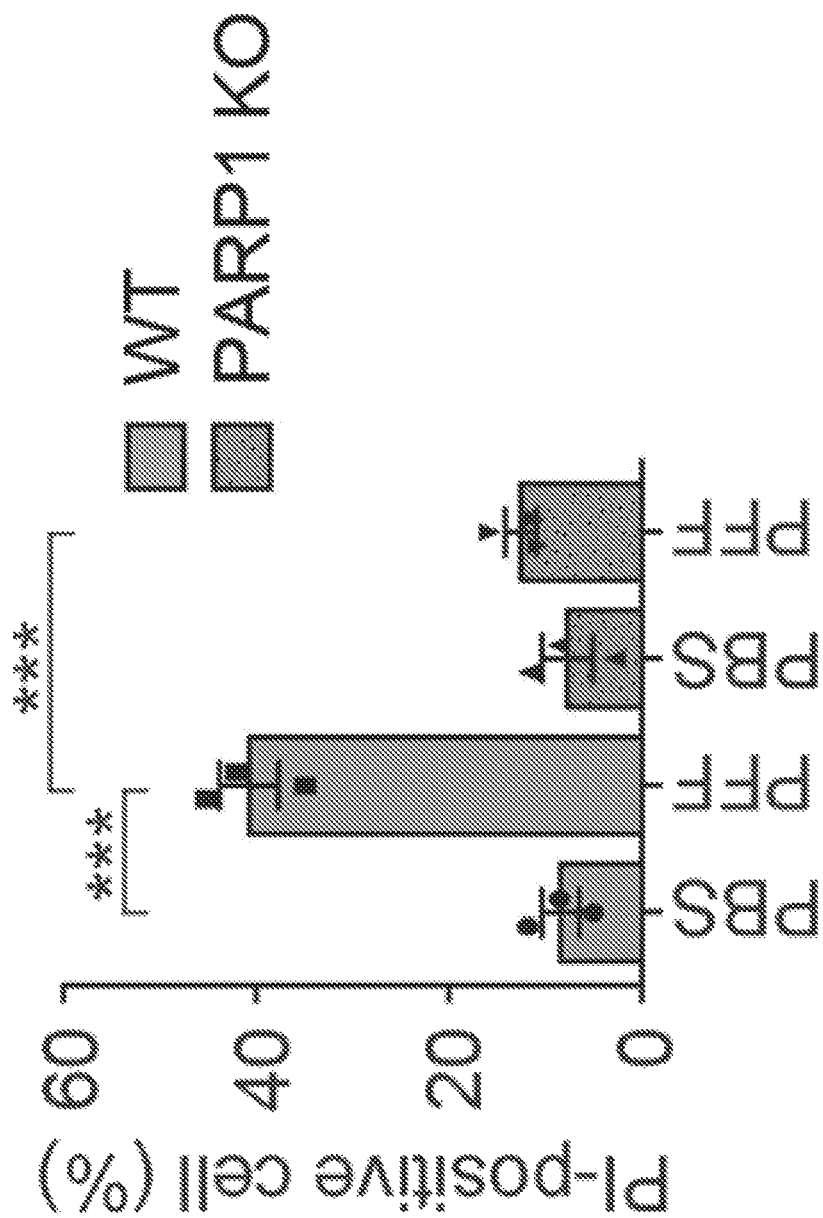
FIG. 12 shows quantification of cell death. Bars represent mean±s.e.m. One-way ANOVA followed by Tukey's post hoc test (n=3). *P<0.05, P<0.005, *P<0.0005.
Figure 37:
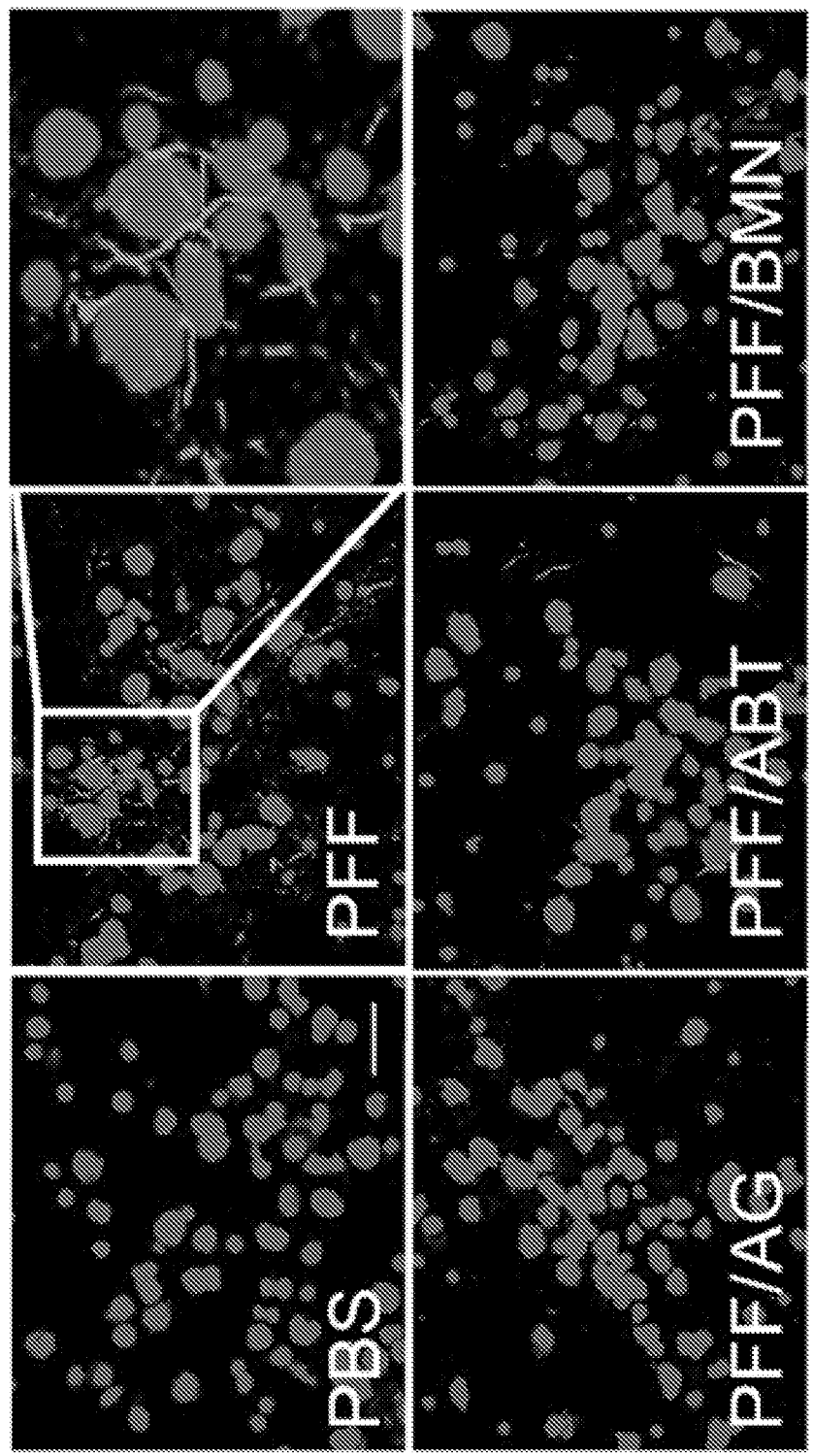
FIG. 37 shows representative images of p-α-syn (red) in primary cortical neurons pre-incubated with either ABT-888 (10 μM), AG-014699 (1 μM) or BMN 673 (10 μM) for 1 h, and further incubated with α-syn PFF for 7 days. Nuclei are stained with DAPI (blue).
Figure 38:
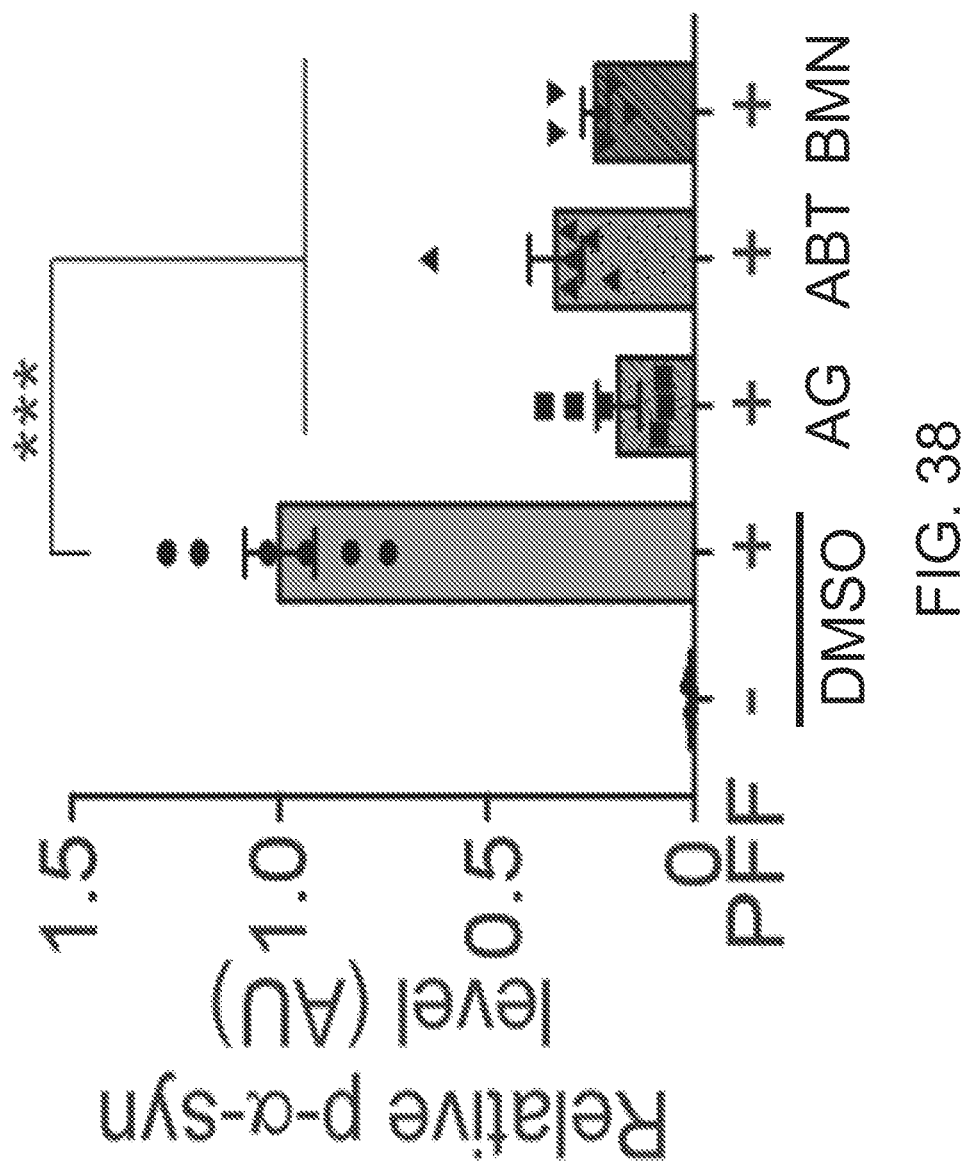
FIG. 38 shows quantification of p-α-syn signals normalized with DAPI. Bars represent mean±s.e.m. One-way ANOVA followed by Tukey's post hoc test (n=6).
Figure 39:
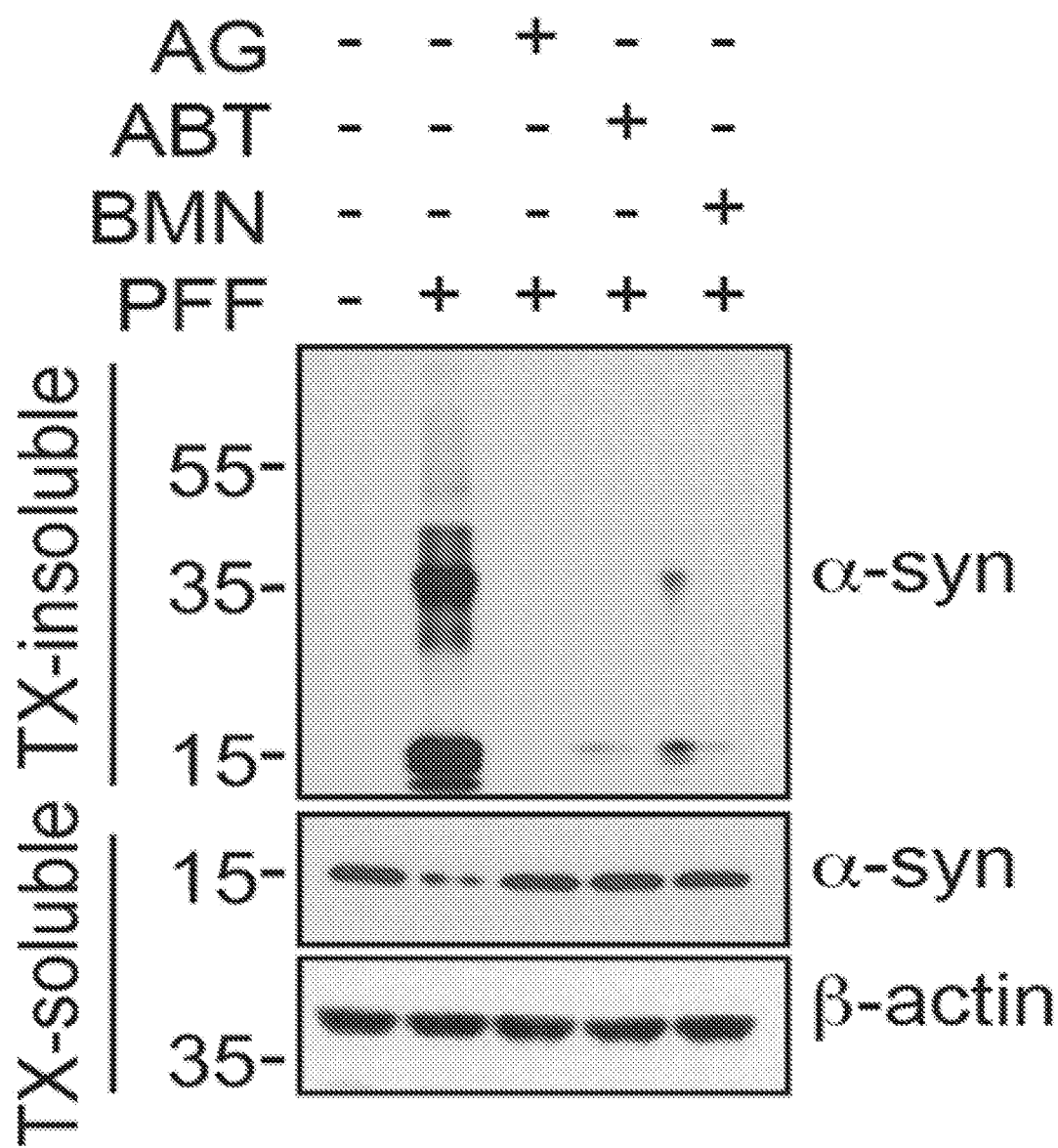
FIG. 39 shows representative immunoblots of α-syn in the detergent-soluble and insoluble fraction from primary cortical neurons pre-treated with PARP inhibitors for 1 h followed by incubated with α-syn PFF for 7 days.
Figure 40:
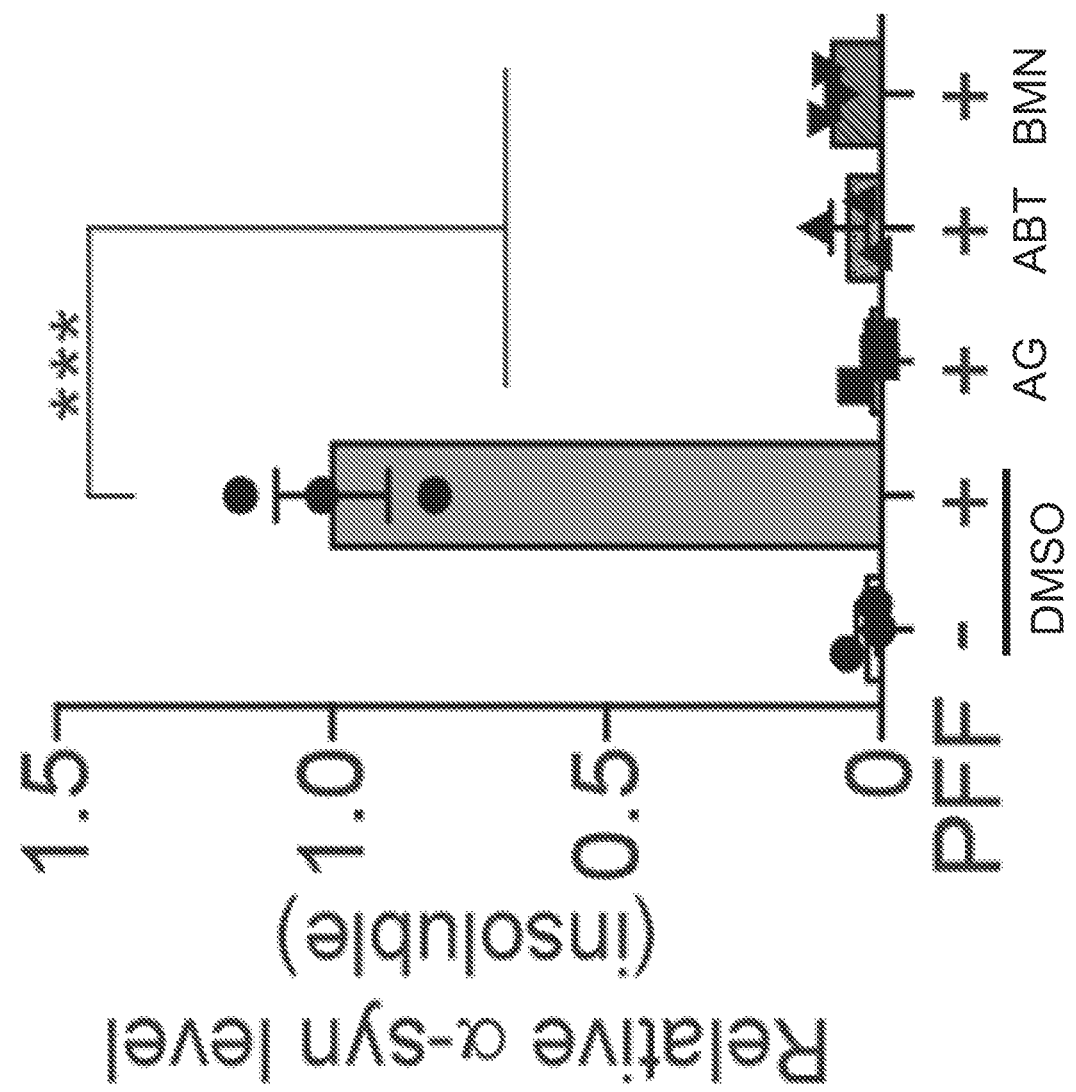
FIG. 40 shows quantification of α-syn levels in the detergent-insoluble fraction normalized to b-actin. Bars represent mean±s.e.m. One-way ANOVA followed by Tukey's post hoc test (n=3).
Figure 41:
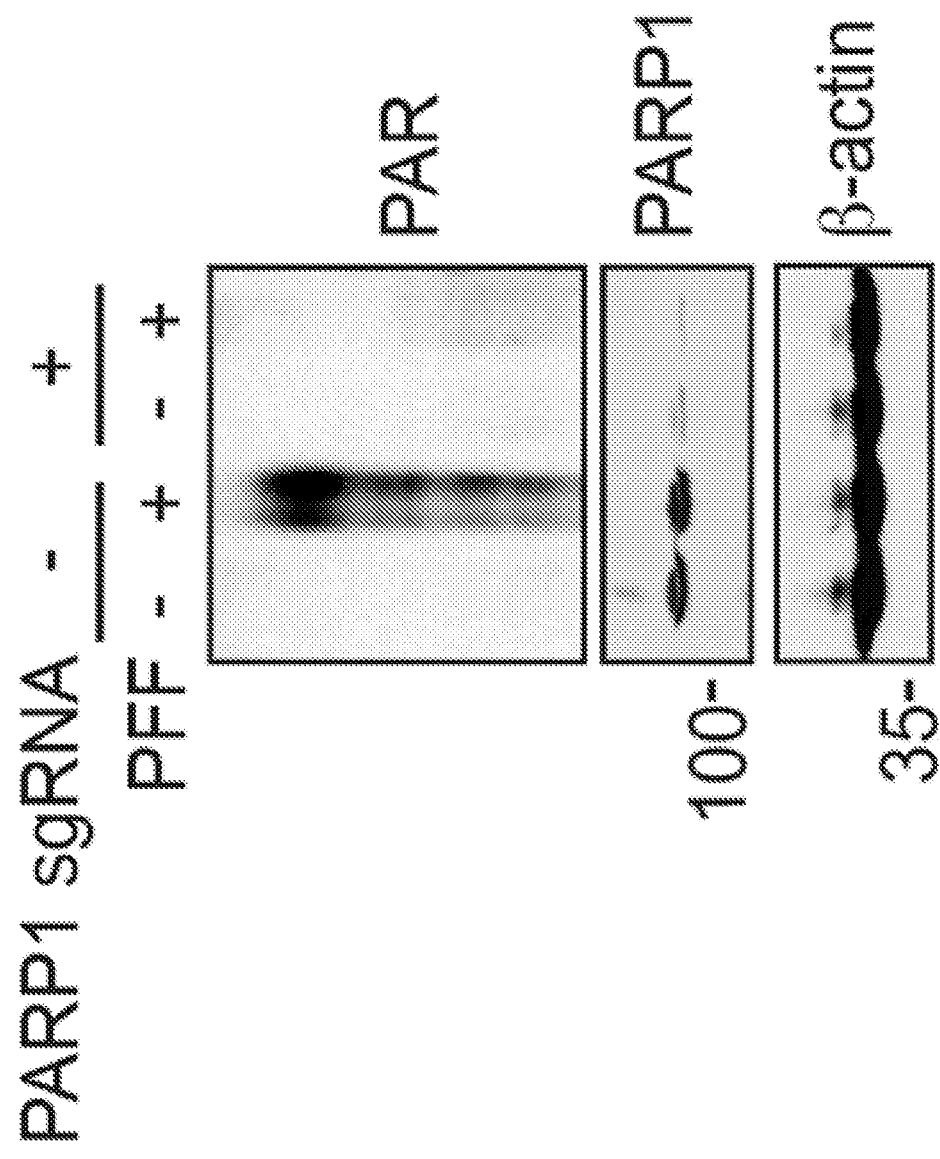
FIG. 41 shows inhibition of α-syn PFF-induced PAR accumulation in primary cortical neurons infected with AAV-sgPARP1.
Figure 42:
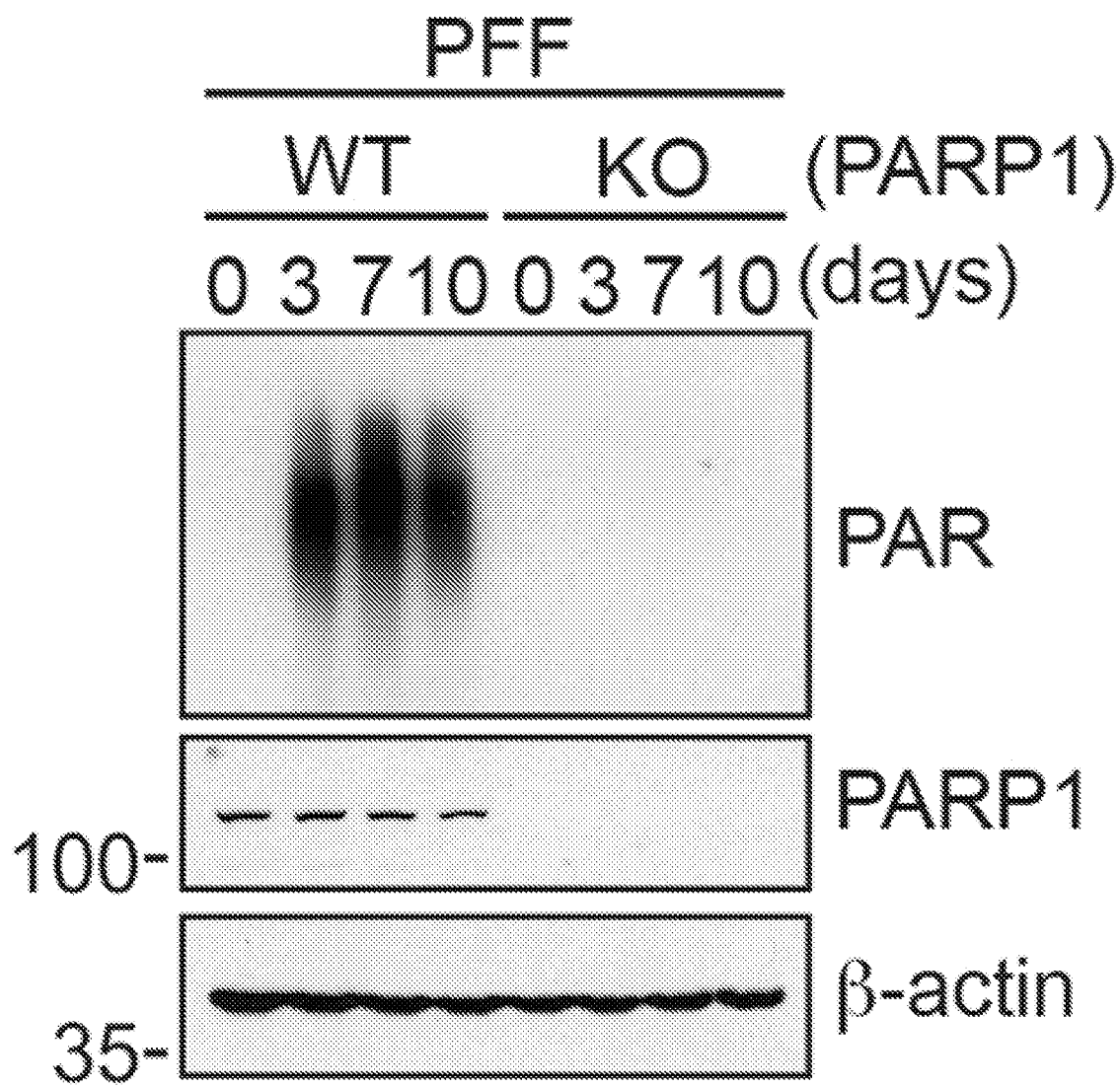
FIG. 42 shows inhibition of α-syn PFF-induced PAR accumulation in primary cortical neurons from PARP1 KO embryos.
Figure 43:
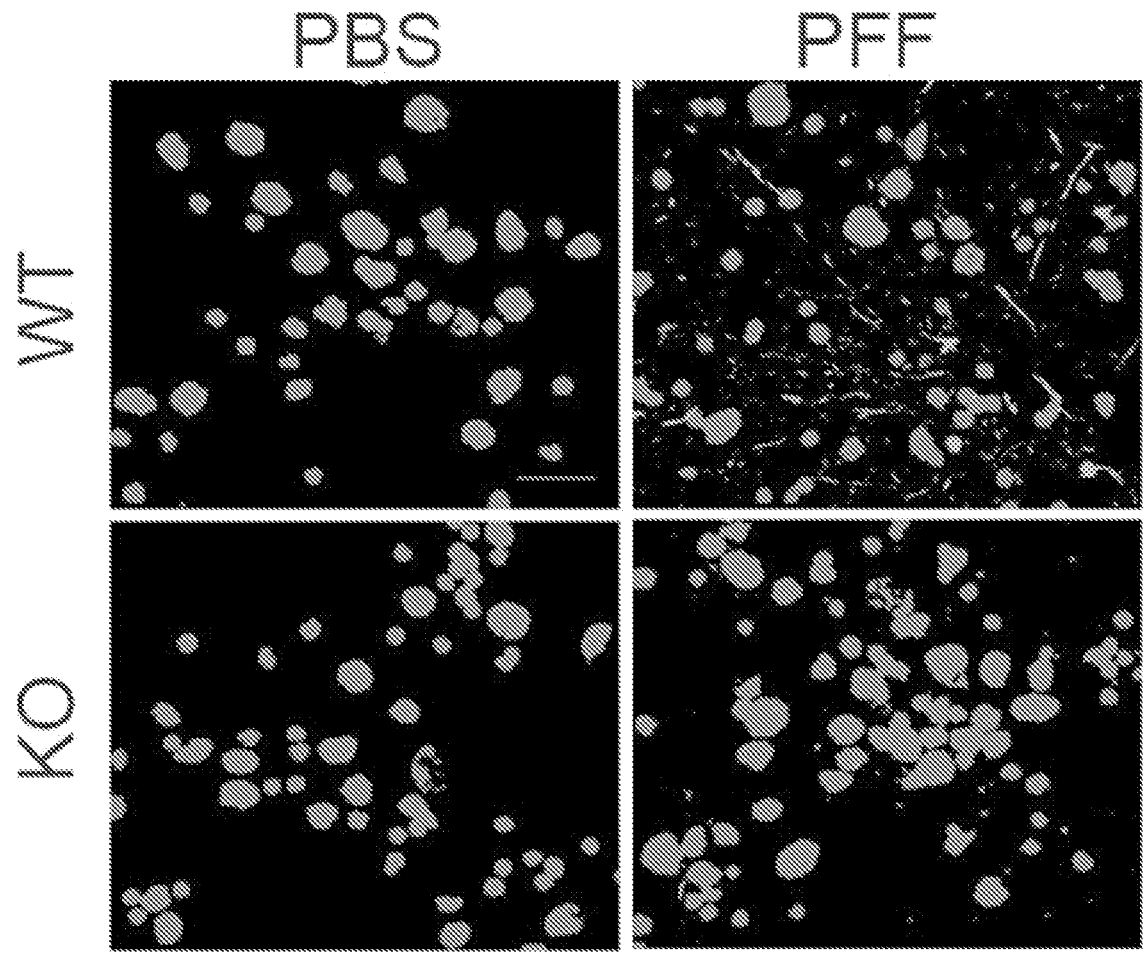
FIG. 43 shows representative images of p-α-syn (red) in primary cortical neurons pre-incubated with either ABT-888 (10 μM), AG-014699 (1 μM) or BMN 673 (10 μM) for 1 h, and further incubated with α-syn PFF for 7 days. Nuclei are stained with DAPI (blue).
Figure 44:
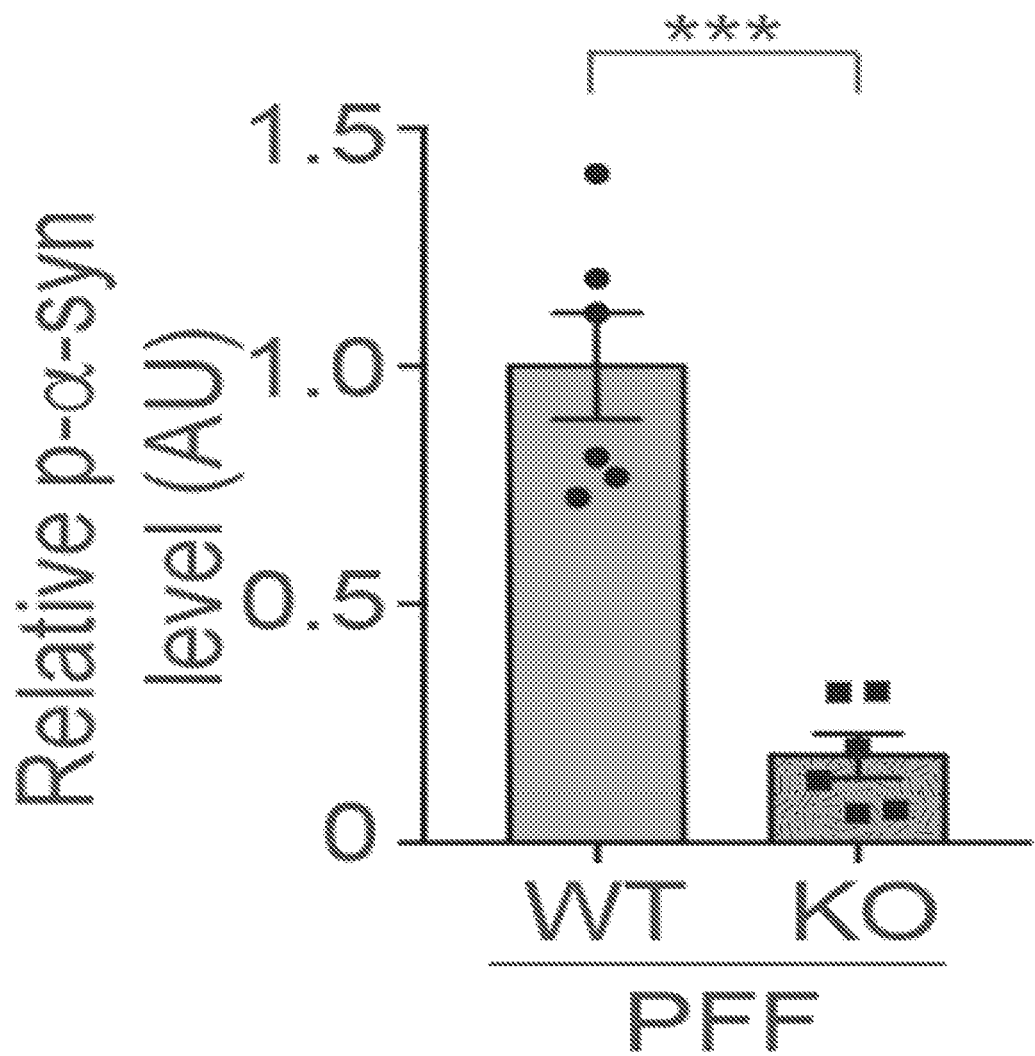
FIG. 44 shows quantification of p-α-syn signals normalized with DAPI. Bars represent mean±s.e.m. One-way ANOVA followed by Tukey's post hoc test (n=6).
Figure 45:
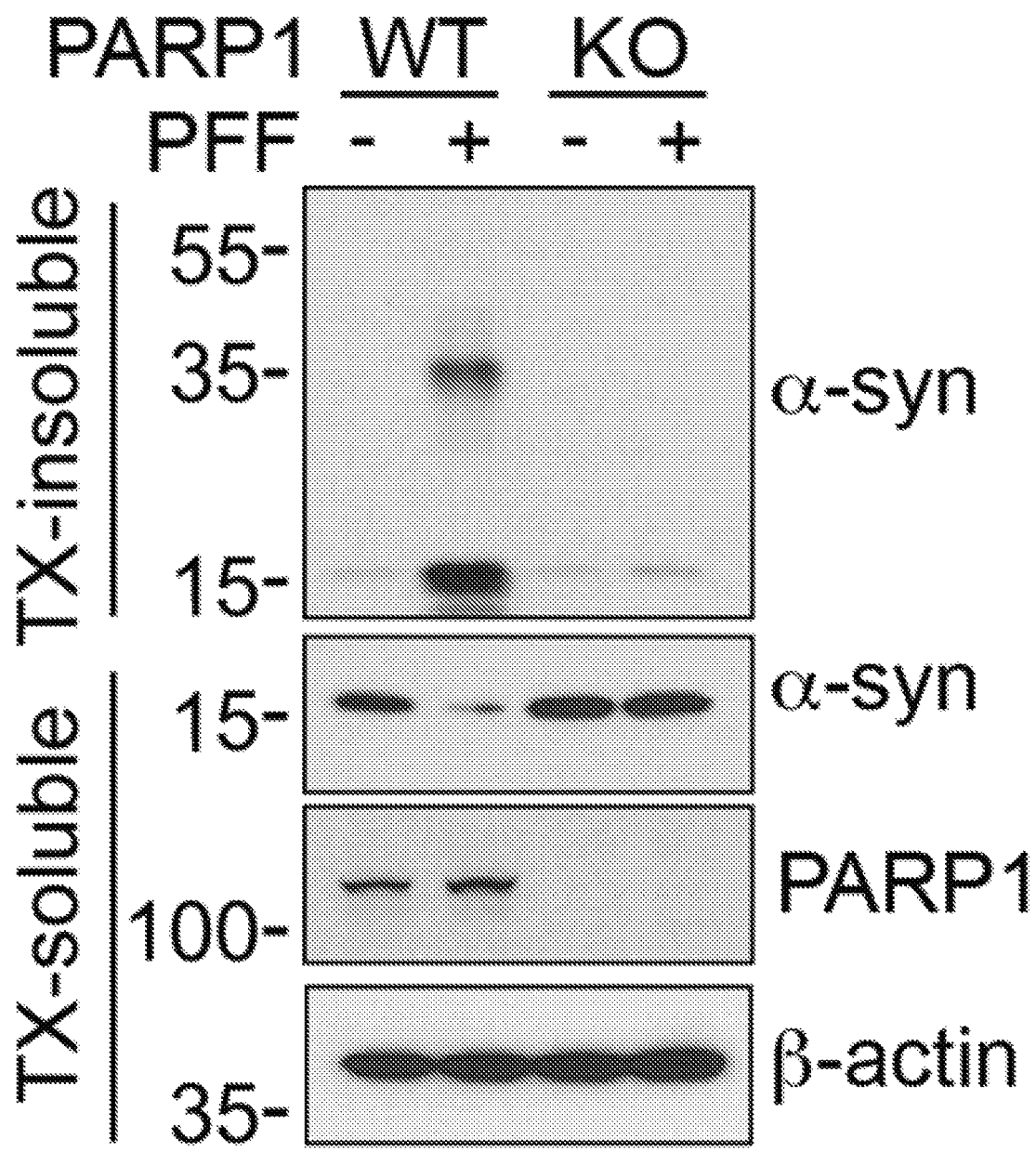
FIG. 45 shows representative immunoblots of α-syn in the detergent-soluble and insoluble fraction from WT or PARP1 KO primary cortical neurons incubated with α-syn PFF for 7 days.
Figure 46:
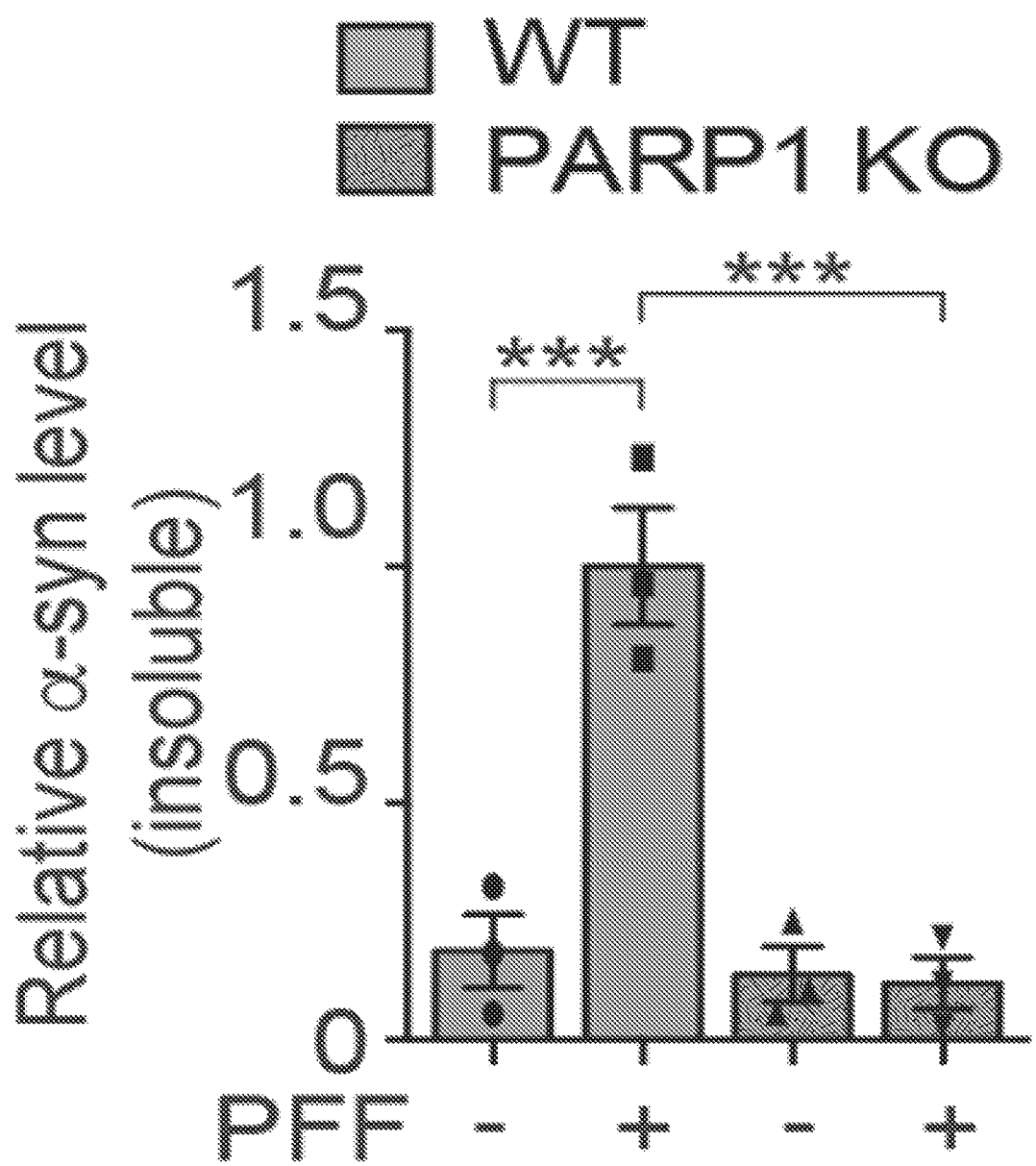
FIG. 46 shows quantification of α-syn levels in the detergent-insoluble fraction normalized to b-actin. Bars represent mean±s.e.m. One-way ANOVA followed by Tukey's post hoc test (n=3).
Figure 47:
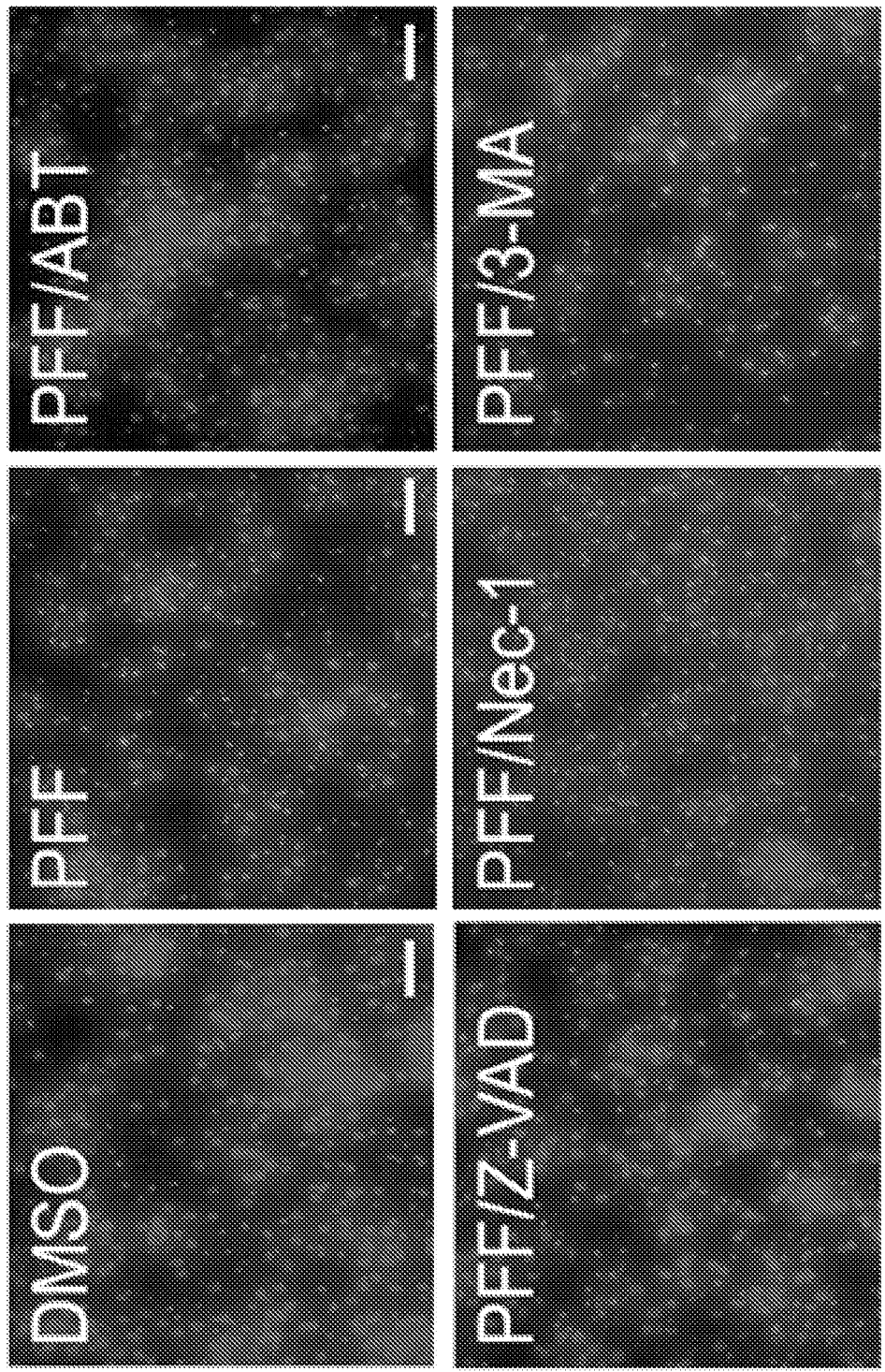
FIG. 47 shows representative images of Hoechst and propidium iodide (PI) staining from primary cortical neurons pre-treated with ABT-888, Z-VAD, NEC-1, or 3-MA for 1 h, followed by further incubation with α-syn PFF for 14 days. Scale bar, 20 μm.
Figure 48:
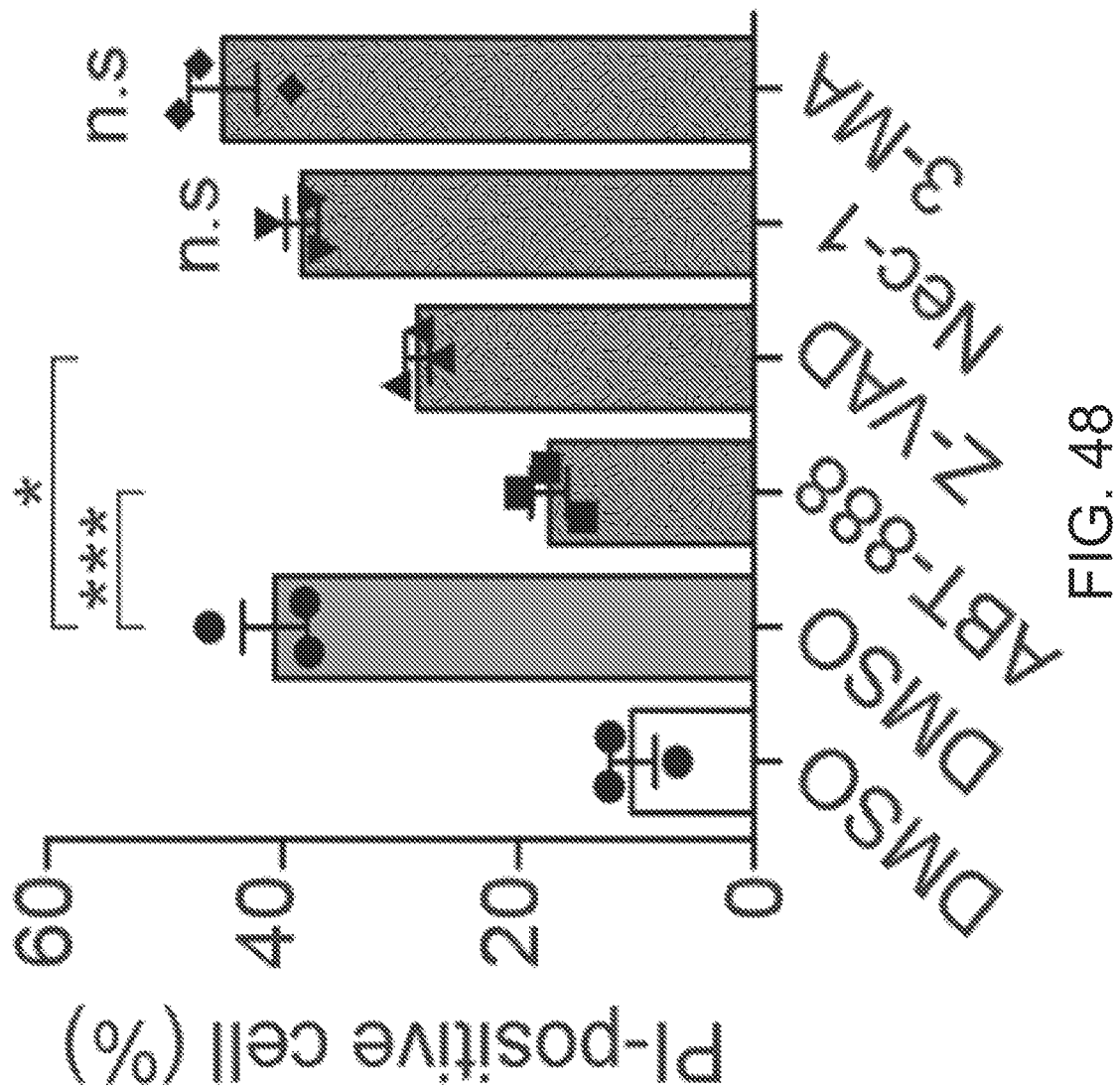
FIG. 48 shows quantification of cell death. Bars represent mean±s.e.m. One-way ANOVA followed by Tukey's post hoc test (n=3). *$P<0.05$, ***$P<0.001$.
Figure 49:
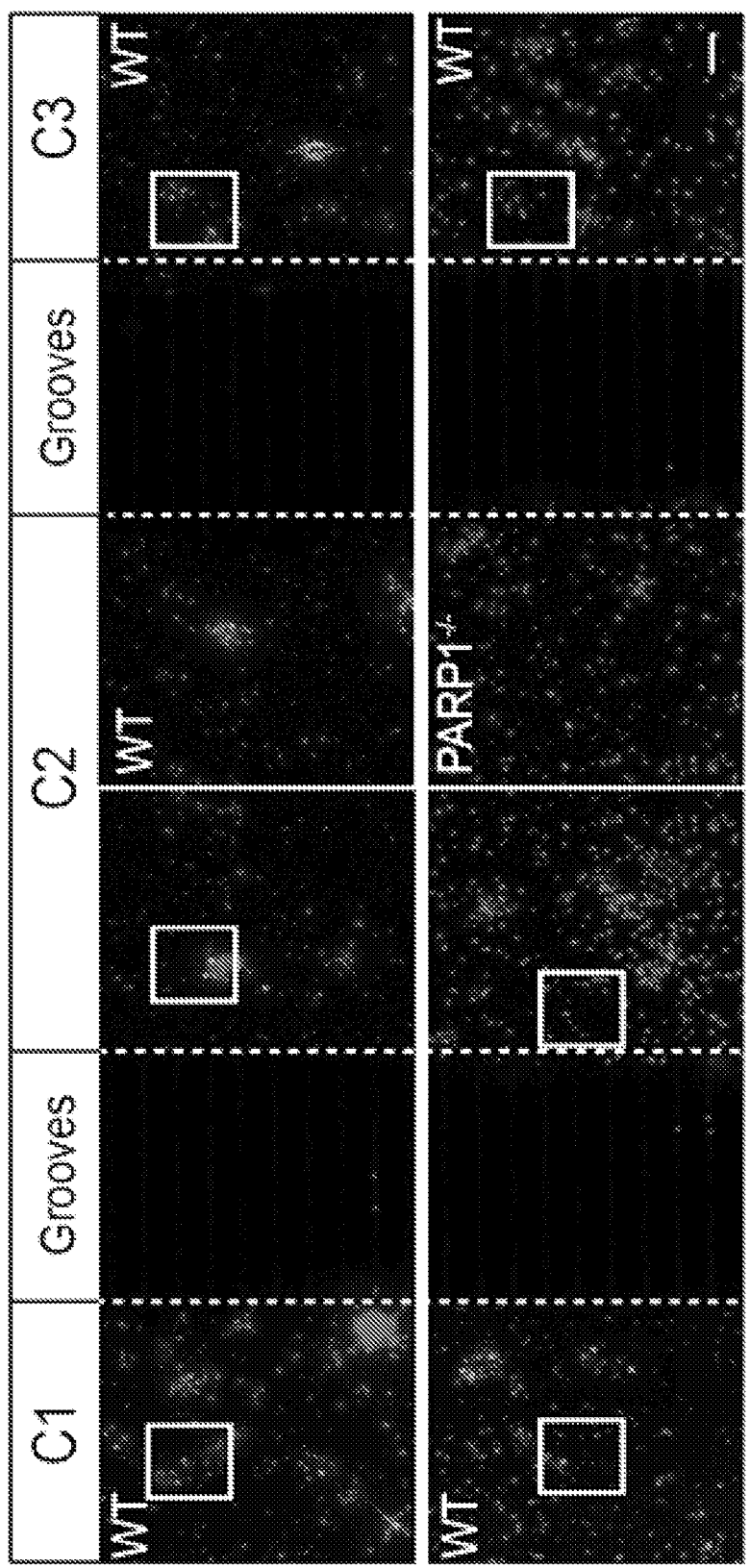
FIG. 49 shows representative images of α-syn PFF transmission. α-syn PFF was added to chamber 1 (C1) of the microfluidic device. On day 14, p-α-syn was detected in chamber 2 (C2) and chamber 3 (C3) when WT neurons were present in all three chambers, but very limited intensity of p-α-syn in PARP-1 KO neurons in C2 and WT neurons in C3. Scale bar, 100 μm.
Figure 50:
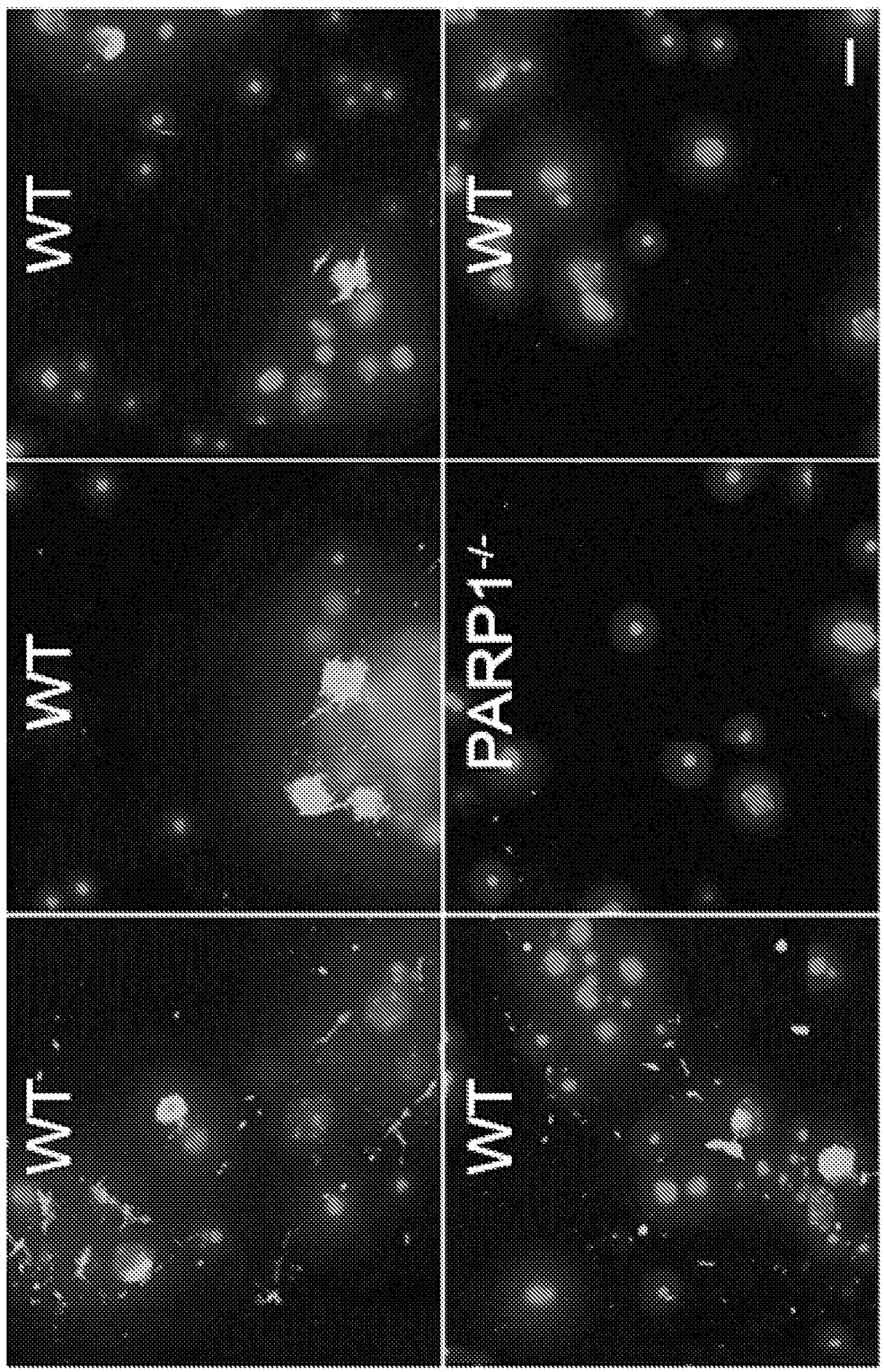
FIG. 50 shows the p-α-syn signal in high resolution images. Scale bar, 10 μm.
Figure 51:
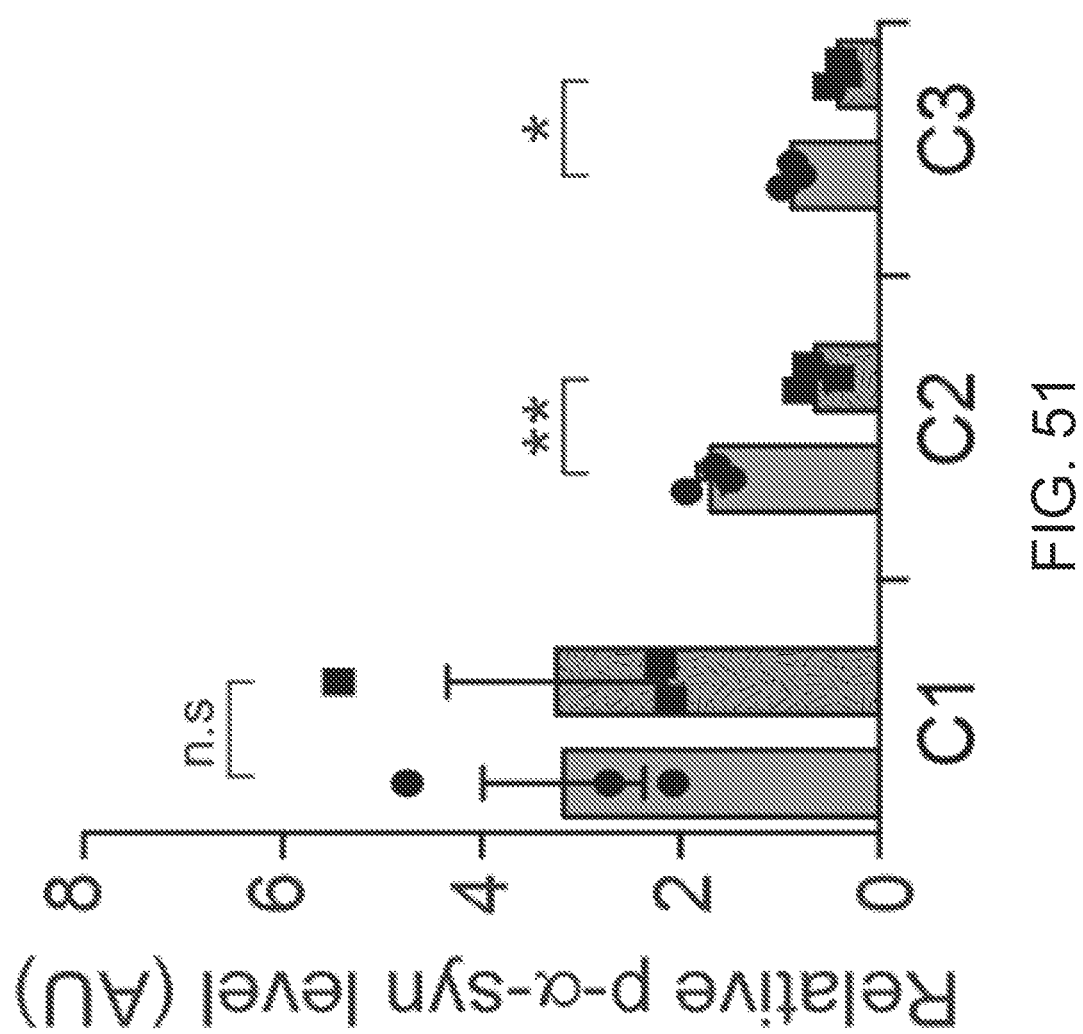
FIG. 51 shows quantification of p-α-syn levels in each chamber. Values are means s.e.m. Unpaired student's t test (n=3). *$P<0.05$, **$P<0.005$.

To determine whether α-syn PFF induces the activation of PARP, levels of PAR are measured using a highly sensitive and specific PAR monoclonal antibody after administration of α-syn PFF to primary mouse cortical neurons (FIGS. 5 to 12). α-syn PFF (1 μg/ml) induced PARP activation peaks between 3 to 7 days and remained elevated for up to 14 days (FIG. 5). Accompanying the elevation of PAR is the death of neurons as assessed by propidium iodide (PI) staining (FIGS. 6 and 7). Treatment of cortical neurons with the PARP inhibitors, ABT-888 (veliparib) (10 μM), or AG-014699 (Rucaparib) (1 μM) or BMN 673 (Talazoparib) (10 μM) prevents the α-syn PFF-mediated PARP activation and cell death (FIGS. 6, 7, and 8). These PARP inhibitors also reduce α-syn PFF-mediated phosphorylation of α-syn at serine 129 (p-α-syn) as assessed by immunostaining (FIGS. 37 and 38), and α-syn aggregation as indicated by immunoblot analysis (FIGS. 39 and 40), both of which are associated with pathology in α-synucleinopathies. Since PARP-1 plays a major role in parthanatos, PARP-1 was deleted from cortical neurons using CRISPR/Cas9 via adeno associated virus (AAV) transduction carrying a guide RNA against PARP-1 (FIGS. 9. 10 and 41) or used cortical cultures from PARP-1 knockouts (FIGS. 11, 12, and 42 to 46). Deletion or knockout of PARP-1 prevents α-syn PFF-mediated PARP activation and cell death (FIGS. 9 to 12, 41 and 42). Knockout of PARP1 also reduces p-α-syn immunostaining and α-syn aggregation as indicated by immunoblot analysis (FIGS. 43 to 46). Treatment of cortical neurons with the broad spectrum caspase inhibitor Z-VAD-FMK (Z-VAD) partially reduces α-syn PFF toxicity. The necroptosis inhibitor Necrostatin-1 (Nec-1) and the autophagy inhibitor 3-Methyladenine (3-MA) had no effect, while the PARP inhibitor ABT-888 prevents α-syn PFF toxicity (FIGS. 47 and 48). Since PARP inhibition and knockout of PARP-1 reduces the accumulation of pathologic α-syn as indicated by a reduction of p-α-syn immunostaining, cell-to-cell transmission of α-syn was assessed as previously described. Knockout of PARP-1 reduces the cell-to-cell transmission of pathologic α-syn (FIGS. 49 to 51). These results taken together suggest that α-syn PFF primarily kills neurons through parthanatos and that PARP-1 contributes to generation of pathologic α-syn.

Figure 13:
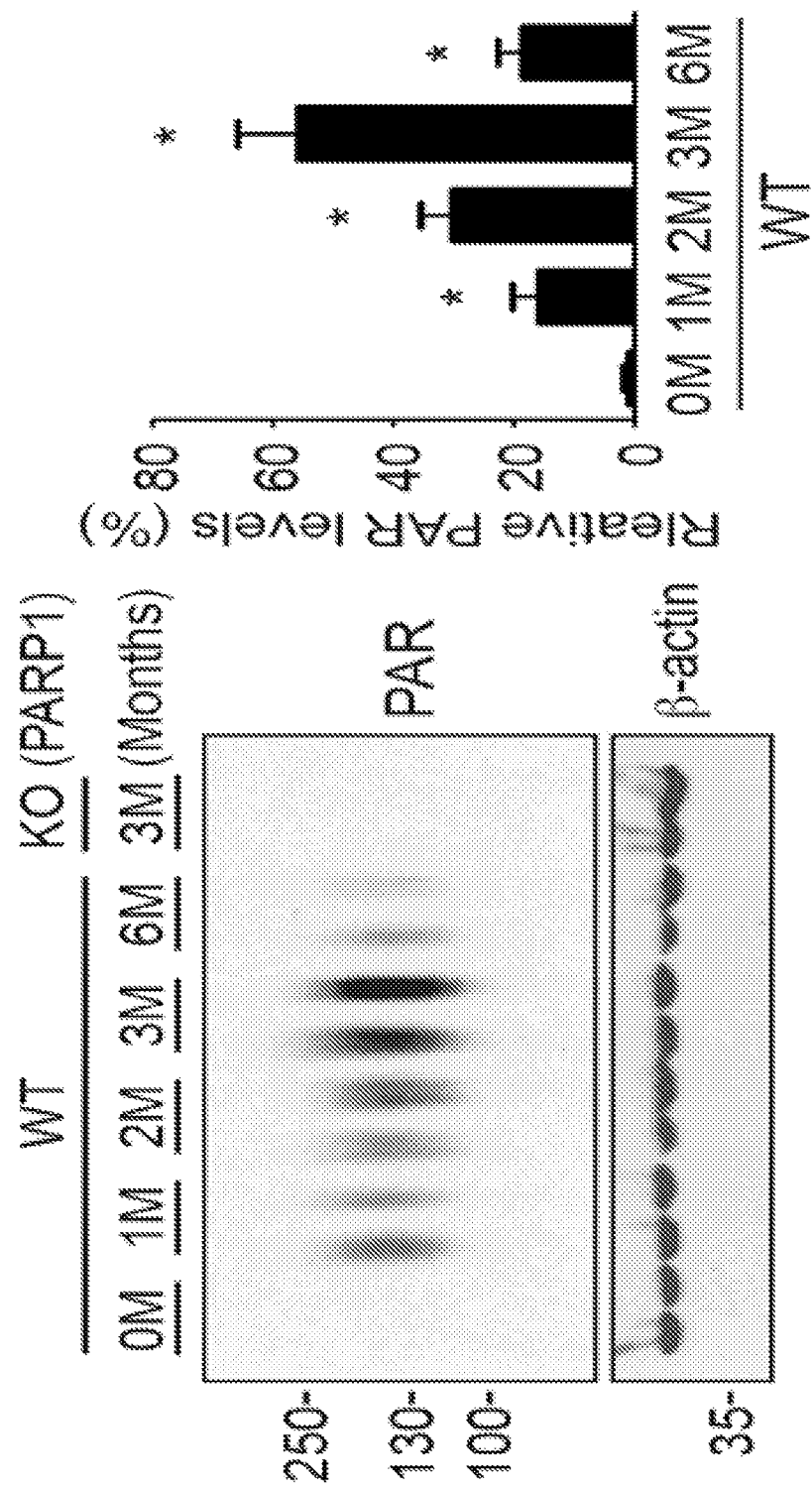
FIG. 13 shows representative immunoblots and quantification of the levels of PAR accumulation in the striatum of α-syn PFF injected mice. Bars represent mean±s.e.m. One-way ANOVA followed by Tukey's post hoc test (n=4).
Figure 14:
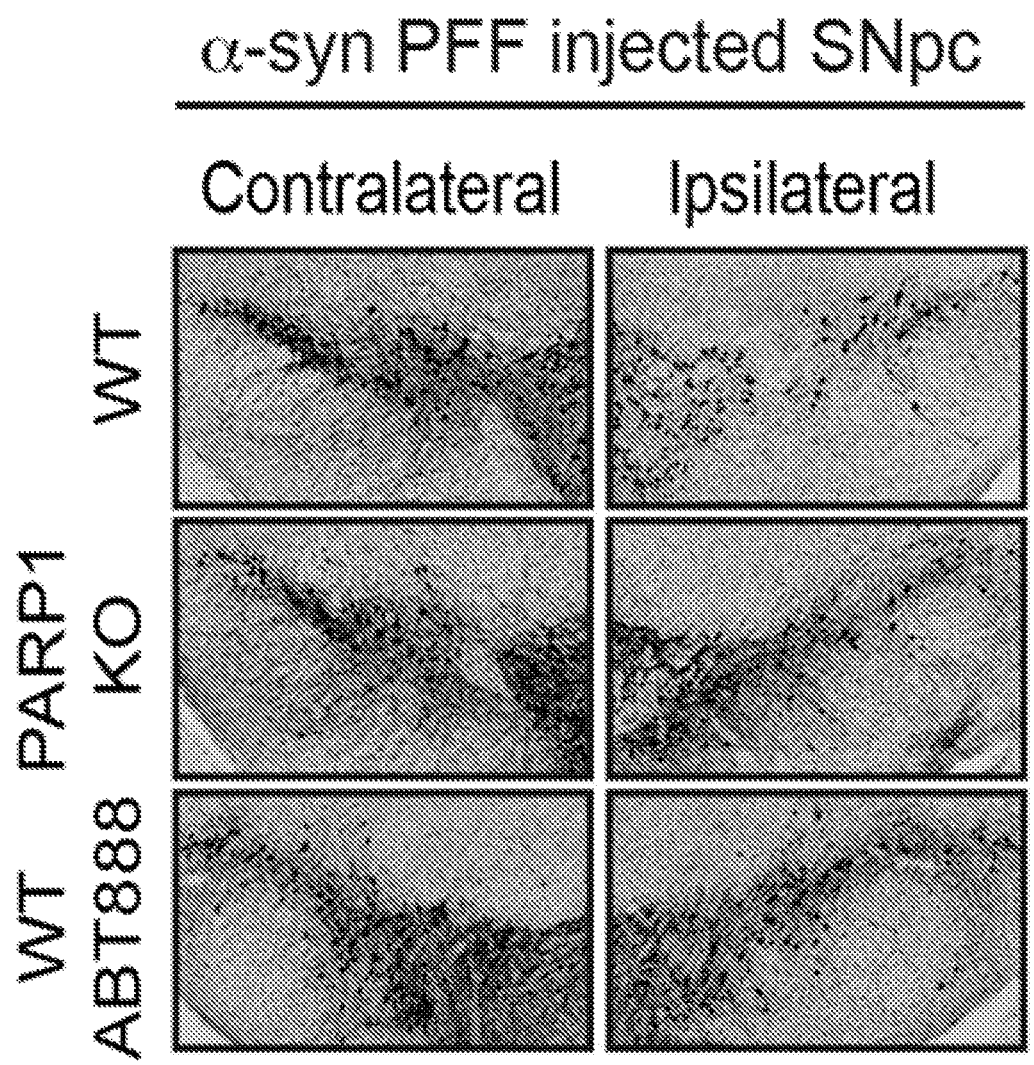
FIG. 14 shows representative TH and Nissl staining of SNpc DA neurons of α-syn PFF injected WT, PARP-1KO, and WT mice fed with ABT-888 at 6 months after intrastriatal α-syn PFF or PBS injection.
Figure 15:
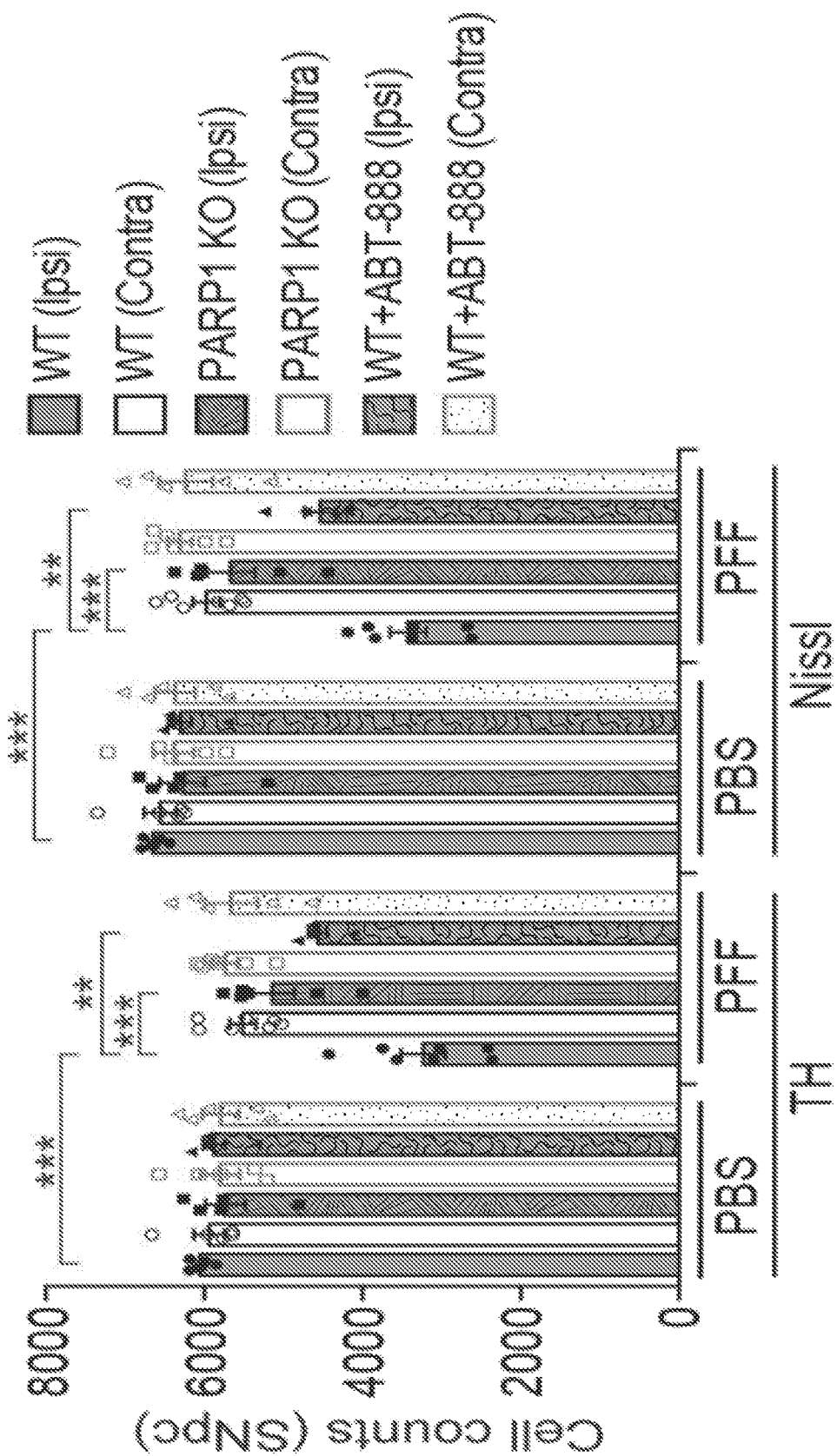
FIG. 15 shows stereological counts. Data are mean±s.e.m. One-way ANOVA followed by Tukey's post hoc test (n=5 to 7 mice per group).
Figure 16:
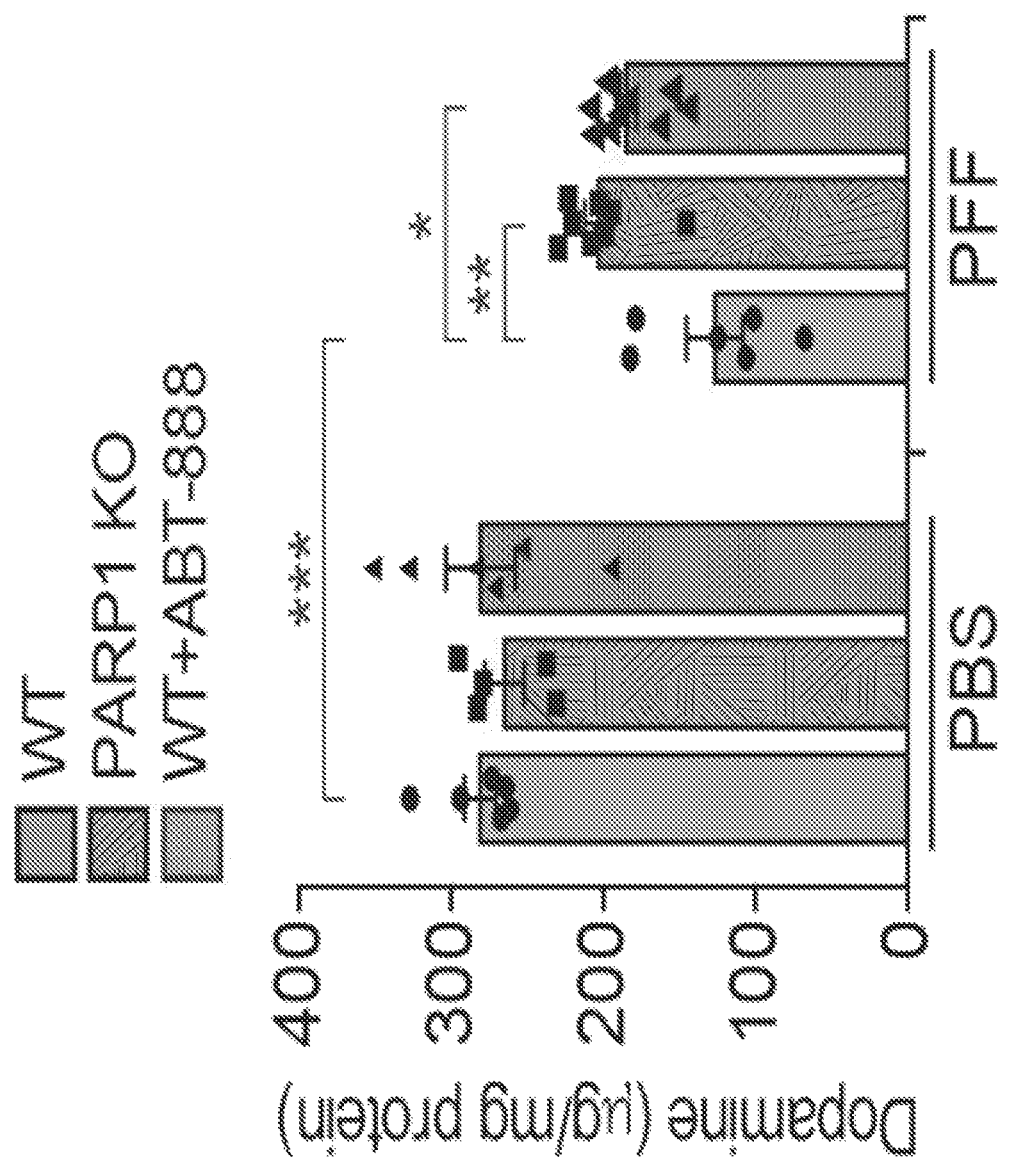
FIG. 16 shows DA concentrations in the striatum of WT, PARP-1 KO, and WT mice fed with ABT-888 at 6 months after intrastriatal α-syn PFF or PBS injection measured by HPLC. Bars represent mean±s.e.m. One-way ANOVA followed by Tukey's post hoc test. (n=6 to 30 mice per group).
Figure 17:
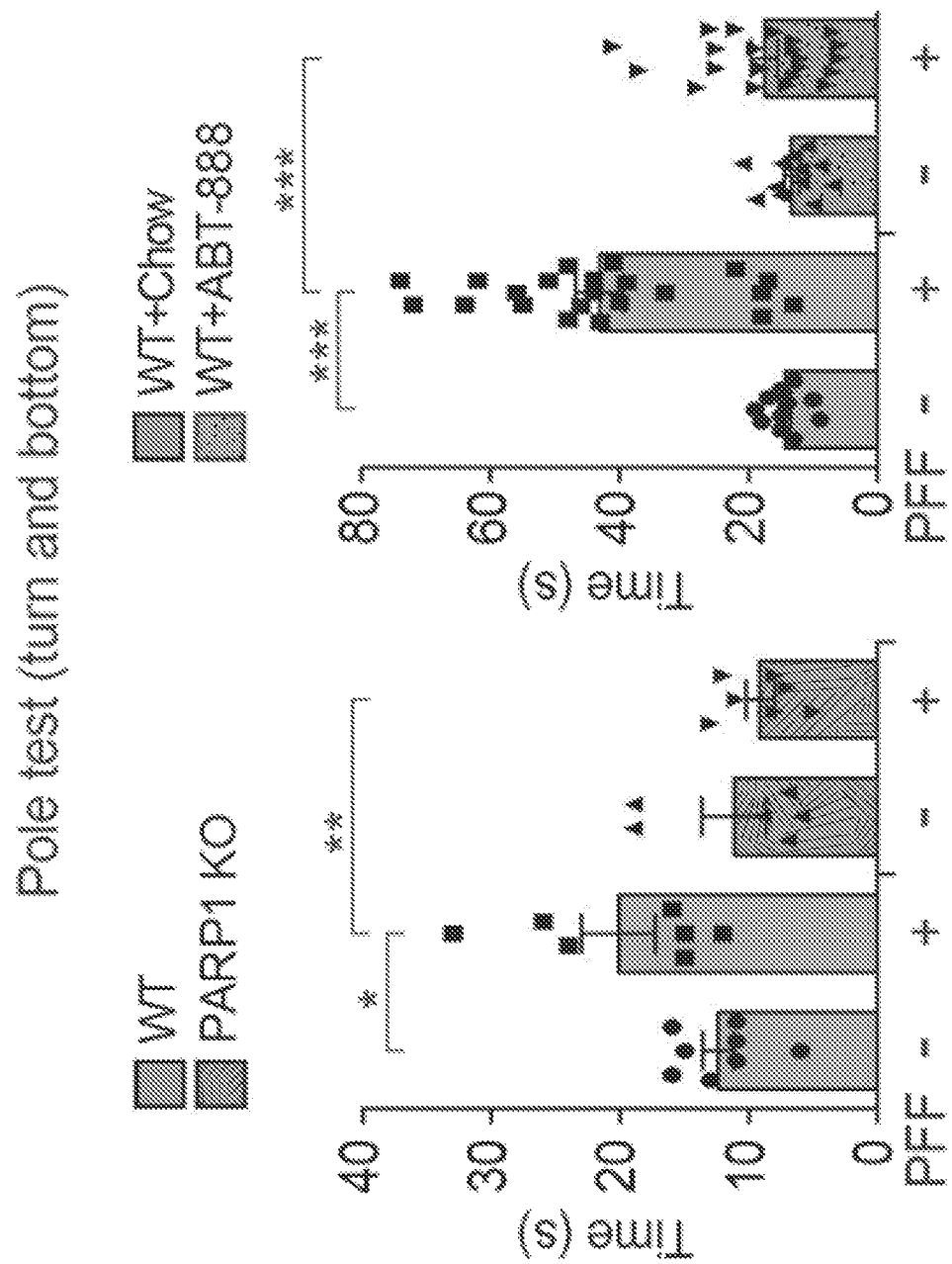
FIG. 17 shows pole test results 180 days after α-syn PFF injection. The pole test was performed in WT, PARP-1 KO, or WT mice fed with ABT-888. Data are the means s.e.m. One-way ANOVA followed by Tukey's post hoc test (n=7 to 9 mice per group). *P<0.05, P<0.005, *P<0.001.
Figure 18:
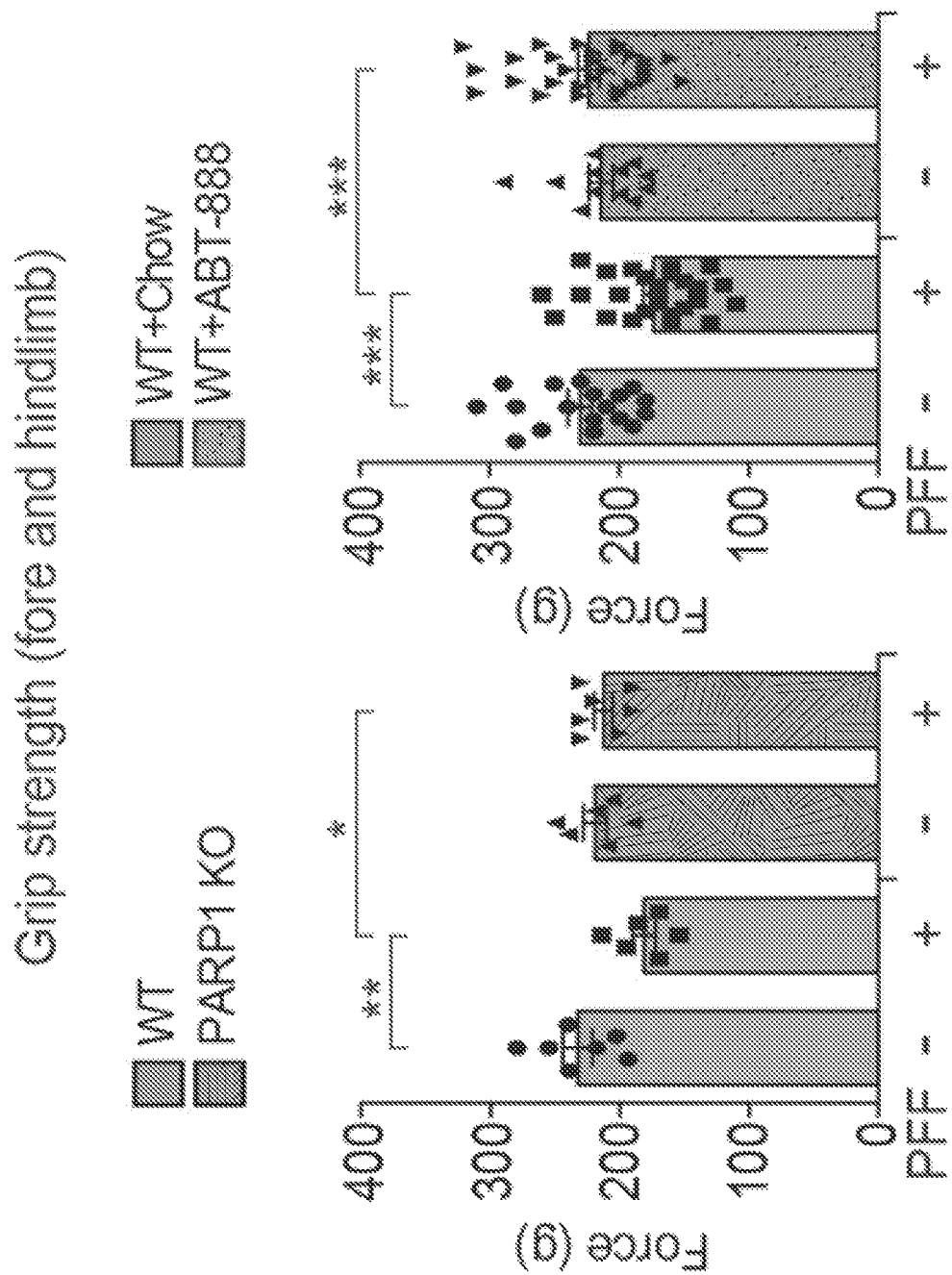
FIG. 18 shows grip strength results 180 days after α-syn PFF injection. The grip strength test was performed in WT, PARP-1 KO, or WT mice fed with ABT-888. Data are the means±s.e.m. One-way ANOVA followed by Tukey's post hoc test (n=7 to 9 mice per group). *P<0.05, P<0.005, *P<0.001.
Figure 52:
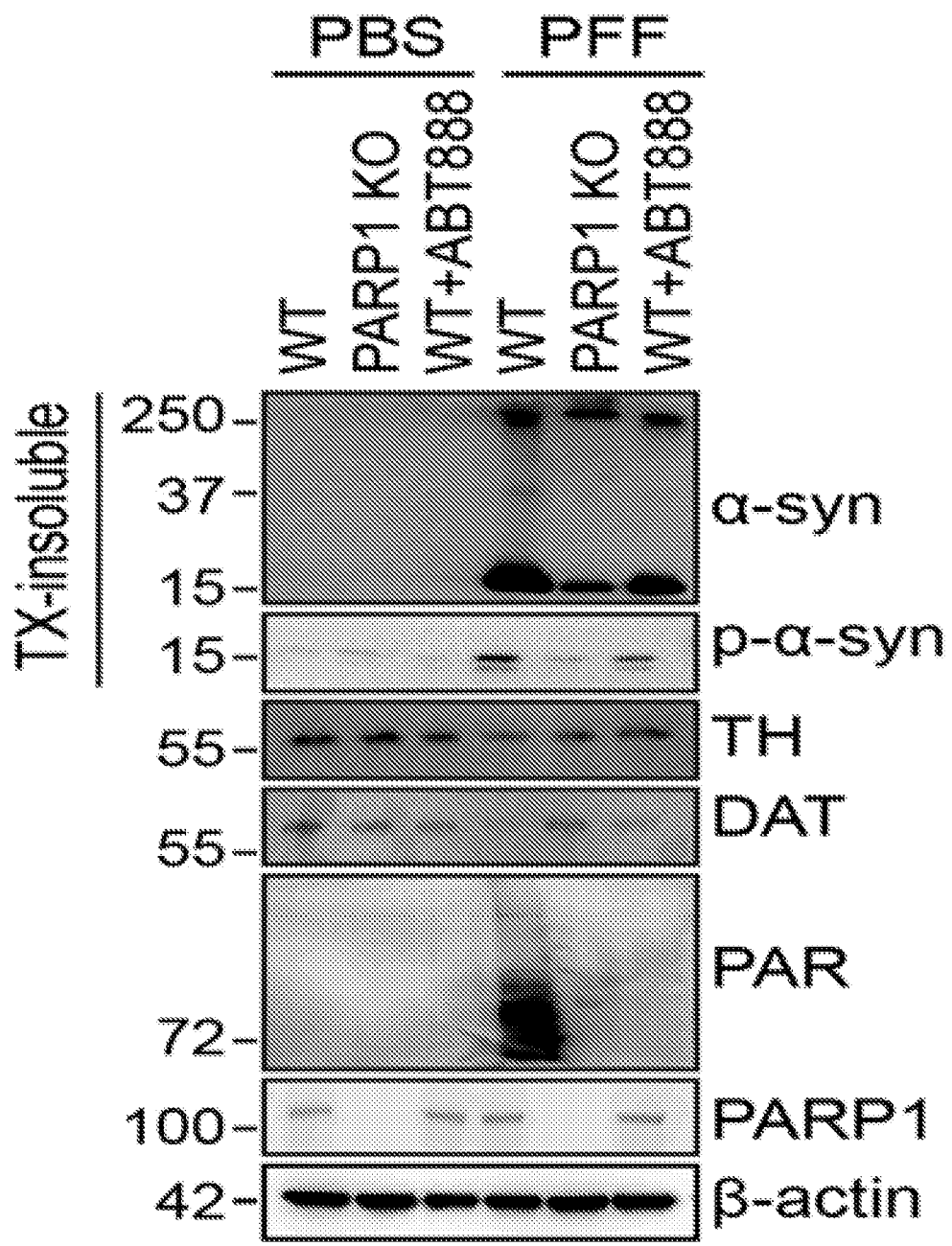
FIG. 52 shows representative immunoblots of the midbrain lysates from WT, PARP-1 KO, and WT mice fed with ABT-888 with misfolded α-syn, p-α-syn, TH, DAT, PAR, and PARP-1 antibodies.
Figure 53:
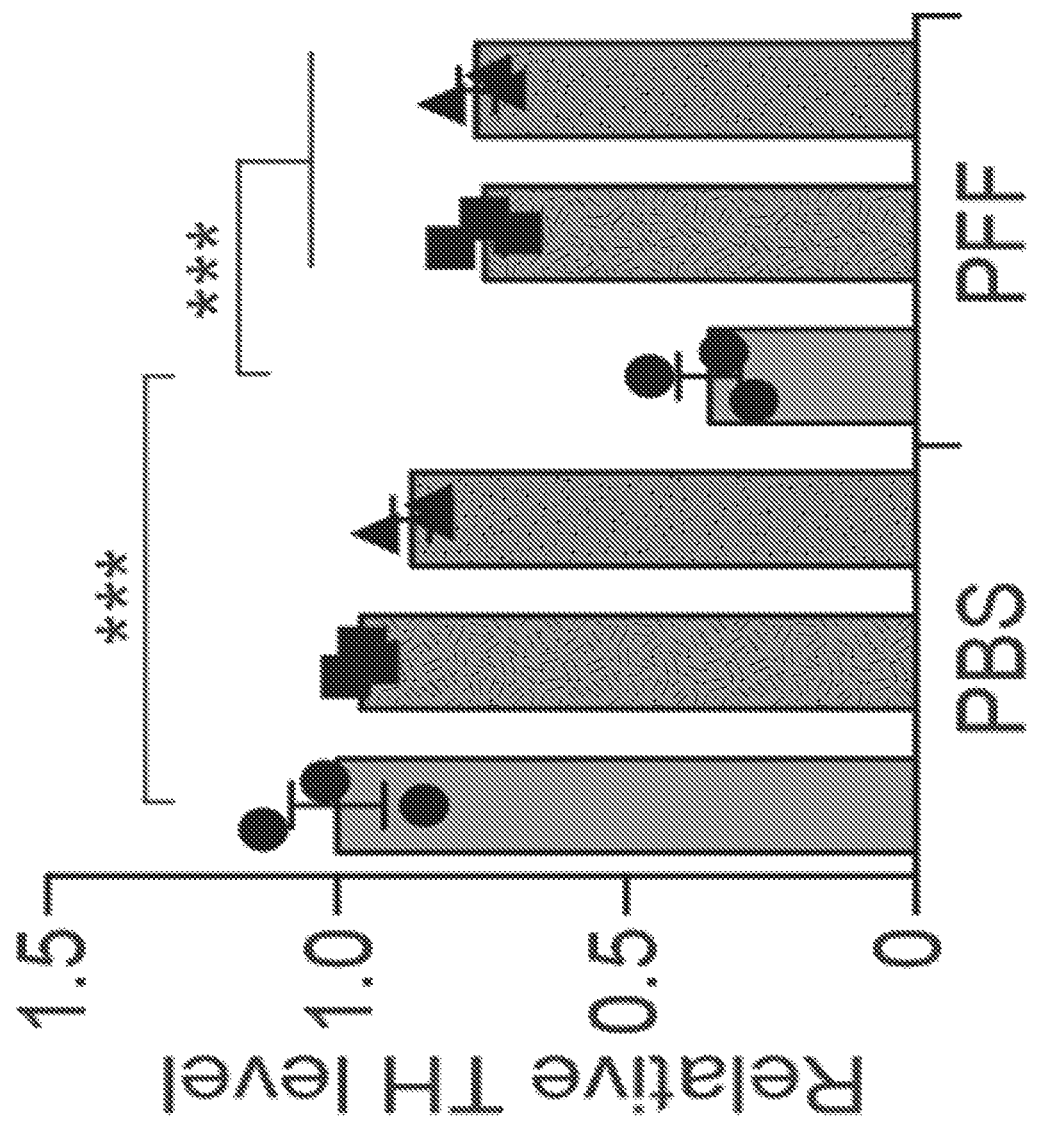
FIG. 53 shows quantification of TH levels. Bars represent mean±s.e.m. One-way ANOVA followed by Tukey's post hoc test (n=3). *$P<0.05$, $P<0.005$, *$P<0.001$.
Figure 54:
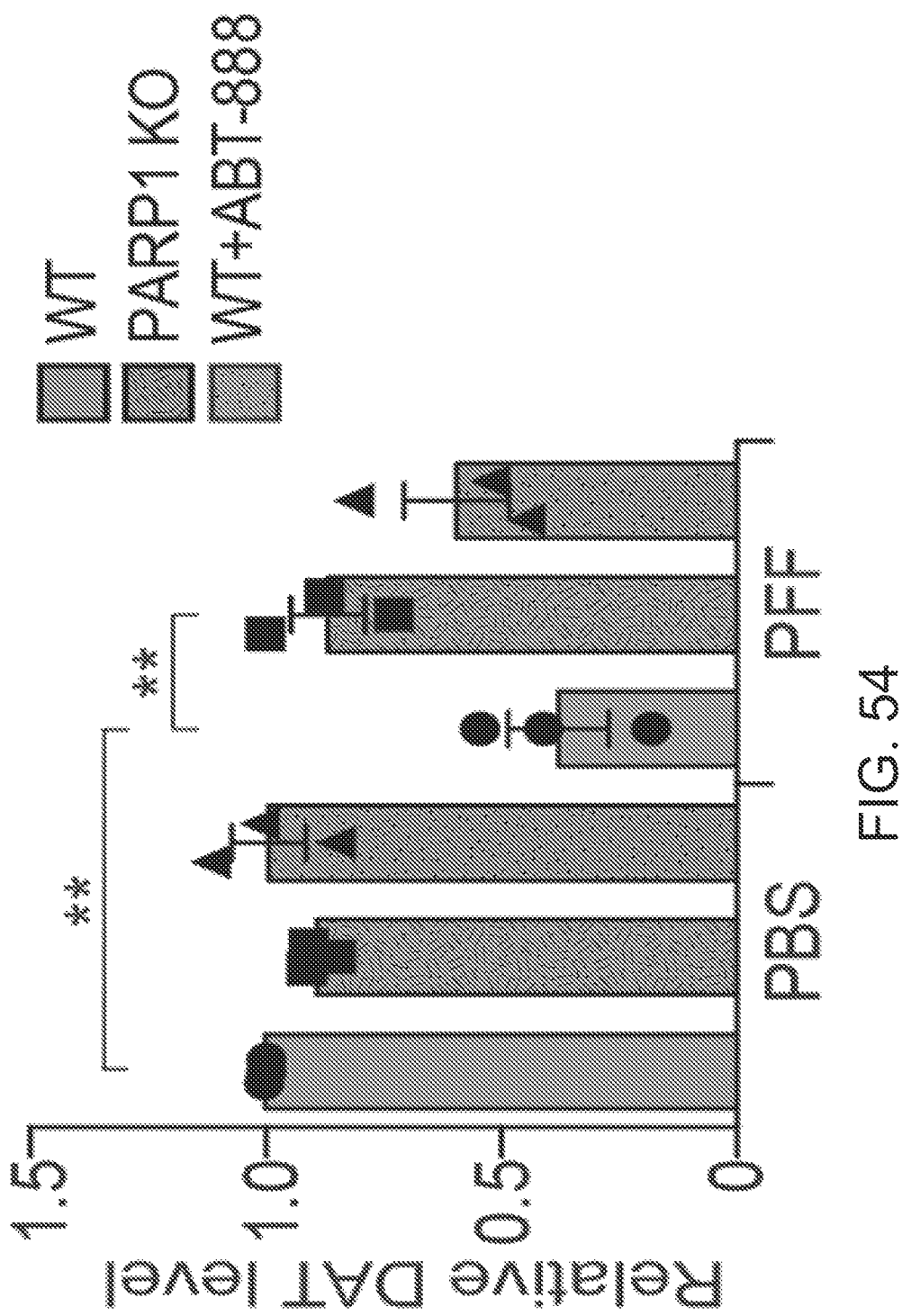
FIG. 54 shows quantification of DAT levels. Bars represent mean±s.e.m. One-way ANOVA followed by Tukey's post hoc test (n=3). *$P<0.05$, $P<0.005$, *$P<0.001$.
Figure 55:
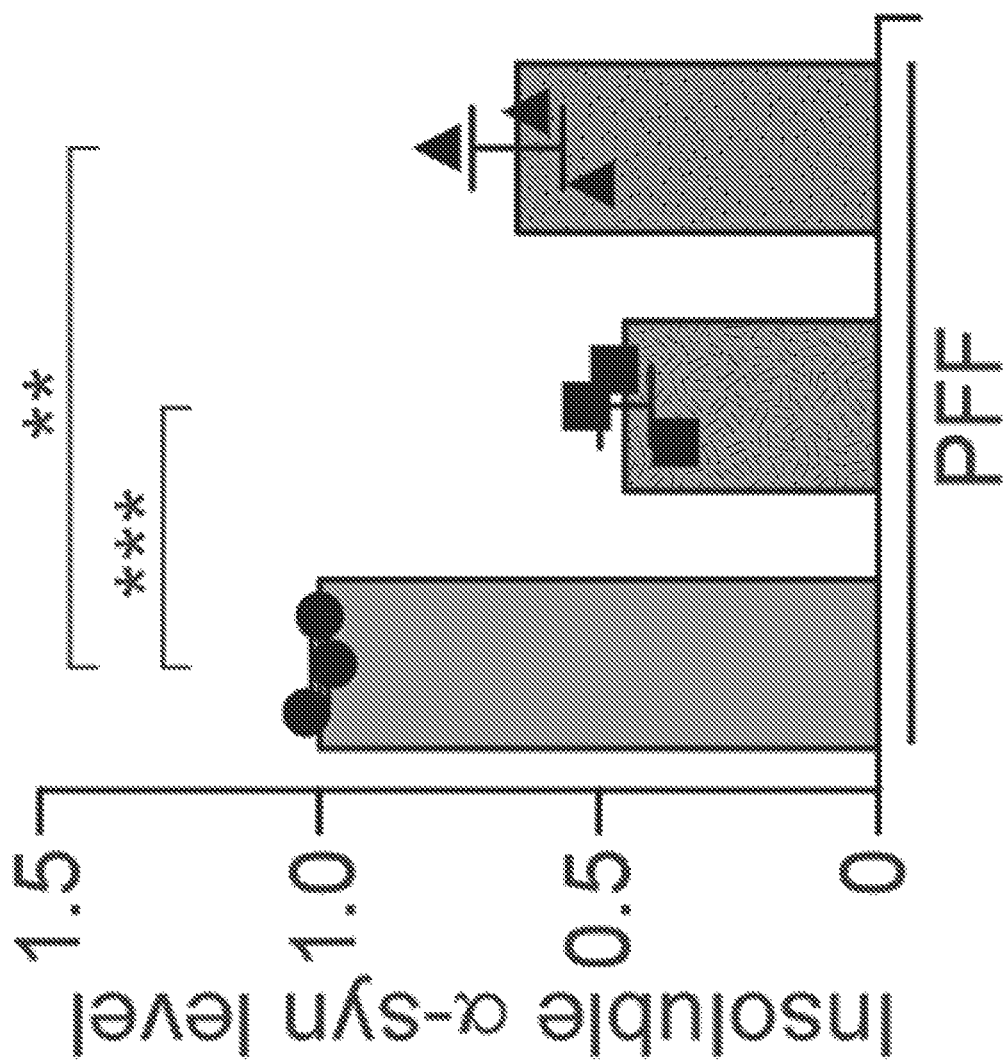
FIG. 55 shows quantification of insoluble α-syn levels. Bars represent mean±s.e.m. One-way ANOVA followed by Tukey's post hoc test (n=3). *$P<0.05$, $P<0.005$, *$P<0.001$.
Figure 56:
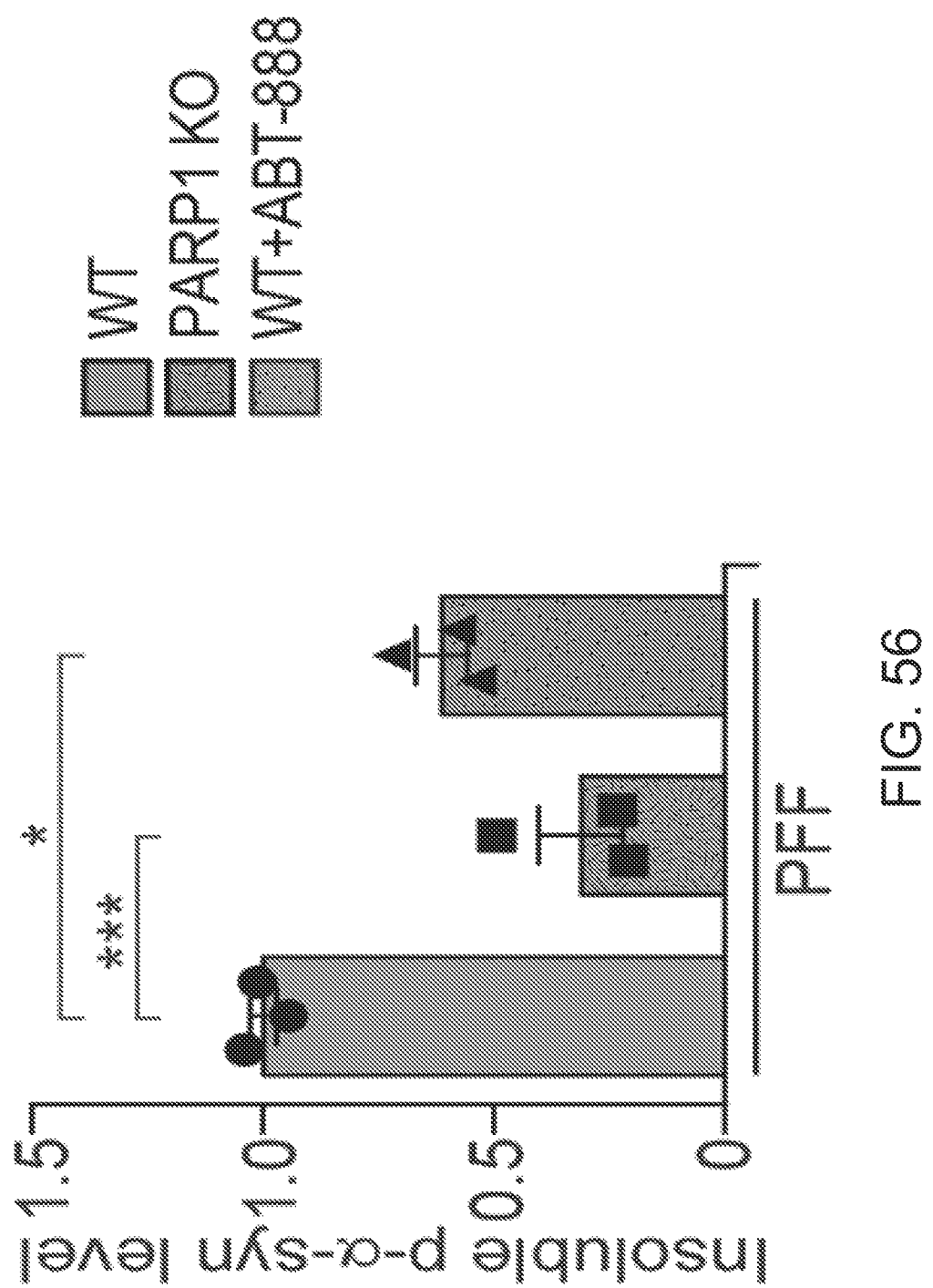
FIG. 56 shows quantification of insoluble p-α-syn levels. Bars represent mean±s.e.m. One-way ANOVA followed by Tukey's post hoc test (n=3). *$P<0.05$, $P<0.005$, *$P<0.001$.
Figure 57:
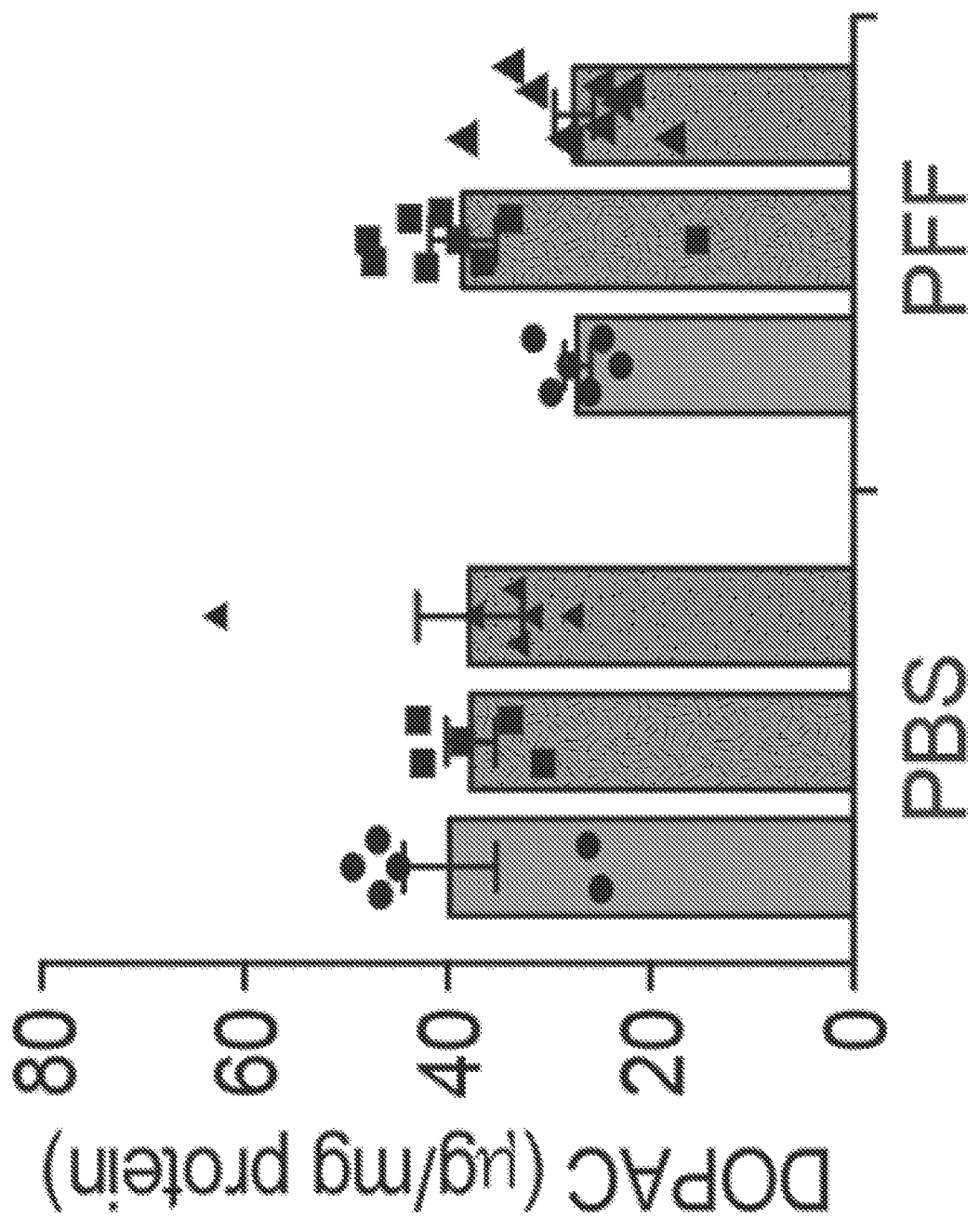
FIG. 57 shows DA metabolite DOPAC concentrations in the striatum of WT, PARP-1 KO, and WT mice fed with ABT-888 at 6 months after intrastriatal α-syn PFF or PBS injection measured by HPLC. Bars represent mean±s.e.m. One-way ANOVA followed by Tukey's post hoc test. (n=5 to 10 mice per group).
Figure 58:
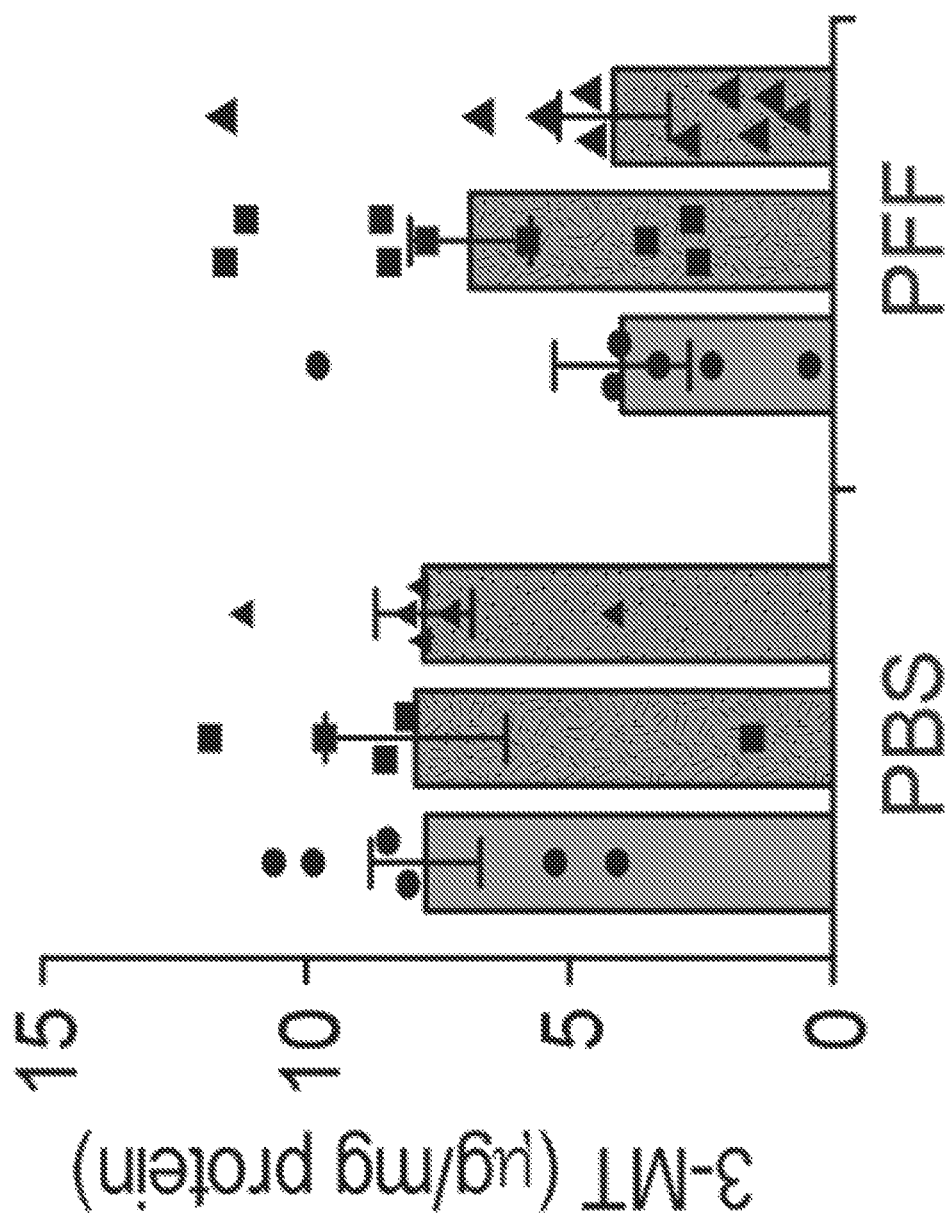
FIG. 58 shows DA metabolite 3-MT concentrations in the striatum of WT, PARP-1 KO, and WT mice fed with ABT-888 at 6 months after intrastriatal α-syn PFF or PBS injection measured by HPLC. Bars represent mean±s.e.m. One-way ANOVA followed by Tukey's post hoc test. (n=5 to 10 mice per group).
Figure 59:
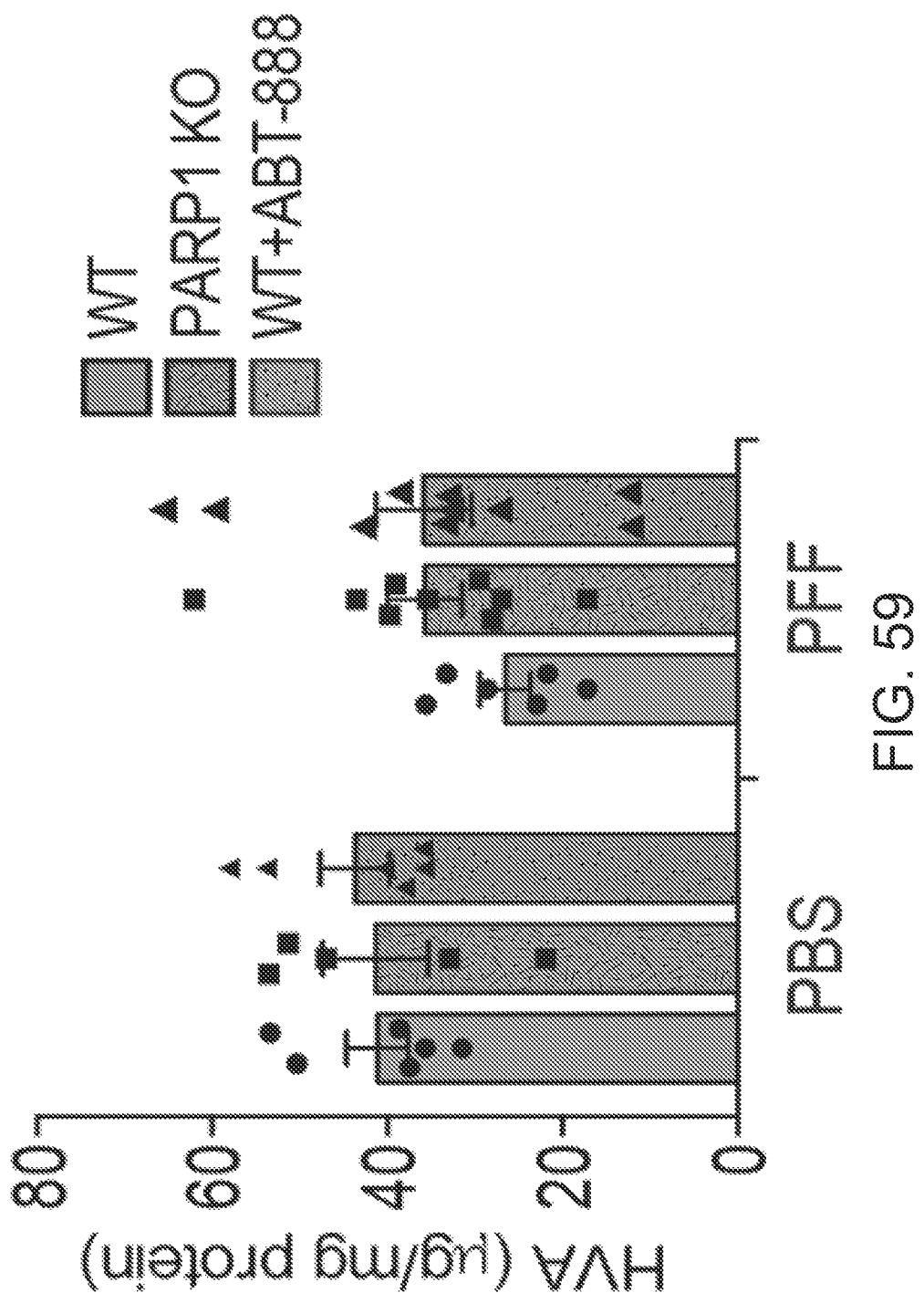
FIG. 59 shows DA metabolite HVA concentrations in the striatum of WT, PARP-1 KO, and WT mice fed with ABT-888 at 6 months after intrastriatal α-syn PFF or PBS injection measured by HPLC. Bars represent mean±s.e.m. One-way ANOVA followed by Tukey's post hoc test. (n=5 to 10 mice per group).
Figure 60:
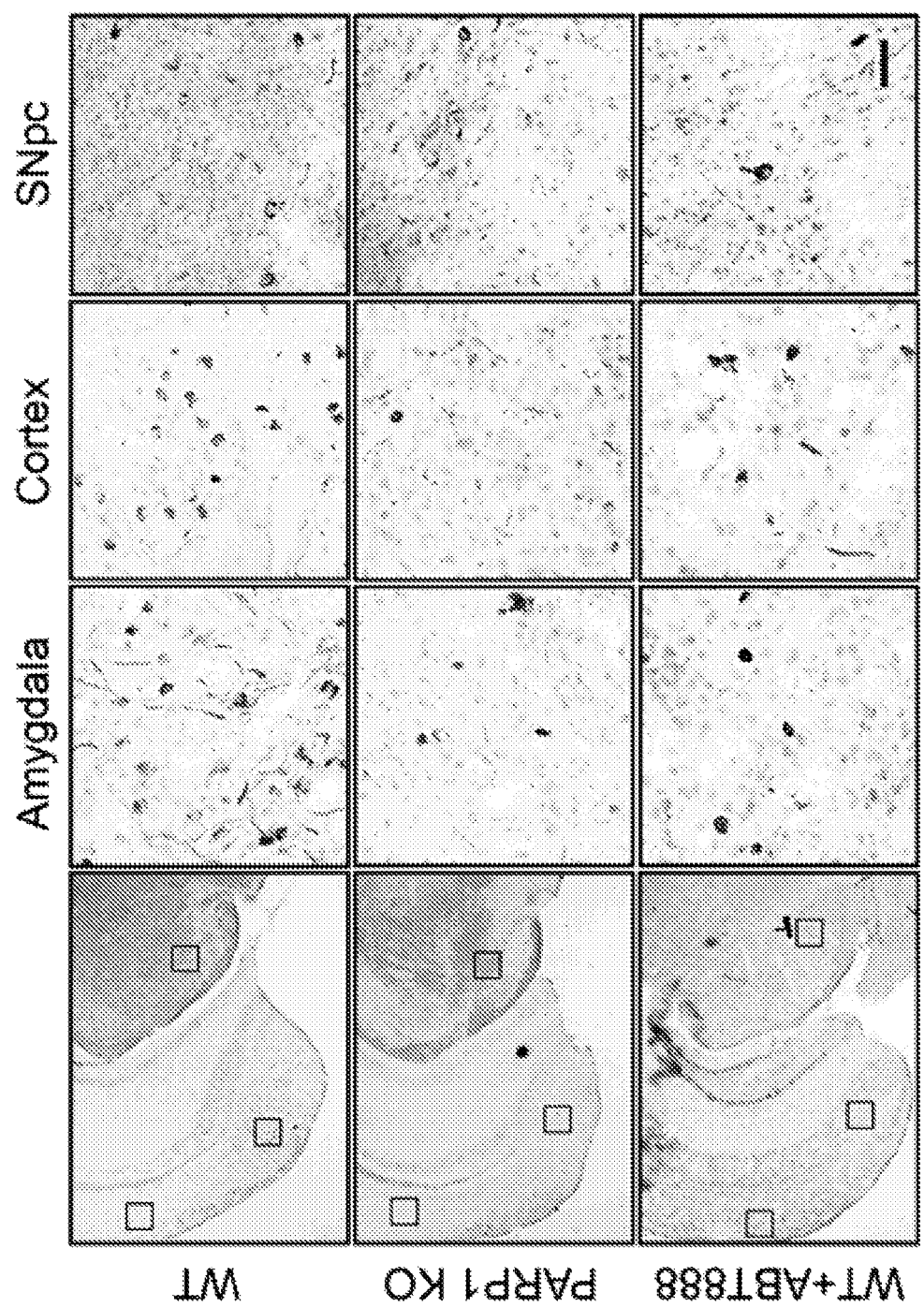
FIG. 60 shows representative images of p-α-syn immunostaining from WT, PARP-1 KO, and WT mice fed with ABT-888.
Figure 61:
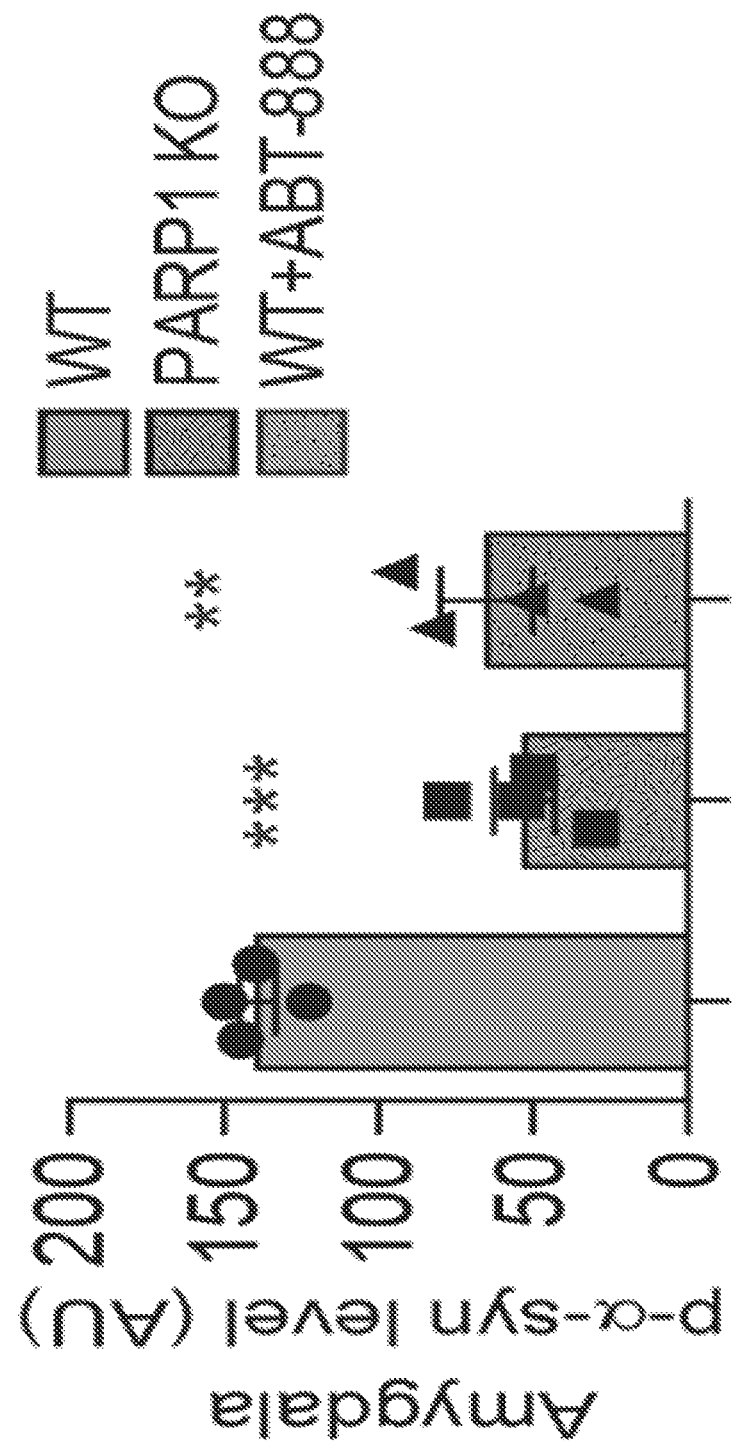
FIG. 61 shows quantification of p-α-syn intensity in amygdala region. Bars represent mean±s.e.m. One-way ANOVA followed by Tukey's post hoc test. (n=4 to 5 mice per group).
Figure 62:
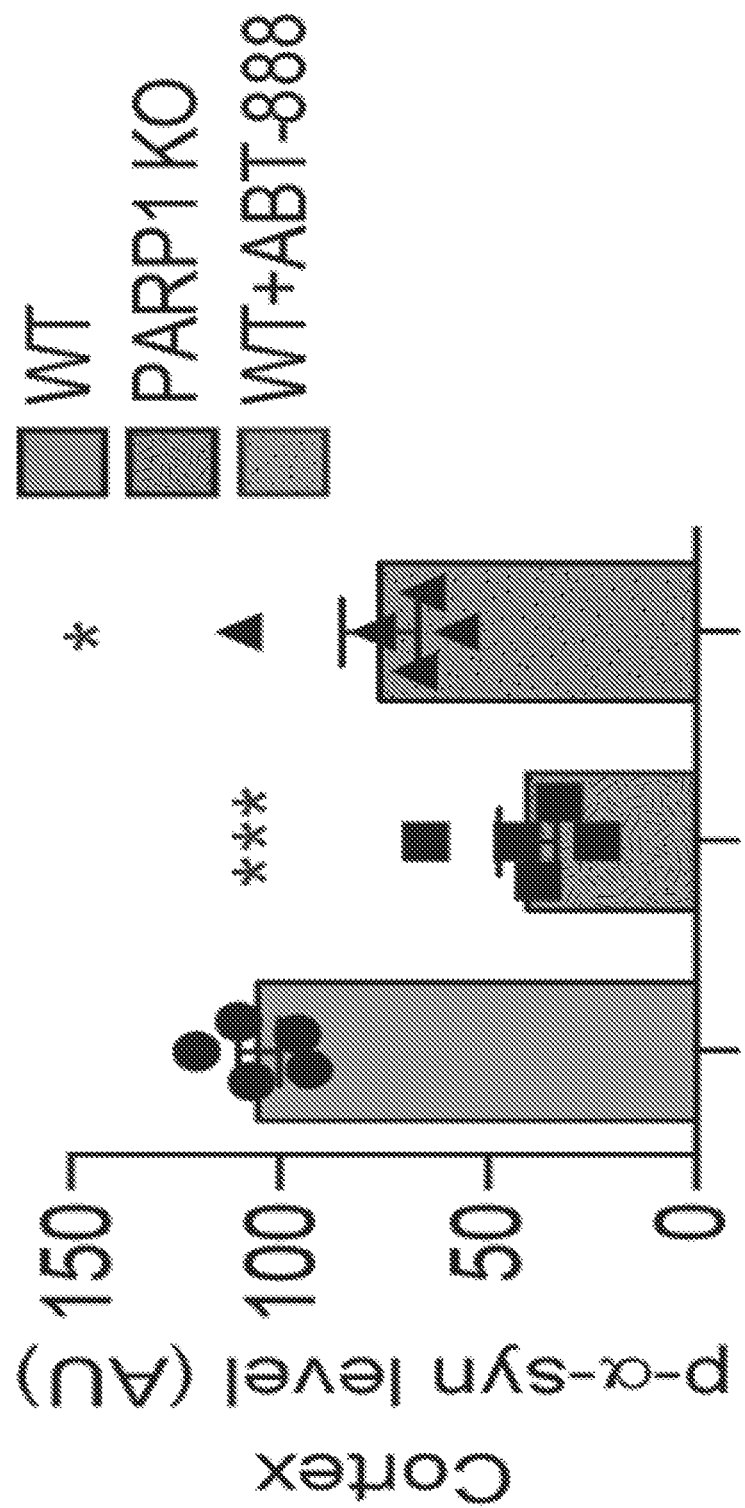
FIG. 62 shows quantification of p-α-syn intensity in cortex region. Bars represent mean±s.e.m. One-way ANOVA followed by Tukey's post hoc test. (n=4 to 5 mice per group).
Figure 63:
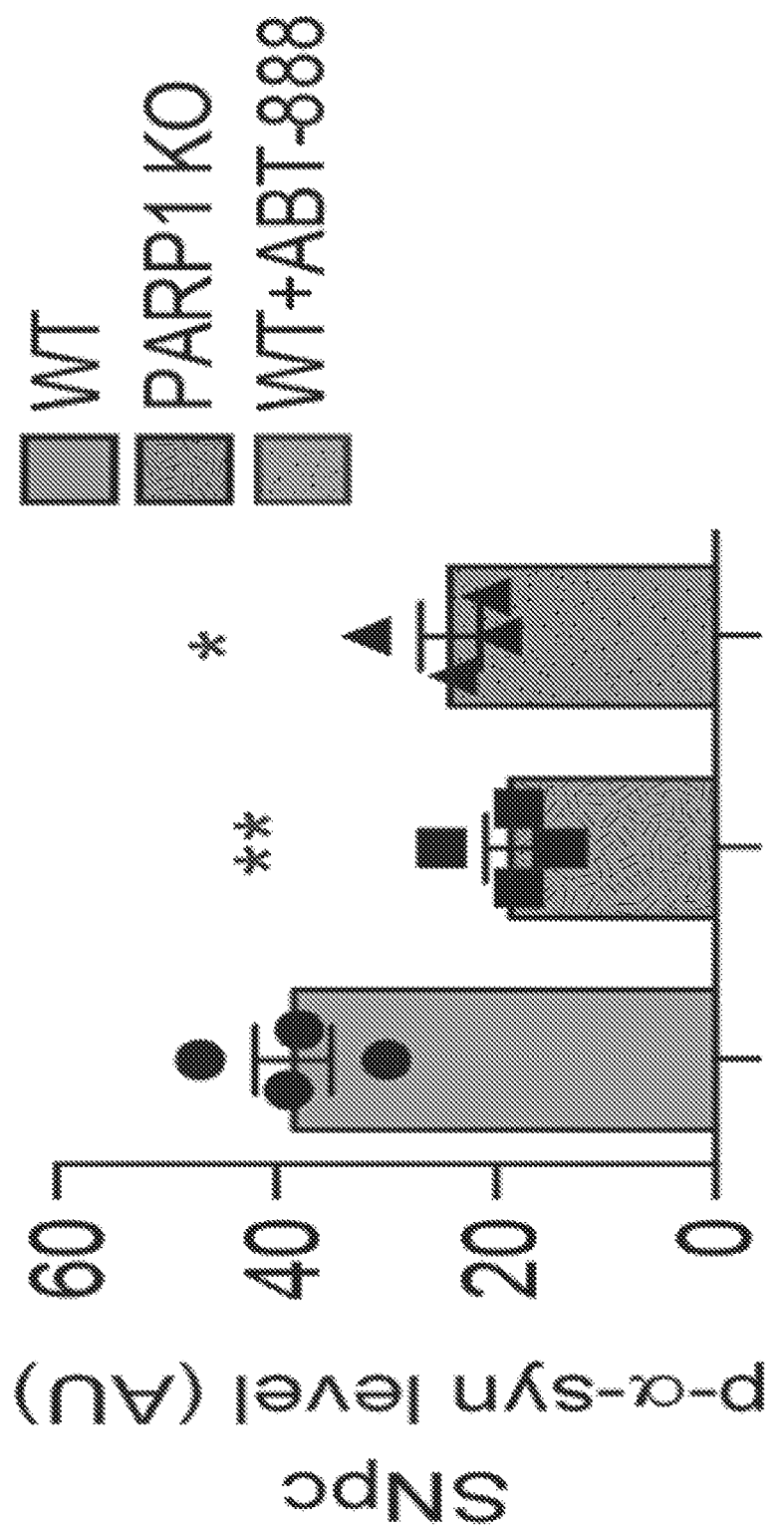
FIG. 63 shows quantification of p-α-syn intensity in SNpc region. Bars represent mean±s.e.m. One-way ANOVA followed by Tukey's post hoc test. (n=4 to 5 mice per group).
Figure 64:
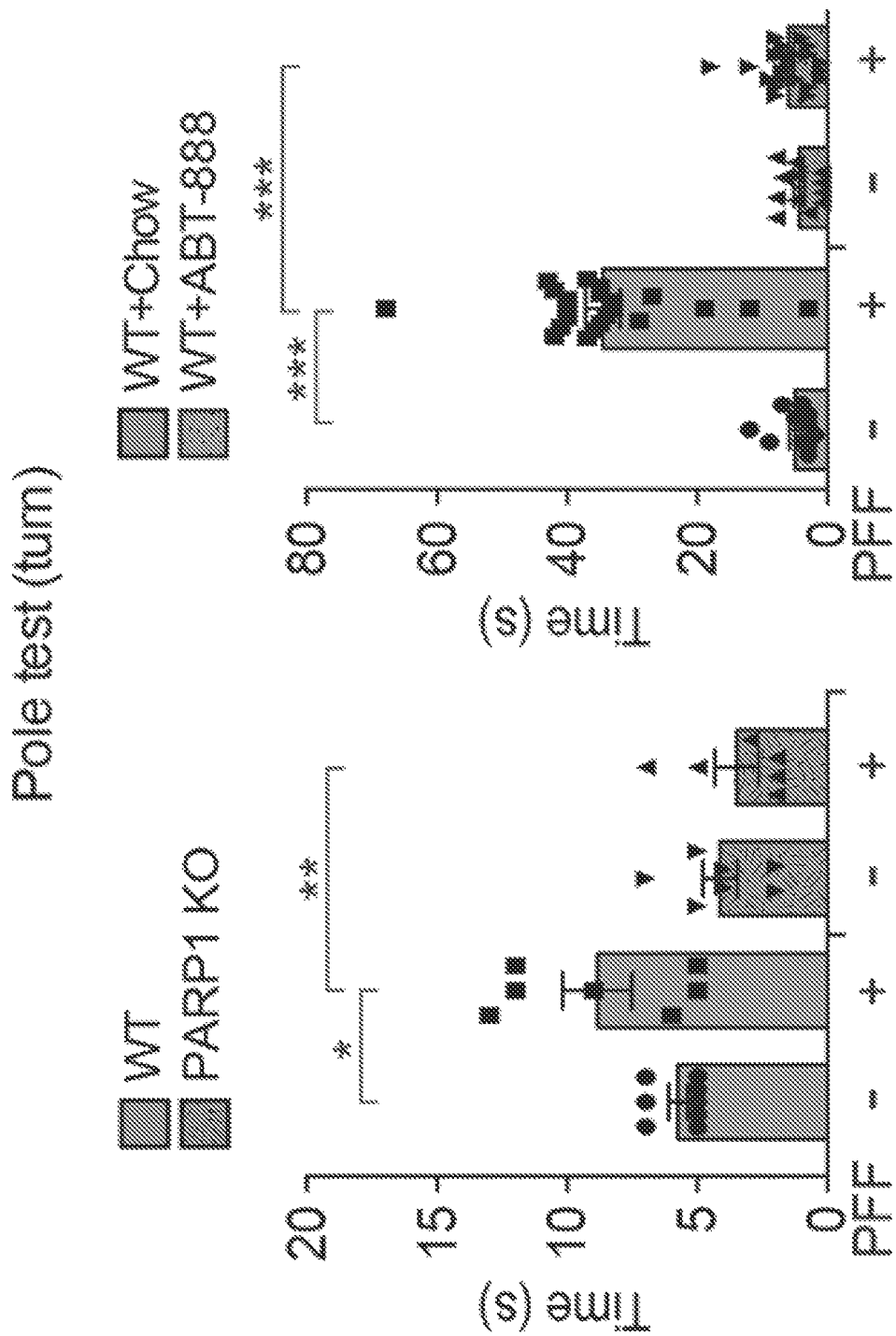
FIG. 64 shows pole test results 180 days after α-syn PFF injection. The pole test was performed in WT, PARP-1 KO, or WT mice fed with ABT-888. Data are the means s.e.m. One-way ANOVA followed by Tukey's post hoc test (n=6 to 30 mice per group). *$P<0.05$, $P<0.005$, *$P<0.001$.
Figure 65:
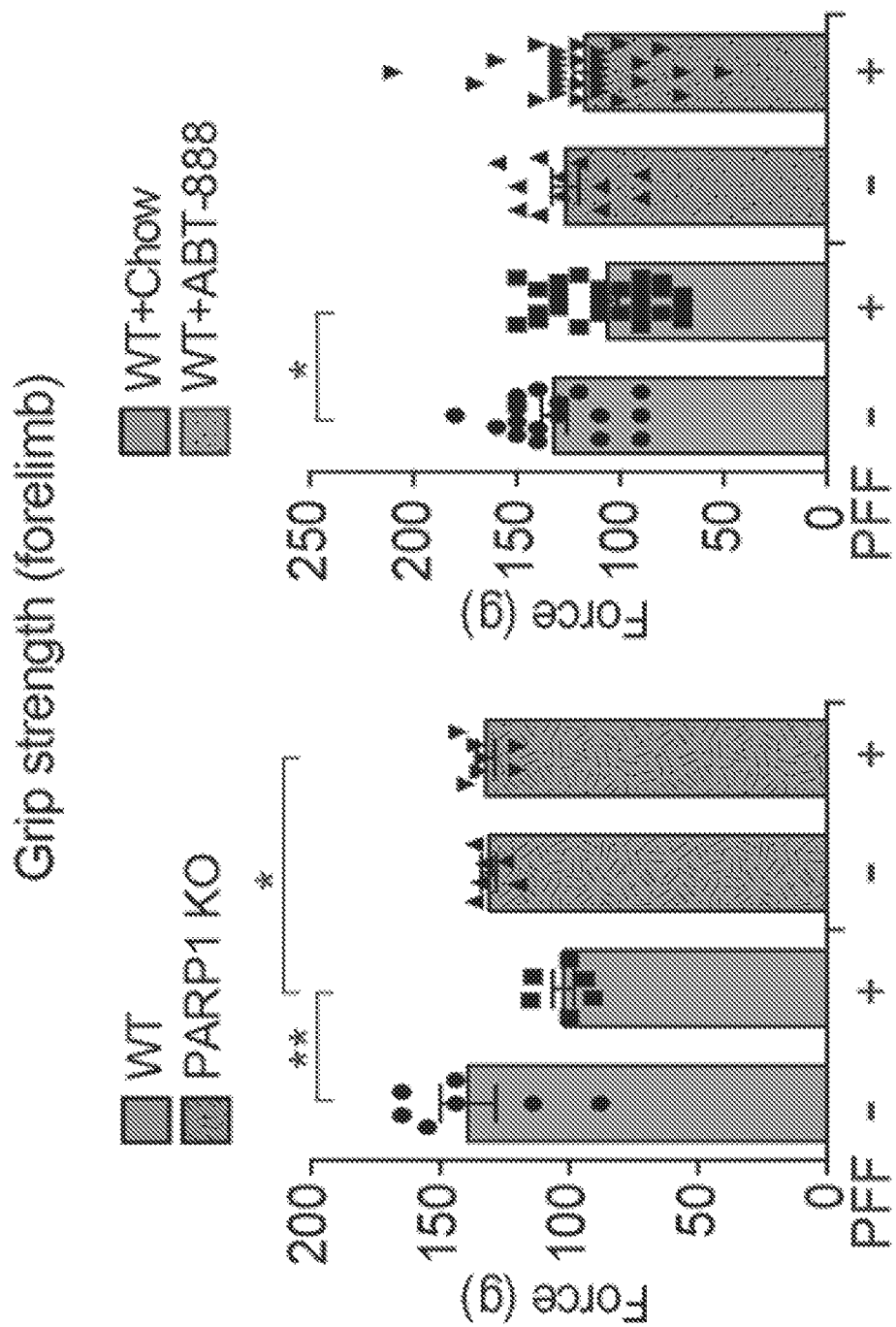
FIG. 65 shows grip strength test results 180 days after α-syn PFF injection. The grip strength test was performed in WT, PARP-1 KO, or WT mice fed with ABT-888. Data are the means±s.e.m. One-way ANOVA followed by Tukey's post hoc test (n=6 to 30 mice per group). *$P<0.05$, $P<0.005$, *$P<0.001$.

Since synthetic α-syn PFF kill primary cortical neurons via parthanatos, experiments were done to determine if parthanatos plays a role in the loss of DA neurons following the intrastriatal injection of α-syn PFF using a standard and validated protocol (FIGS. 13 to 18). A single intrastriatal injection of α-syn PFF (5 µg) induces PARP activation as determined by assessing PAR levels (FIG. 13). Intrastriatal injection of α-syn PFF into PARP-1 knockout mice fails to increase PAR levels (FIG. 13). A single intrastriatal injection of α-syn PFF leads to an approximate 50% loss of DA neurons 6 months following the injection in WT mice (FIGS. 14 and 15). In contrast, a single intrastriatal injection of α-syn PFF into PARP-1 knockout mice fails to induce DA cell loss (FIGS. 14 and 15). WT mice were also fed a diet containing the PARP inhibitor ABT-888 (125 mg/kg) and compared with mice given a control diet (FIGS. 14 and 15). Mice treated with ABT-888 exhibit significantly less loss of DA neurons after an intrastriatal injection of α-syn PFF compared to mice on the control diet (FIGS. 14 and 15). ABT-888 also reduces the formation of α-syn PFF induced increase in PAR levels (FIG. 52). Tyrosine hydroxylase (TH) and dopamine transporter (DAT) levels are also reduced in WT mice in response to α-syn PFF as determined by western blot analysis, while the reduction in TH and DAT levels is prevented in PARP-1 knockout more or ABT-888 treated ST mice (FIGS. 52 to 54). Accompanying the loss of DA neurons is a reduction in striatal DA and its metabolites as determined by HPLC in WT mice, but not PARP-1 knockout mice or ABT-888 treated mice (FIGS. 16, 57, 58 and 59). An injection of intrastriatal α-syn PFF leads to α-syn pathology as assessed by western blotting (FIGS. 52, 55 and 56) and immunostaining for p-α-syn in DA neurons of WT mice (FIGS. 60 to 63). α-syn pathology is markedly reduced in PARP-1 knockout mice and ABT-888 treated WT mice consistent with the absence and reduction of neurodegeneration, respectively. Intrastriatal injection of α-syn PFF causes deficits on the pole test, a sensitive behavioral measurement of dopaminergic function in WT mice, whereas there are no deficits in PARP-1 knockout mice and ABT-888 WT treated mice (FIGS. 17 and 64). Both forelimb plus hindlimb and forelimb grip strength are also reduced in WT mice after α-syn PFF injection, but not in PARP-1 knockout or ABT-888 treated WT mice (FIGS. 18 and 65). Taken together, these results indicate that the striatal α-syn PFF-induced loss of DA neurons is dependent on PARP-1.

Figure 19:
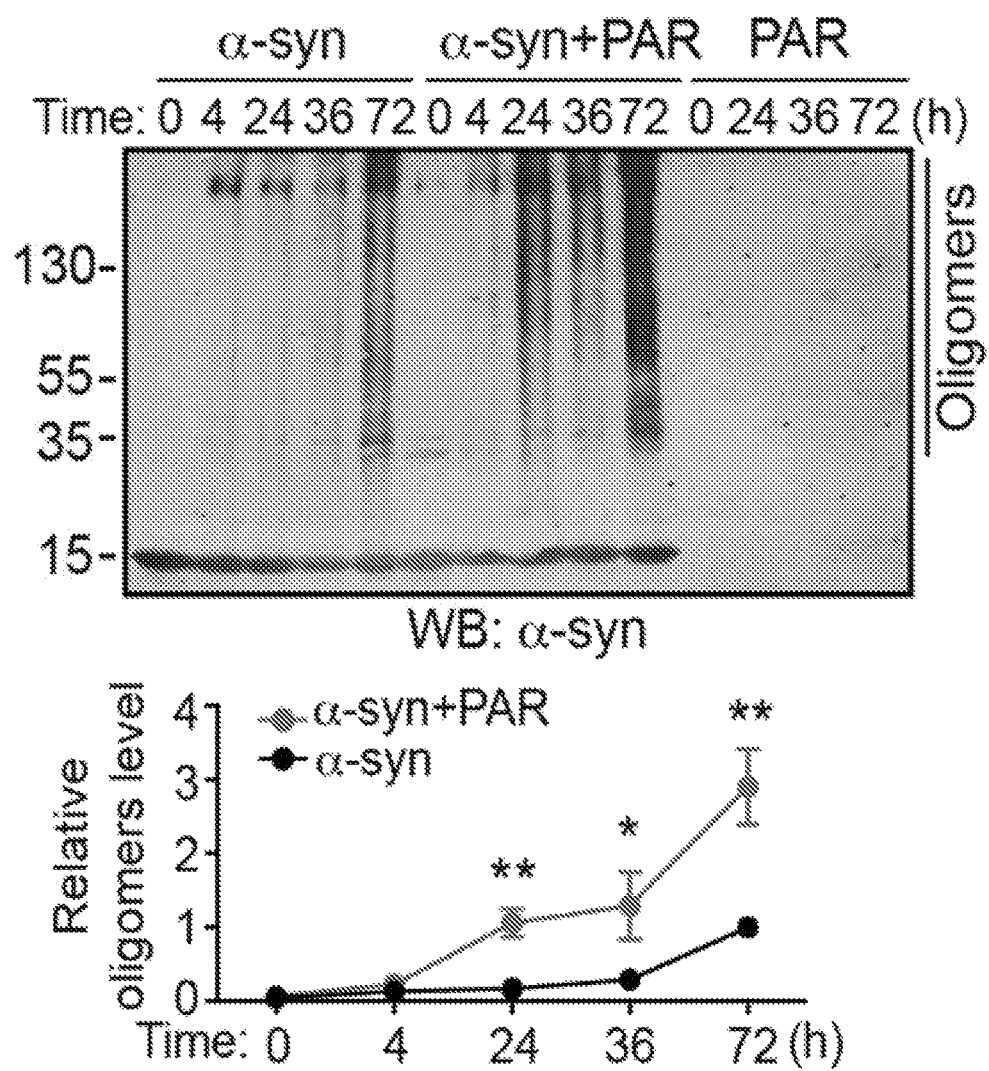
FIG. 19 shows acceleration of α-syn fibrillization by PAR. Monomeric α-syn either with or without 5 nM purified PAR was incubated at 37° C. for indicated times. Fibrillization of α-syn was detected by immunoblotting using α-syn antibody (top). Data are mean±s.e.m. (bottom). One-way ANOVA followed by Tukey's post hoc test (n=3).
Figure 20:
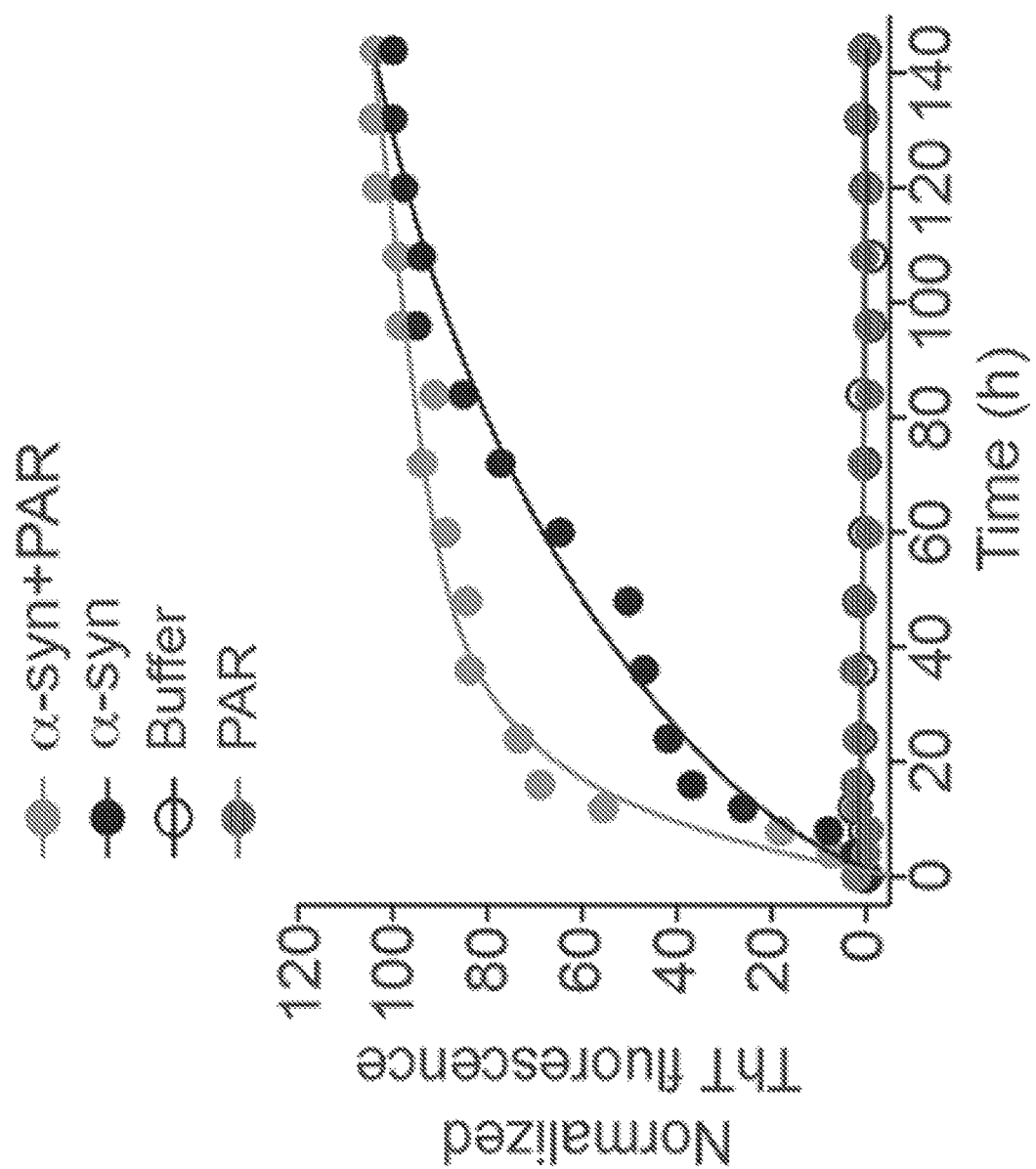
FIG. 20 shows the rate of formation of α-syn fibrils either with or without PAR was monitored by thioflavin T fluorescence (n=3).
Figure 21:
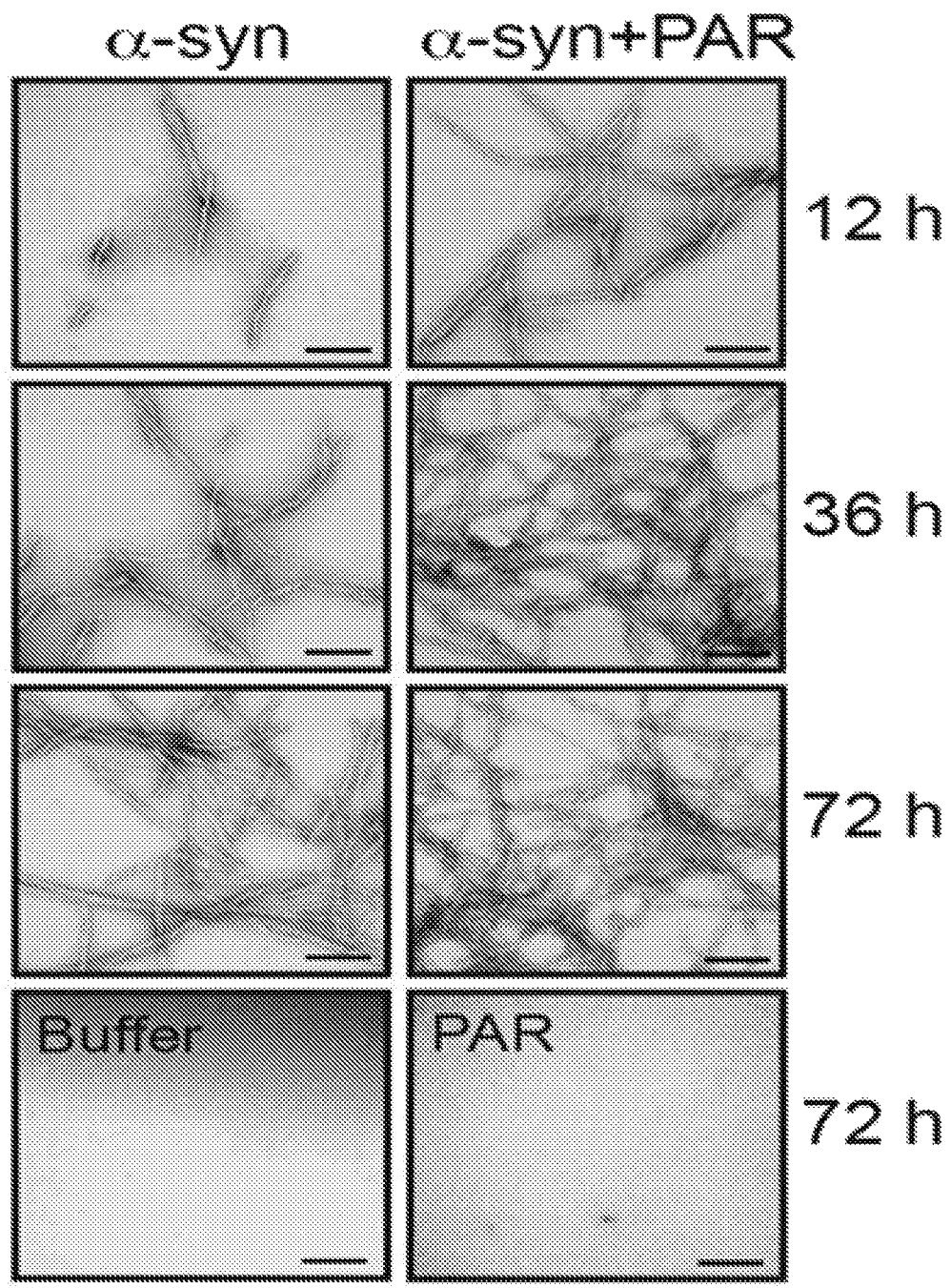
FIG. 21 shows representative transmission electron microscopy (TEM) images for α-syn fibrils. Scale bar, 200 nm.
Figure 22:
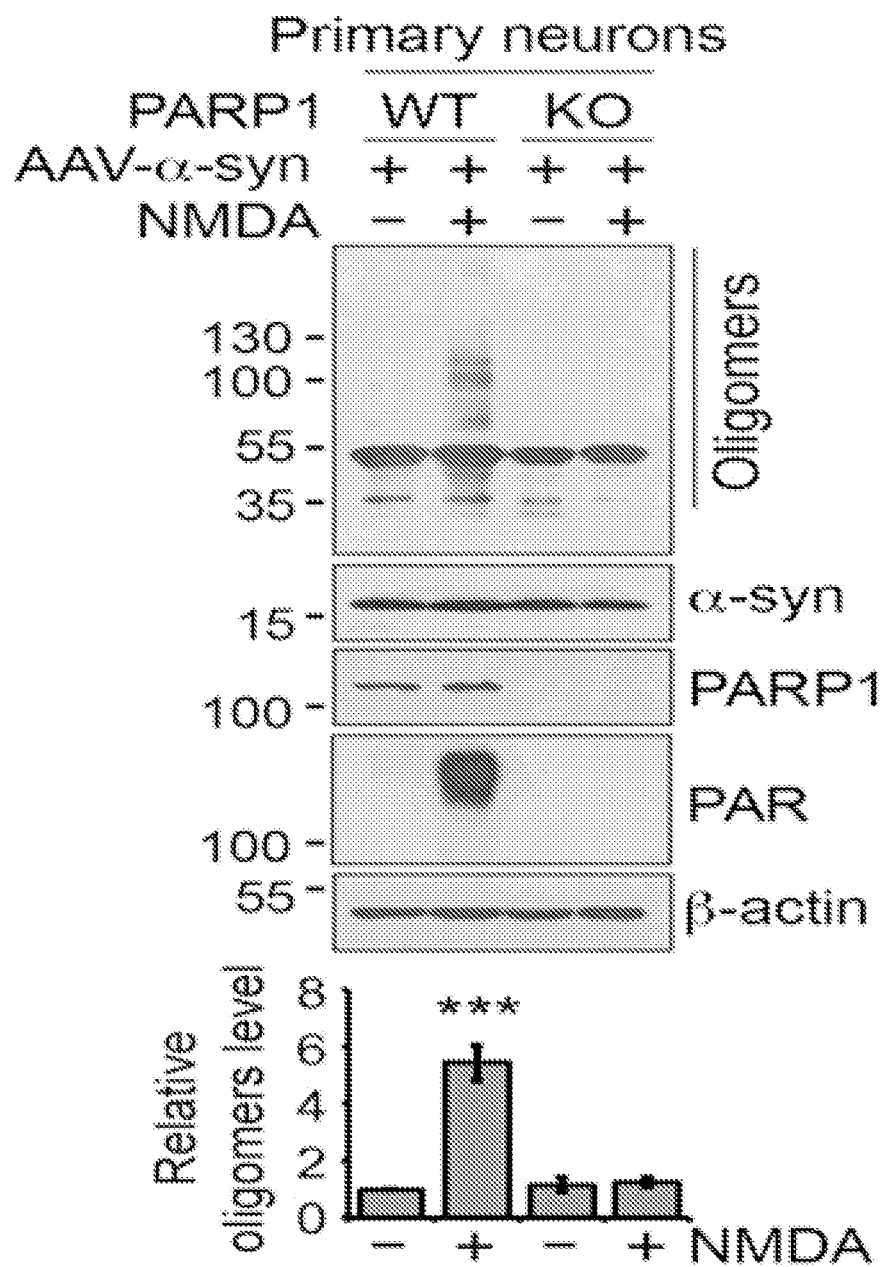
FIG. 22 shows suppression of NMDA-induced α-syn fibrillization in PARP-1 KO neurons. Primary cortical neurons from WT or PARP-1 KO embryos were transduced with AAV-α-syn and then further incubated with 500 μM NMDA for 5 min. The α-syn fibrillization was detected by western blot analysis 6 h after NMDA treatment.
Figure 23:
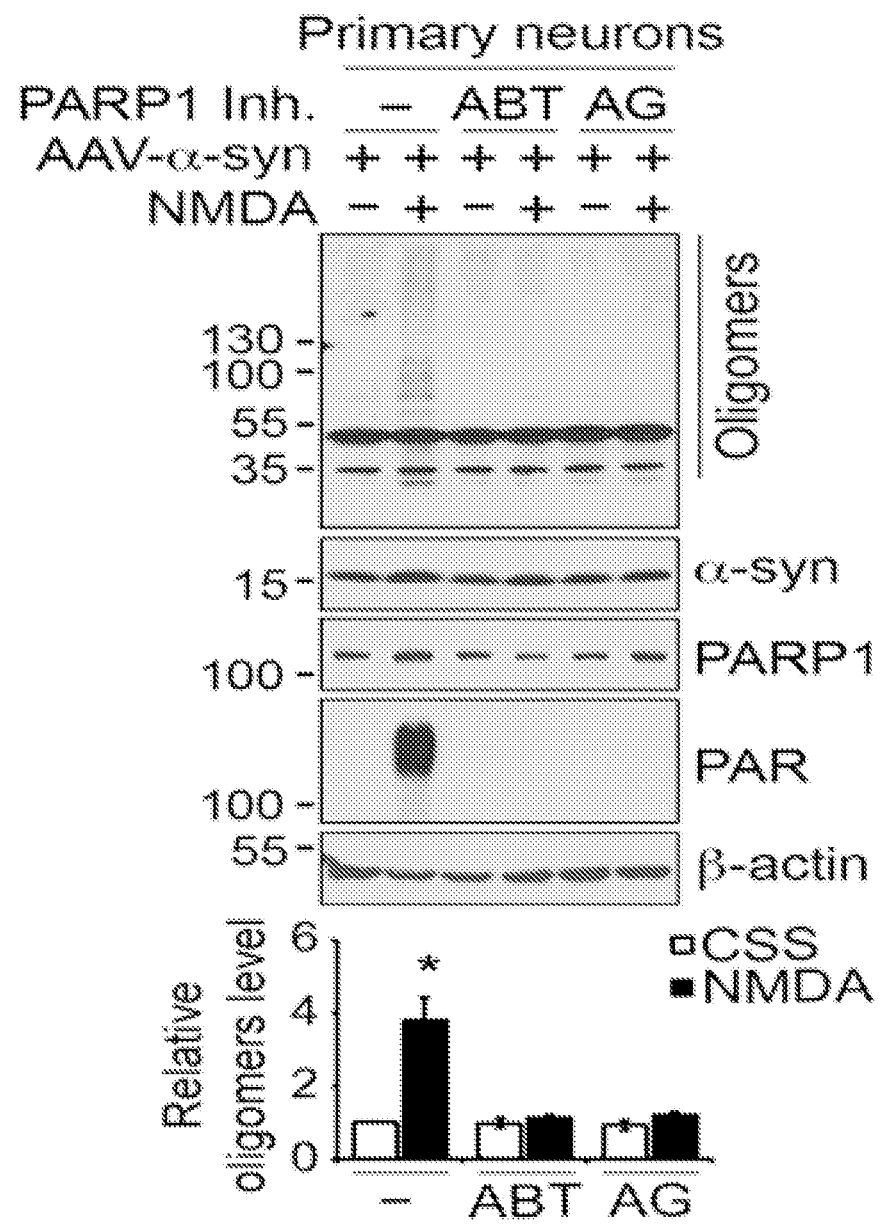
FIG. 23 shows prevention of NMDA-induced α-syn fibrillization by PARP1 inhibitors. The primary cortical neurons transduced with AAV-α-syn were pre-treated with 10 μM ABT-888 or 1 μM AG-014699 for 1 h, and further incubated with 500 μM NMDA for 5 min. The α-syn fibrillization was detected by western blot analysis 6 h after NMDA treatment.
Figure 66:
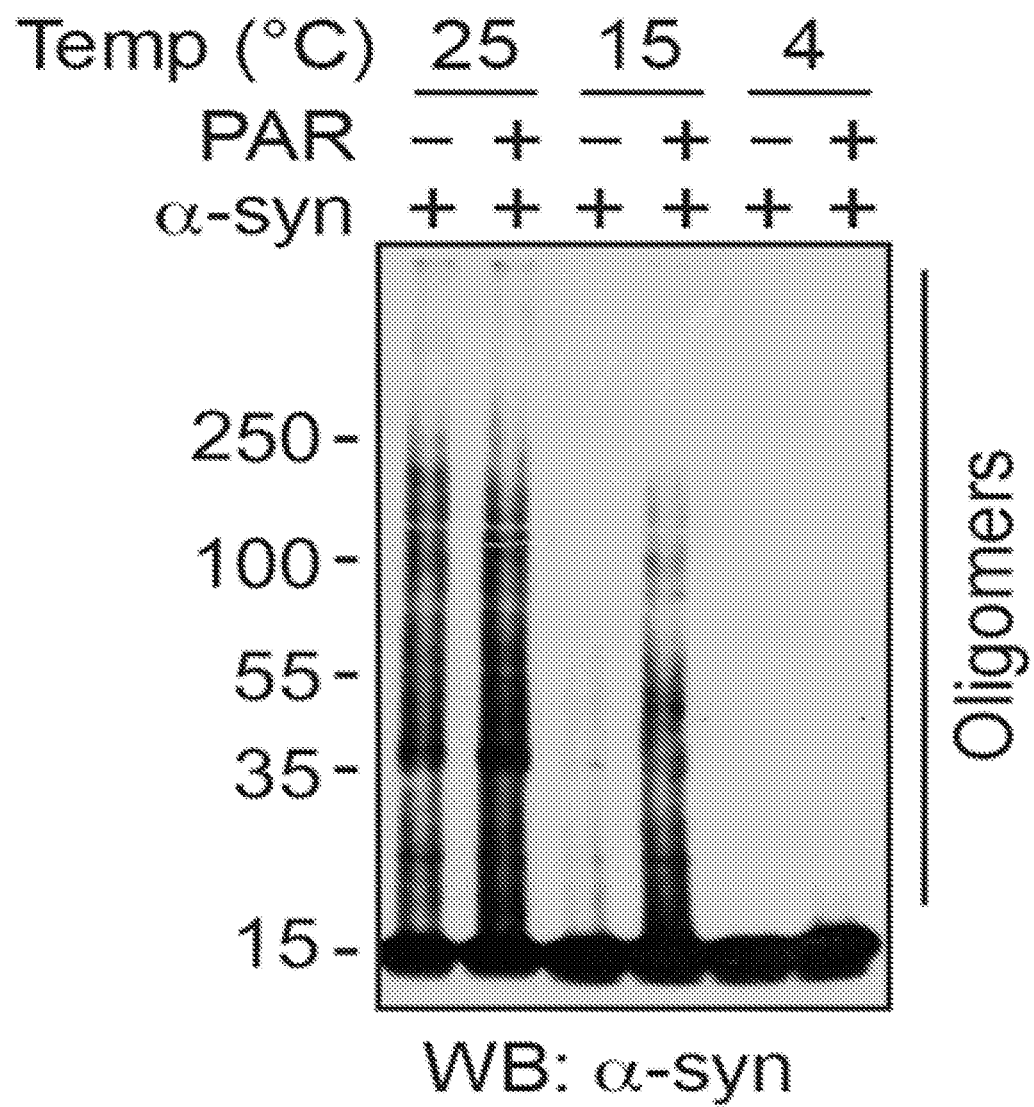
FIG. 66 shows the effect of temperature on PAR-mediated acceleration of α-syn fibrillization. Monomeric α-syn either with or without 5 nM PAR was incubated at indicated temperatures for 72 h. Fibrillization of α-syn was detected by immunoblotting using α-syn antibody.
Figure 67:
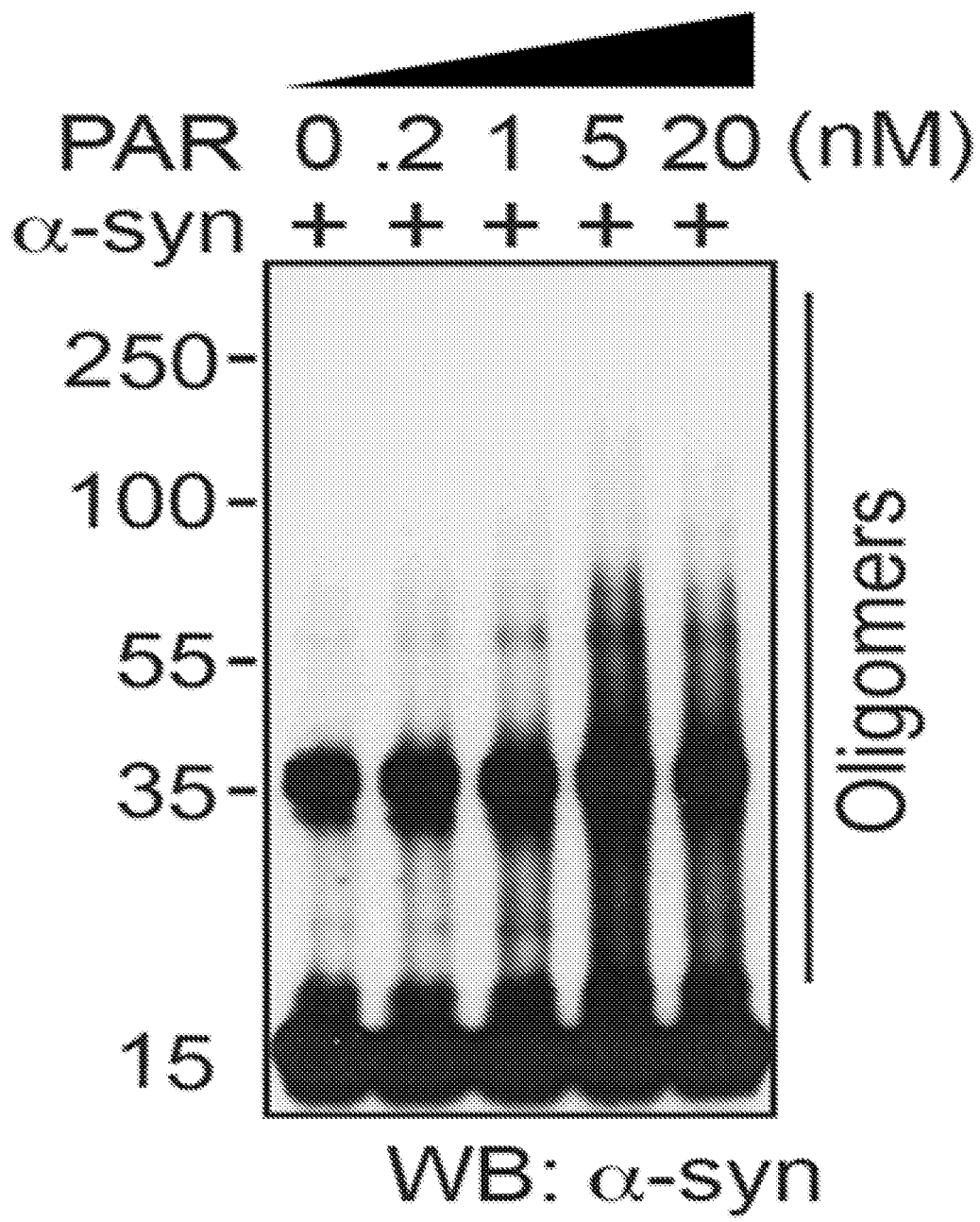
FIG. 67 shows the concentration dependence of PAR-mediated α-syn fibrillization. The α-syn fibrillization was detected by western blot analysis 36 h after incubation.
Figure 68:
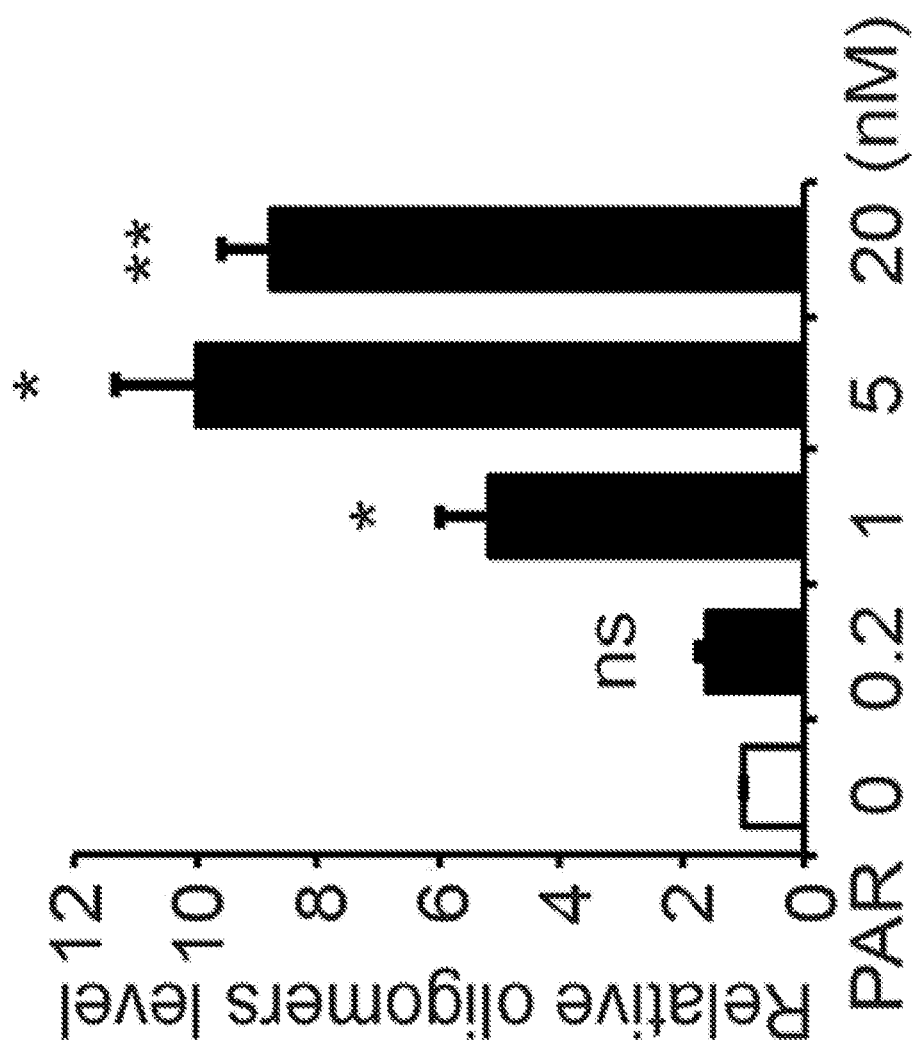
FIG. 68 shows quantification of α-syn fibrillization. Bars represent mean±s.e.m. One-way ANOVA followed by Tukey's post hoc test.
Figure 69:
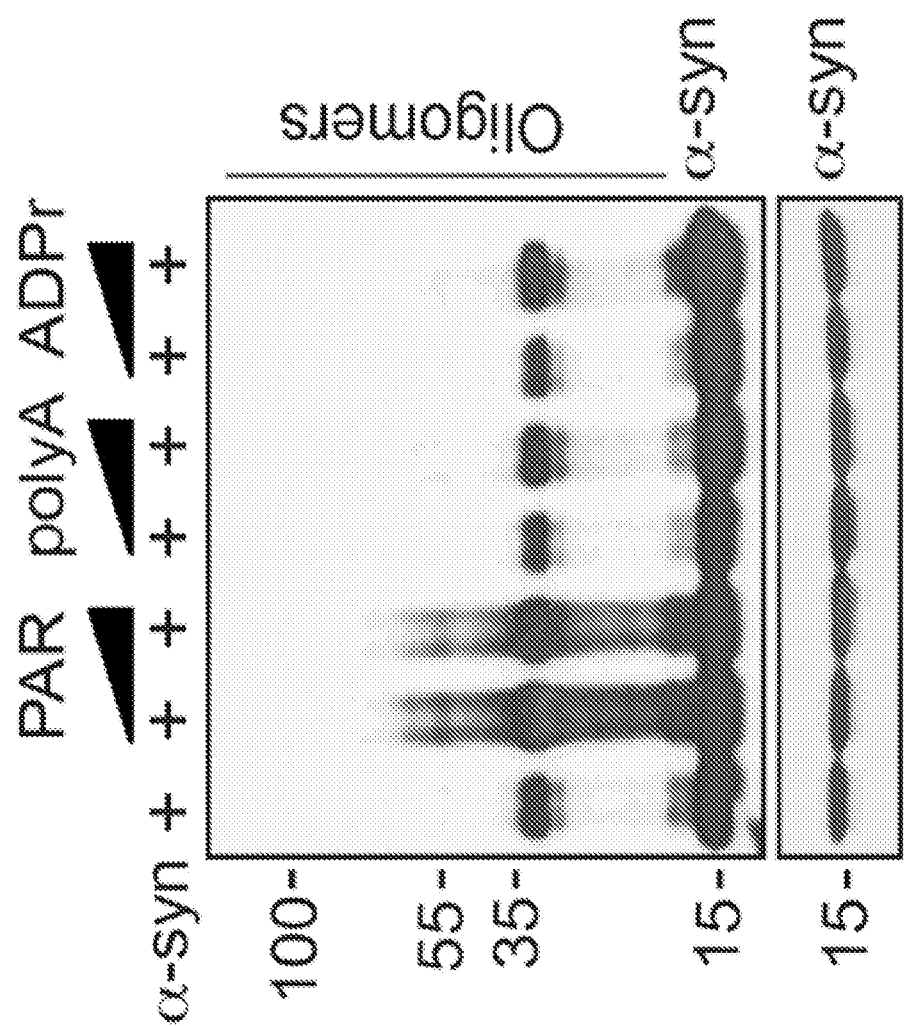
FIG. 69 shows representative immunoblot of α-syn fibrillization generated by adding 5 nM of PAR, Poly (A), or ADPr at 37° C. for 36 h.
Figure 70:
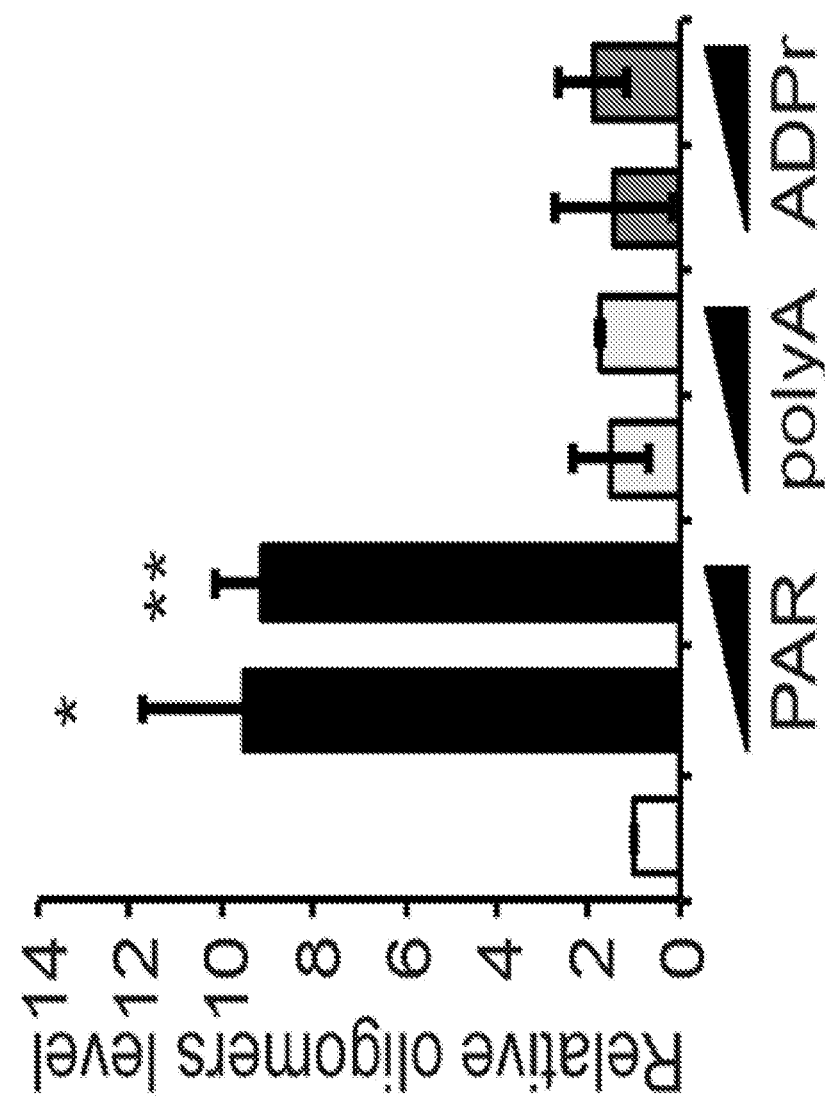
FIG. 70 shows quantification of α-syn fibrillization. Bars represent mean±s.e.m. One-way ANOVA followed by Tukey's post hoc test.
Figure 71:
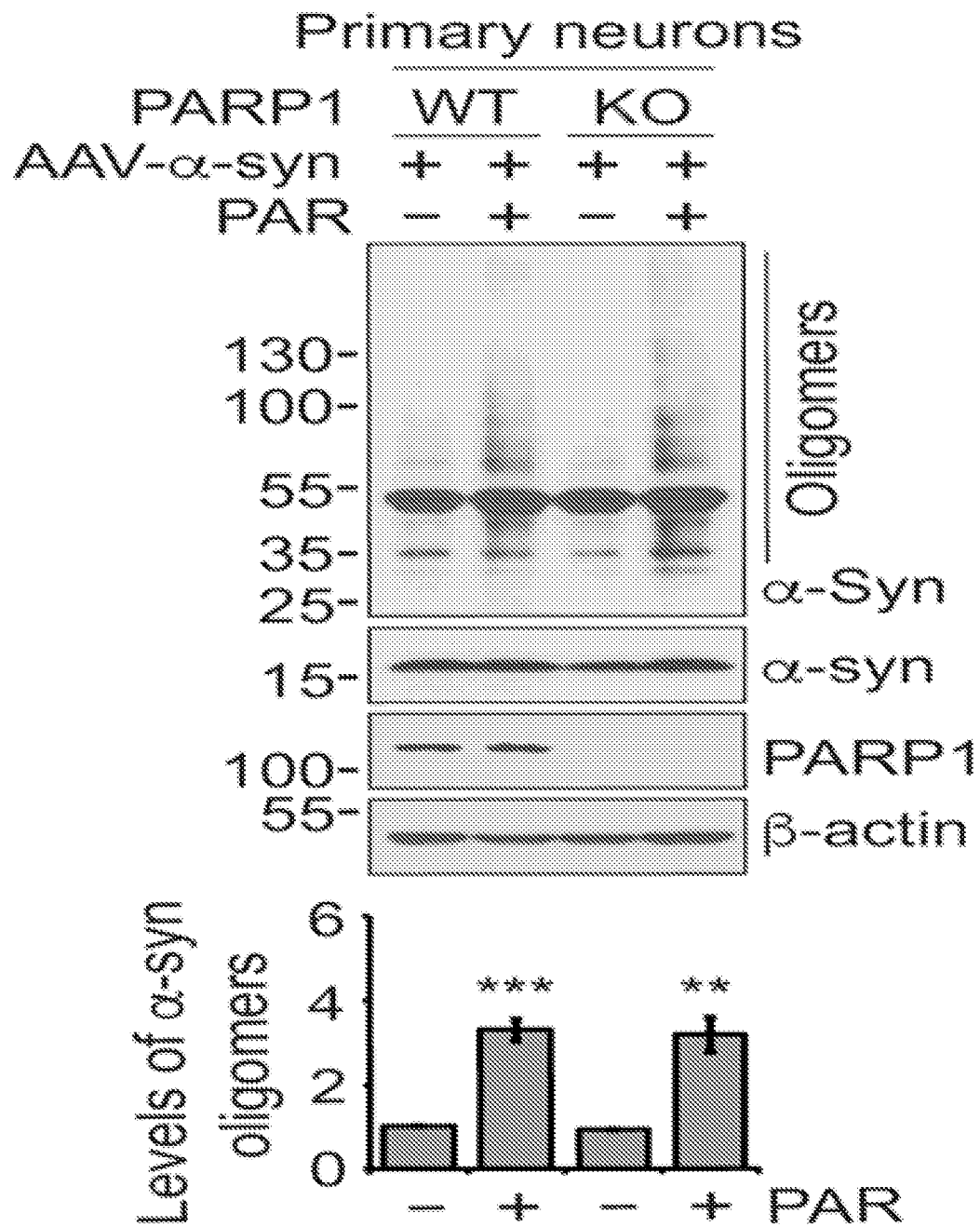
FIG. 71 shows primary cortical neurons from WT or PARP1 KO embryos were transduced with AAV-α-syn for 5 days and then PAR polymer was delivered with BioPorter for 6 h. The α-syn fibrillization was detected by western blot analysis.
Figure 72:
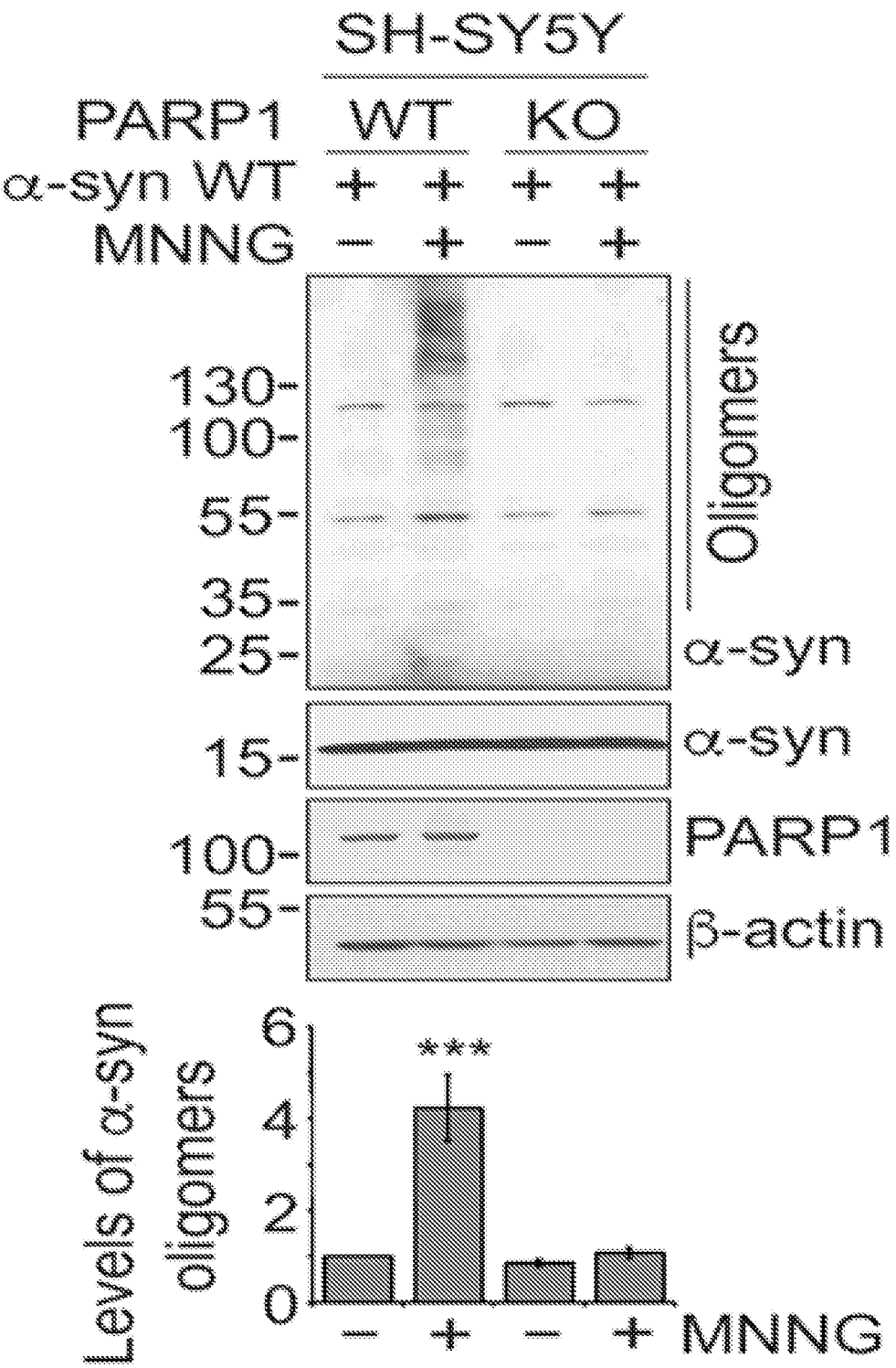
FIG. 72 shows WT or PARP1 KO SH-SYSY cells transfected with α-syn WT for 24 h and then further incubated with 50 μM MNNG for 15 min. The α-syn fibrillization was detected by western blot analysis 6 h after MNNG treatment.
Figure 73:
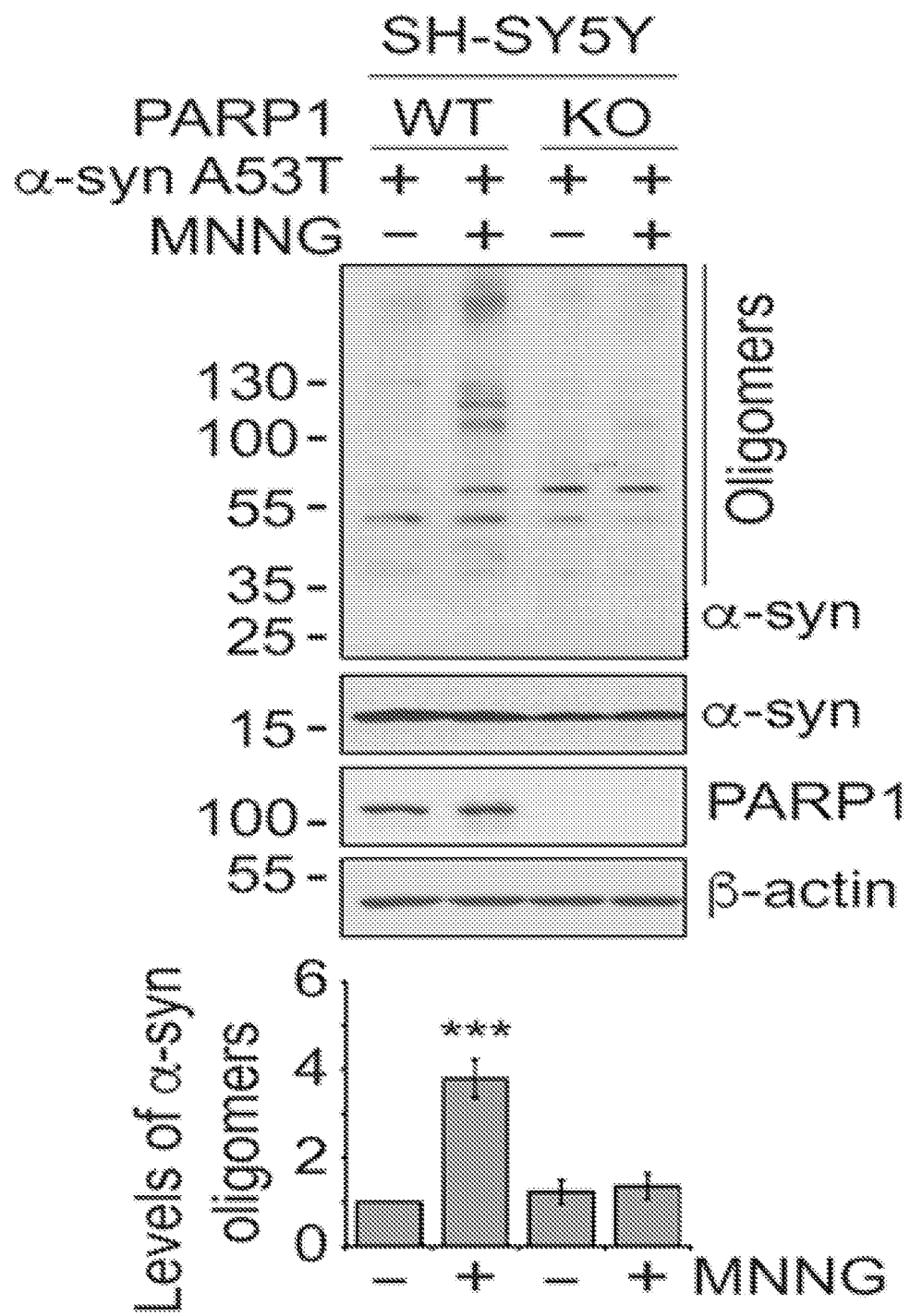
FIG. 73 shows WT or PARP1 KO SH-SYSY cells transfected with α-syn A53T for 24 h and then further incubated with 50 μM MNNG for 15 min. The α-syn fibrillization was detected by western blot analysis 6 h after MNNG treatment.
Figure 74:
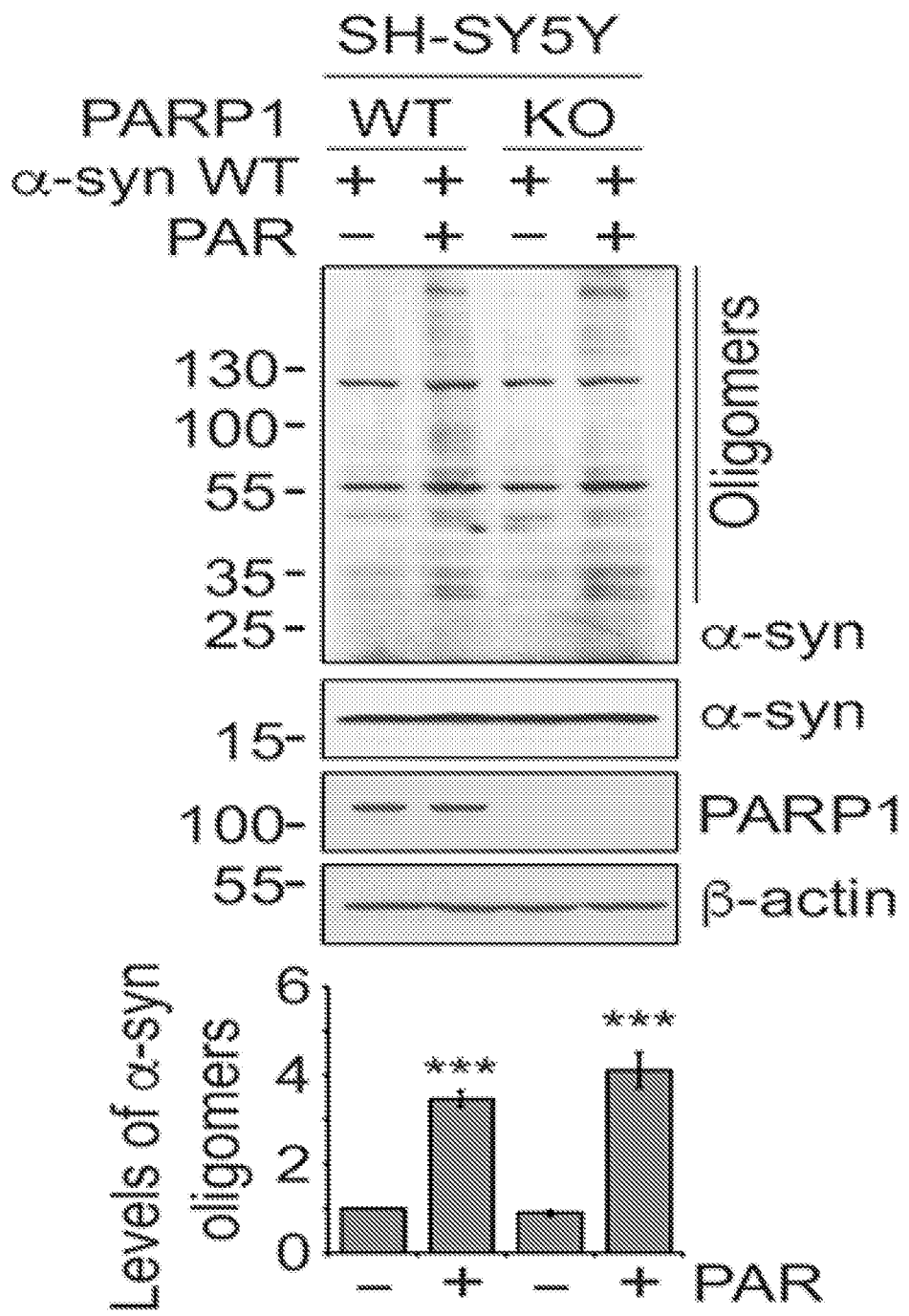
FIG. 74 shows WT or PARP1 KO SH-SYSY cells were transfected with α-syn WT for 24 h and then PAR polymer was delivered with BioPorter for 6 h. The α-syn fibrillization was detected by western blot analysis.
Figure 75:
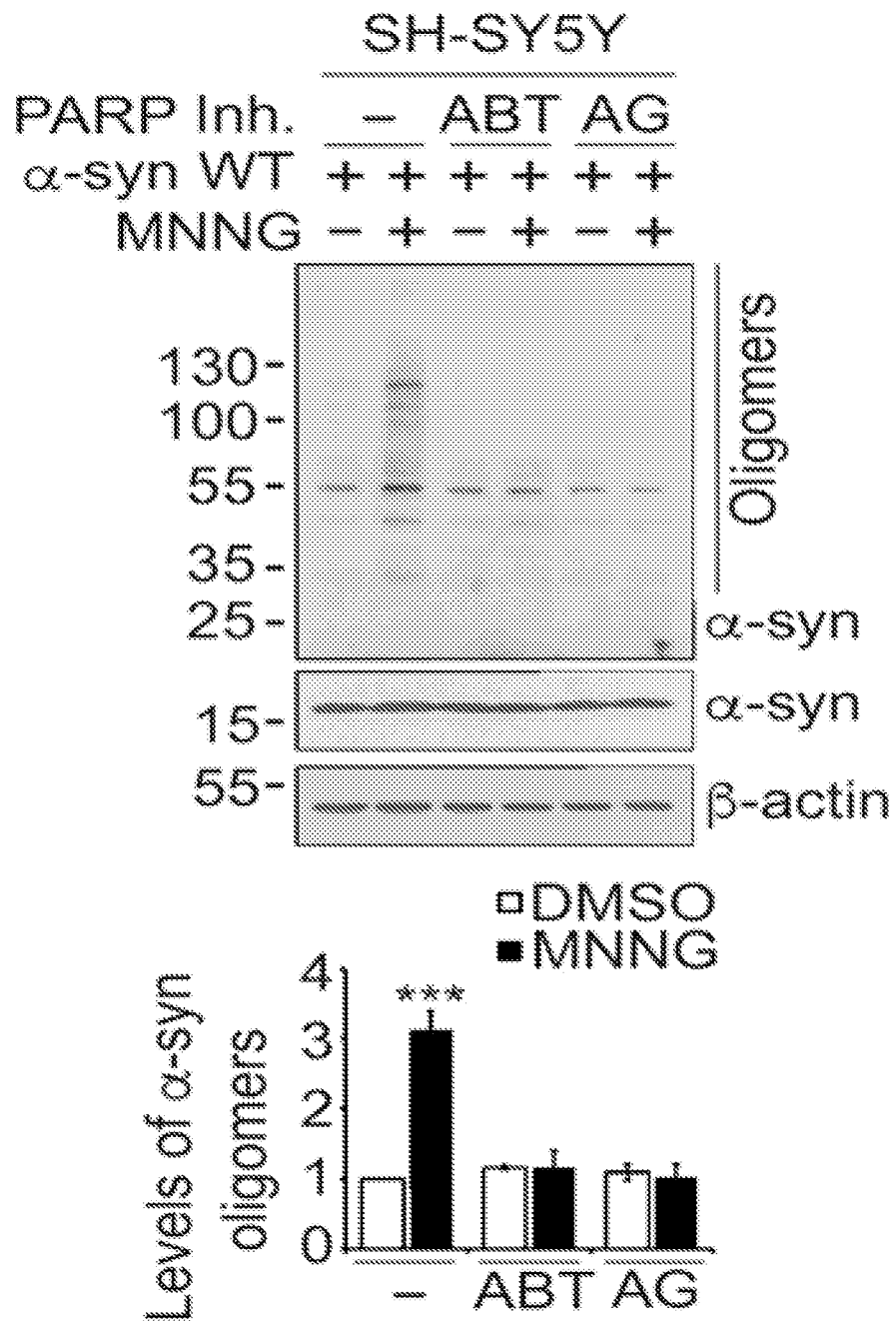
FIG. 75 shows SH-SYSY cells transfected with α-syn WT for 24 h were pretreated with 10 μM ABT-888 or 1 μM AG-014699 for 1 h, and further incubated with 50 μM MNNG for 15 min. The α-syn fibrillization was detected by western blot analysis 6 h after MNNG treatment. Bars represent mean±s.e.m. One-way ANOVA followed by Tukey's post hoc test. *$P<0.05$, $P<0.005$, *$P<0.001$.

Since PAR causes liquid demixing of intrinsically disordered proteins leading to their aggregation, experiments were performed to determine whether PAR could seed and accelerate α-syn aggregation. Recombinant α-syn was incubated at 37° C. and agitated in the presence and absence of 5 nM PAR, concentrations that are observed in brain tissue. High molecular weight forms of α-syn in the absence of PAR are observed as early as 4 hours of incubation and α-syn continues to fibrillize with time (FIG. 19). Different molecular weight forms of α-syn are observed at 72 hours. In the presence of PAR, the fibrillization of α-syn is markedly accelerated with different molecular weight forms of α-syn being observed as early as 24 h of incubation (FIG. 19). Thioflavin T fluorescence also indicates that PAR accelerates the fibrillization of α-syn, while PAR alone has no effect on thioflavin T fluorescence (FIG. 20). The effect of temperature on PAR mediated acceleration of the fibrillization of α-syn was also assessed (FIG. 66). PAR causes the fibrillization of α-syn at temperatures that are not permissive for α-syn fibrillization in the absence of PAR (FIG. 66). Transmission electron microscopy (TEM) was used to monitor the formation of α-syn fibrils. At 12 hours α-syn fibrils begin to form in the absence of PAR and become fully formed and extensive after 72 hours of agitation and incubation at 37° C. (FIG. 3C). In contrast, in the presence of PAR, α-syn is extensively fibrillated at 12 hours and becomes more extensively fibrillated at 24 and 72 hours (FIG. 21). At 36 hours the concentration dependence of α-syn fibrillization in the presence of PAR was monitored. 1 nM PAR is capable of enhancing α-syn fibrillization with peak aggregation occurring at 5 nM PAR while 20 nM PAR does not appreciably increase α-syn fibrillization (FIGS. 67 and 68). Since PAR is a highly negatively charged molecule, the effects of another highly charged polymer were tested, PolyA, and which had no effects on α-syn fibrillization (FIGS. 69 and 70). ADP ribose monomer also had no effect on α-syn fibrillization (FIGS. 69 and 70). To determine whether endogenous PAR formation can accelerate α-syn fibrillization, primary mouse cortical neurons overexpressing WT human α-syn following AAV-α-syn transduction were treated with a toxic dose of N-methyl-D-aspartate (NMDA). In WT cultures NMDA treatment leads to activation of PARP as assessed by PAR immunoblot and a concomitant aggregation of α-syn, while α-syn did not aggregate in PARP-1 KO cultures treated with NMDA (FIG. 22). Exogenous administration of PAR via Bioporter increases the aggregation of α-syn in both WT and PARP-1 KO cultures transduced with AAV-α-syn (FIG. 71), indicating that PAR, not PARP-1, can directly increase α-syn aggregation. Two different PARP inhibitors, ABT888 and AG014699, prevent α-syn aggregation and PARP activation in response to NMDA administration (FIG. 23). In SH-SYSY cells the potent PARP activator N-methyl-N'-nitro-N-nitrosoguanidine (MNNG) enhances the aggregation of overexpressed WT or A53T α-syn in SH-SYSY cells, while MNNG has no effect in PARP-1 KO SH-SYSY cells (FIGS. 72 and 73). Exogenous administration of PAR increased the aggregation of α-syn in both SH-SYSY WT and SH-SYSY PARP-1 KO cultures (FIG. 74). Two different PARP inhibitors, ABT888 and AG014699, prevent α-syn aggregation and PARP activation in response to MNNG administration in SH-SYSY cells (FIG. 75).

Figure 24:
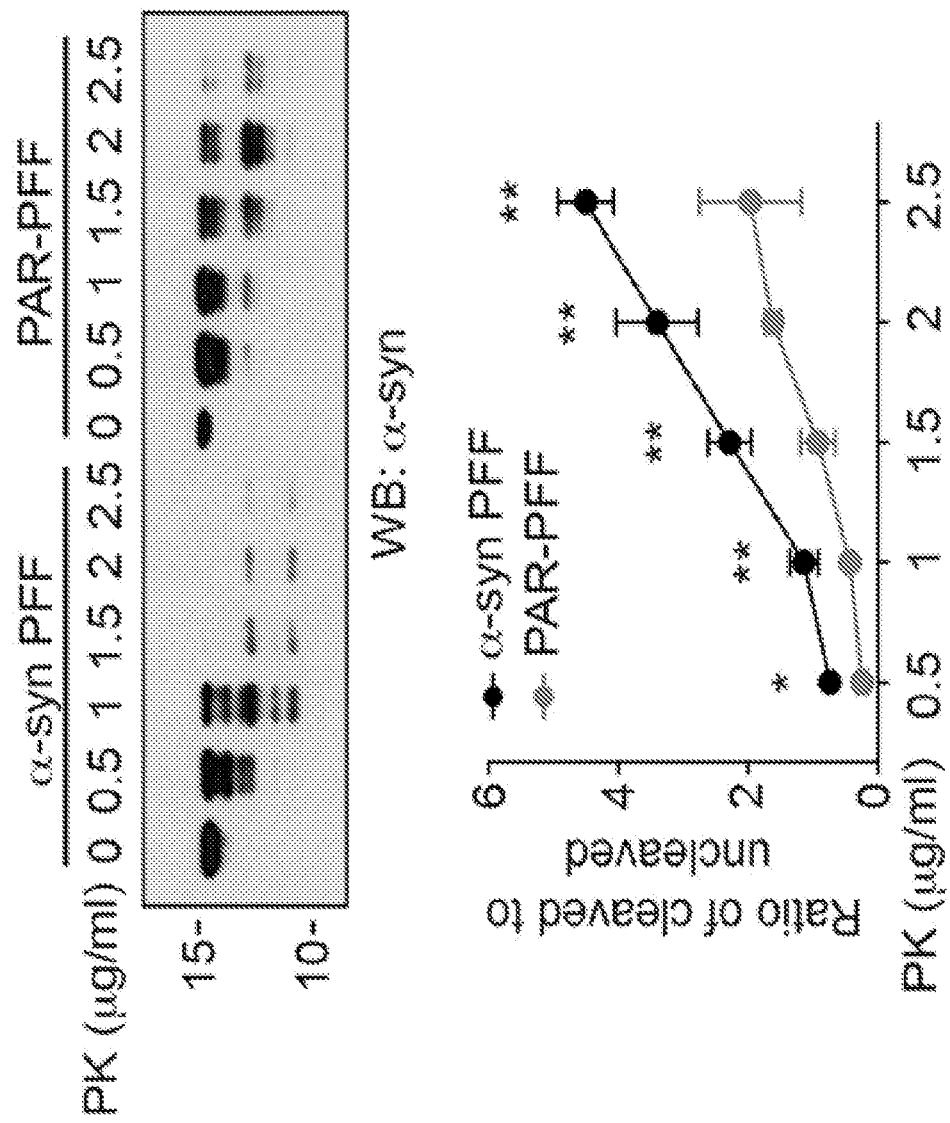
FIG. 24 shows α-syn PFF or PAR-α-syn PFF incubated with increasing concentration of PK (0-2.5 μg/ml) and immunoblotted with α-syn antibody (top). Quantification represents the ratio of cleaved to uncleaved α-syn (bottom). Data are mean±s.e.m. (bottom). One-way ANOVA followed by Tukey's post hoc test (n=3).
Figure 25:
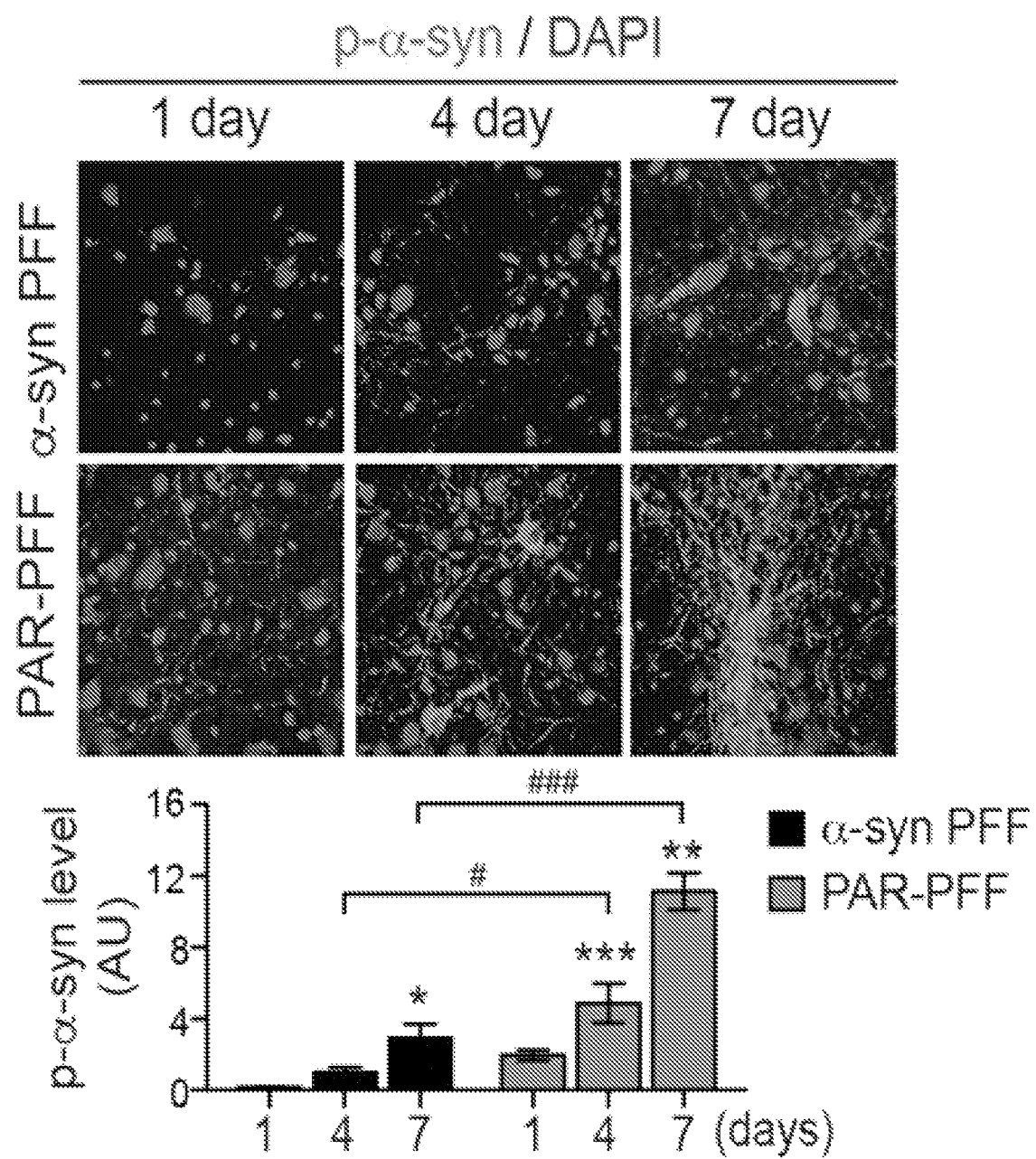
FIG. 25 shows representative immunostaining of p-α-syn (red) in primary cortical neurons treated with α-syn PFF or PAR-α-syn PFF for 1, 4 and 7 days. Quantification of p-α-syn signals normalized with DAPI (right). Bars represent mean±s.e.m. (bottom). One-way ANOVA followed by Tukey's post hoc test (n=5).
Figure 26:
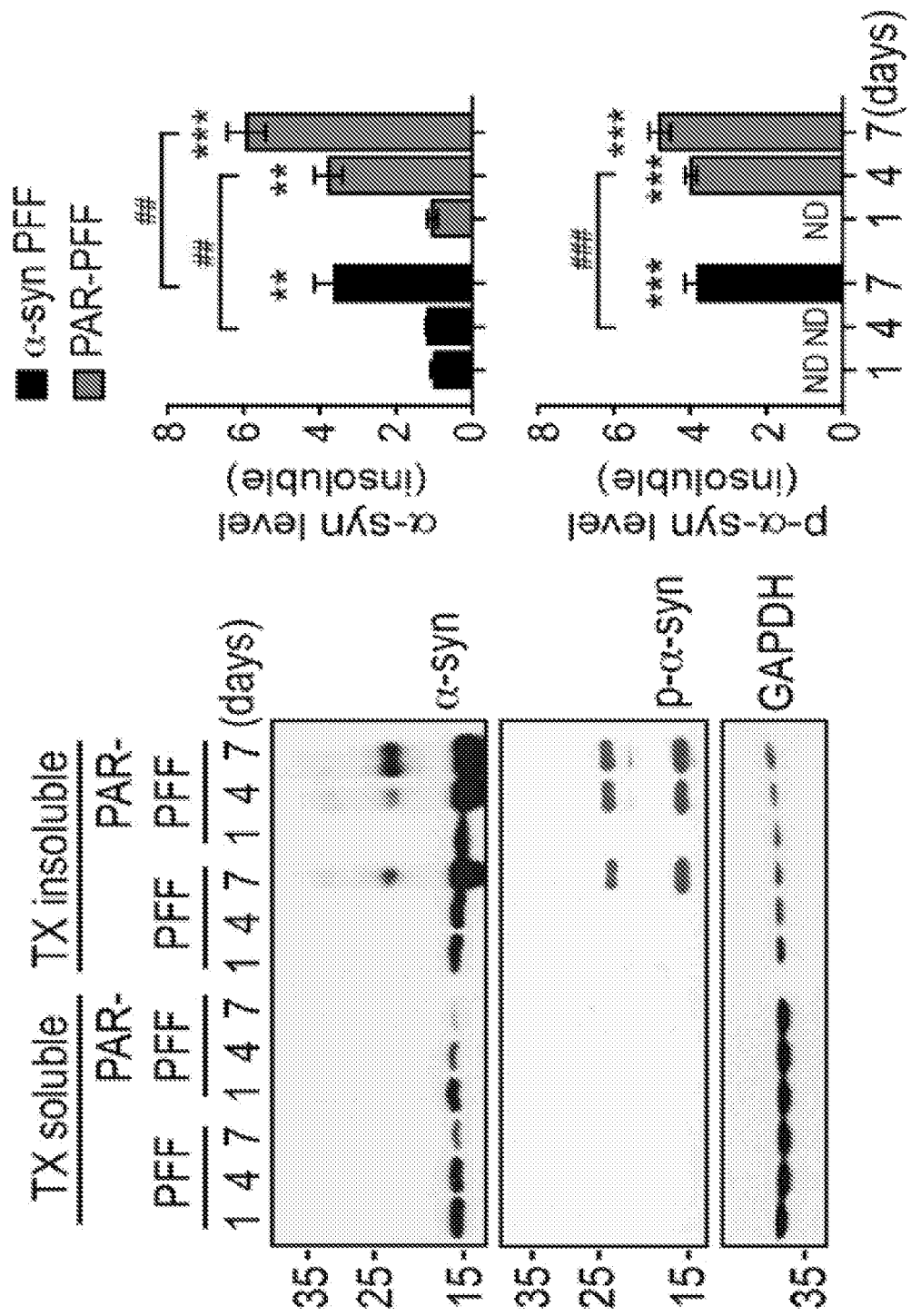
FIG. 26 shows primary cortical neurons treated with α-syn PFF or PAR-α-syn PFF were sequentially extracted with 1% TX-100 (TX soluble) and 2% SDS (TX insoluble). Lysates were subjected to immunoblotting using α-syn, p-α-syn, and GAPDH antibodies. Bars represent mean±s.e.m. One-way ANOVA followed by Tukey's post hoc test (n=3). ND, not detected. *P<0.05, P<0.005, *P<0.0005 as compared to α-syn PFF for 1 day. #P<0.05, 44/3<0.005, ####P<0.0005.
Figure 76:
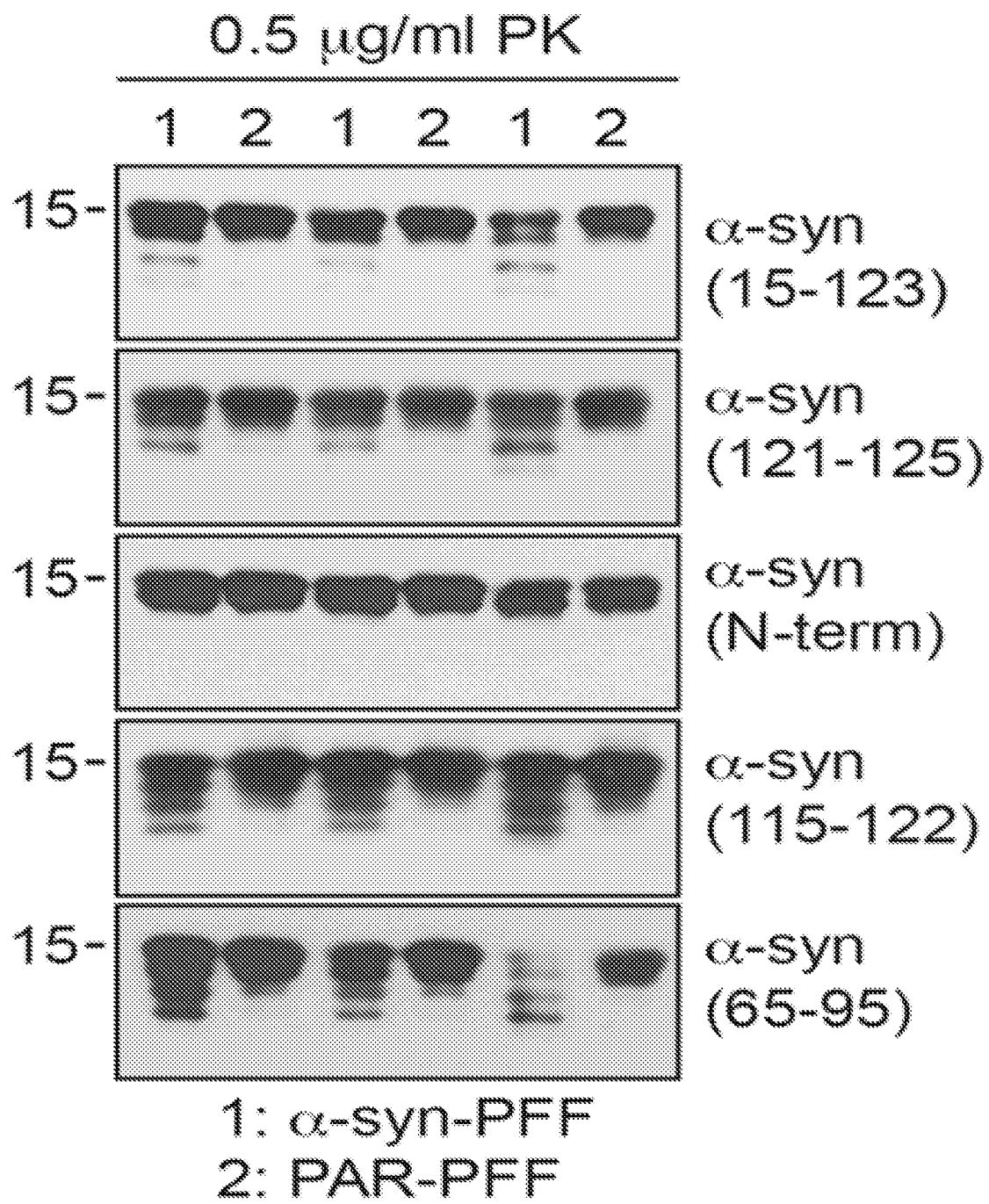
FIG. 76 shows α-syn PFF or PAR-α-syn PFF was incubated with 0.5 μg/ml of PK and immunoblotted with epitope-specific antibodies to α-syn.
Figure 77:
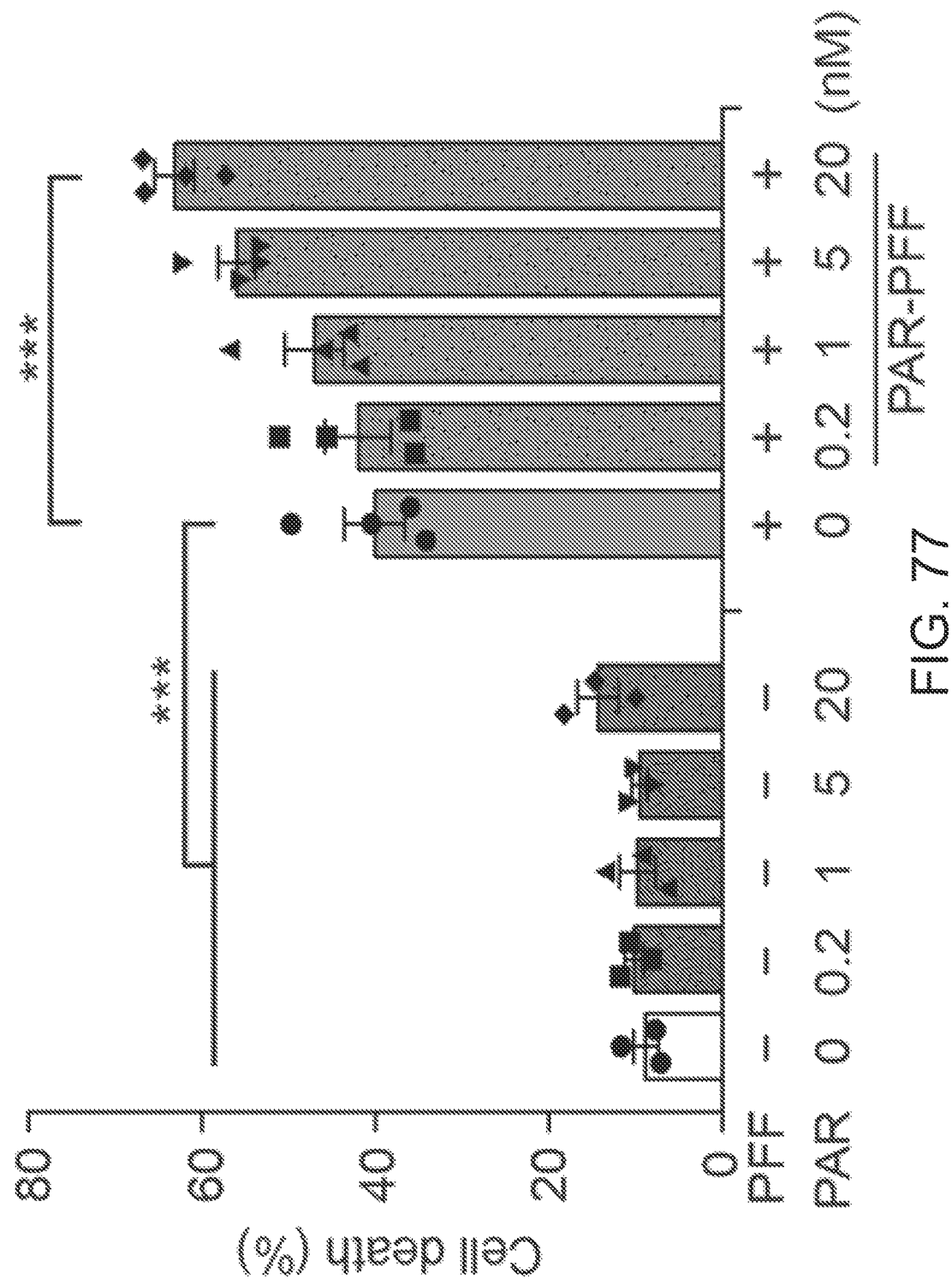
FIG. 77 shows PAR-α-syn PFF was generated with increasing dose of purified PAR polymer. Primary cortical neurons were treated with the same amount of α-syn PFF or PAR-α-syn PFF for 14 days. Cell death was determined by Hoechst and propidium iodide (PI) staining. Bars represent mean±s.e.m. One-way ANOVA followed by Tukey's post hoc test (n=3-4).
Figure 78:
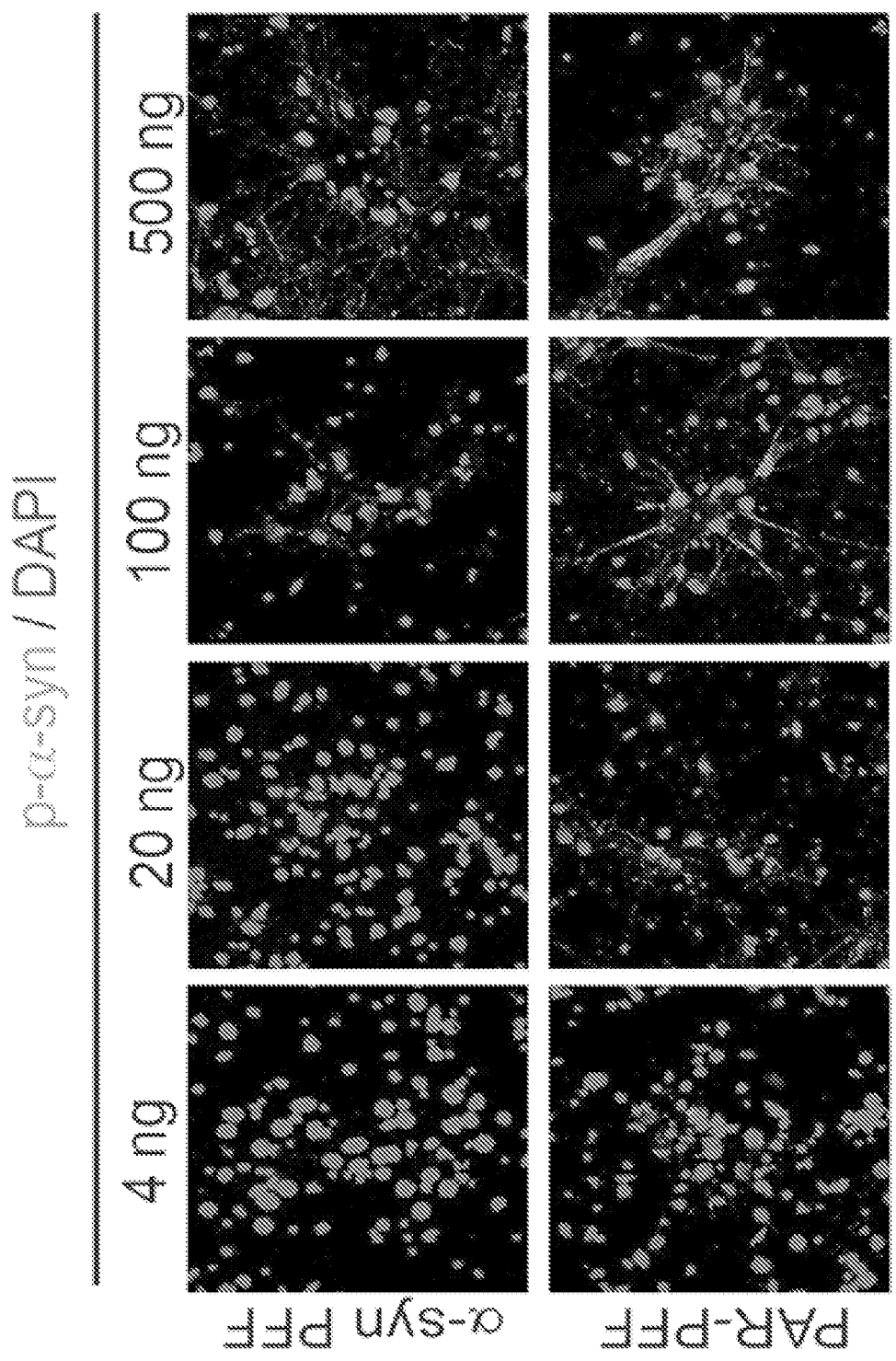
FIG. 78 shows representative immunostaining of p-α-syn (red) in primary cortical neurons treated with increasing amount of α-syn PFF or PAR-α-syn PFF for 4 days. Nuclei are stained with DAPI (blue).
Figure 79:
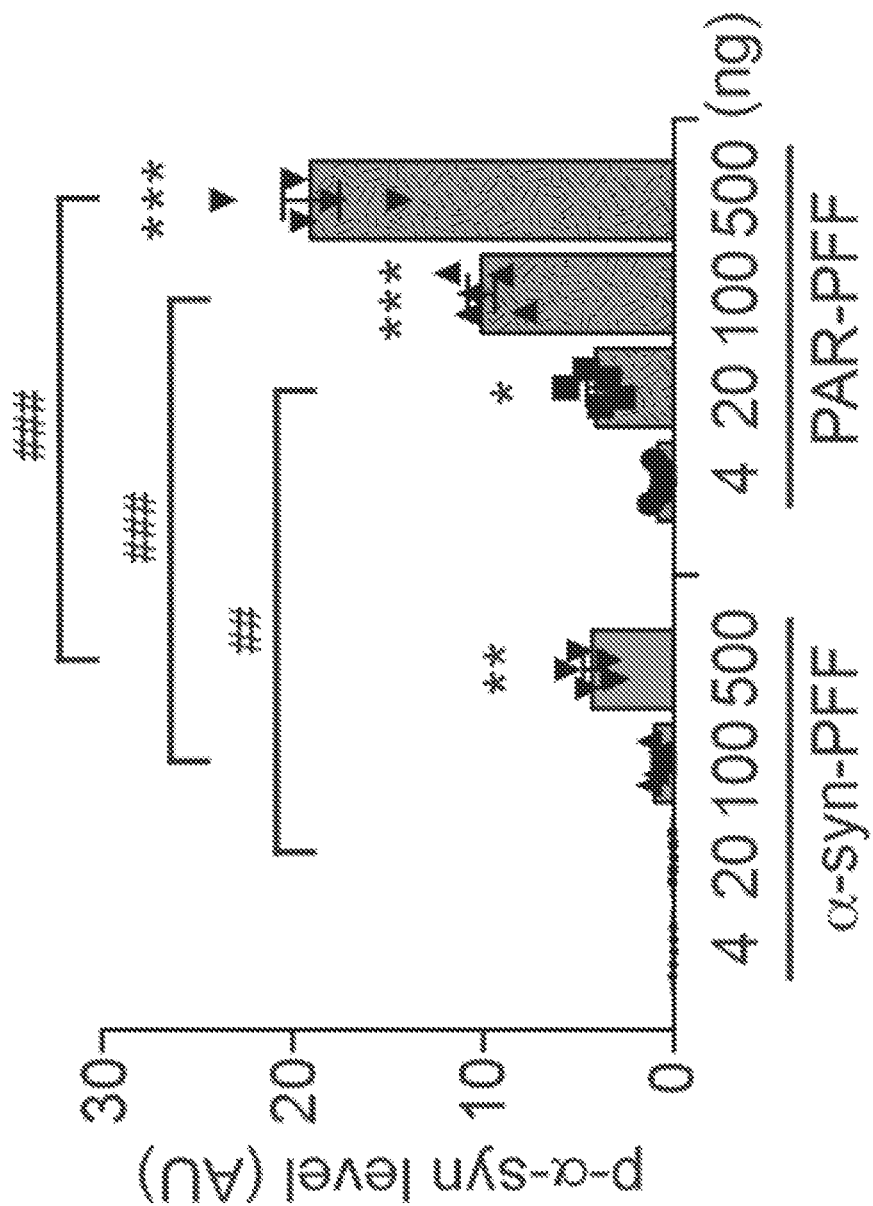
FIG. 79 shows quantification of p-α-syn signals normalized with DAPI (n=5). One-way ANOVA with Tukey's post hoc test. *$P<0.05$, $P<0.005$, *$P<0.001$.

To determine whether PAR changes the biophysical properties of α-syn PFF, a series of biochemical analysis were conducted using α-syn PFF and α-syn PFF in the presence of PAR (PAR-α-syn PFF). First, proteinase K (PK) digestion of α-syn PFF was performed and monitored by α-syn immunoblots. α-syn PFF and PAR-α-syn PFF showed very distinct banding patterns after PK digestion, with PAR-α-syn PFF's being more resistant to increasing concentrations of PK (FIG. 24). PAR-α-syn PFF showed predominantly an undigested band of α-syn ($1^{st}$ band) with comparable digested bands only at higher concentration of PK, while α-syn PFF degraded into smaller fragments ($2^{nd}$ to $5^{th}$ band) at lower concentration of PK (0.5 and 1 µg/ml) and these bands became predominant at higher concentration of PK (1.5-2.5 µg/ml) (FIG. 24). Using epitope specific antibodies to α-syn, it was found that PAR renders the majority of the α-syn regions resistant to PK digestion (FIG. 76). The resistance to PK digestion of PAR-α-syn PFF suggests that PAR induces the formation of distinct α-syn PFF strains with more misfolded and compact structure than α-syn PFF. α-syn PFF and PAR-α-syn PFF-induced neuronal cell death were then compared in cultured neurons. After 14 days of treatment, there is enhanced cell death in cultures treated with PAR-α-syn PFF as compared to that with α-syn PFF (FIG. 77). PAR itself does not cause significant cell death even at higher concentration (20 nM) (FIG. 77). To further confirm the potencies of neuropathology, p-α-syn immunoreactivity was monitored after treatment of varying concentration of α-syn PFF or PAR-α-syn PFF. P-a-syn immunoreactivity was observed at 20 ng of PAR-α-syn PFF at an equivalent level to 500 ng of α-syn PFF, suggesting the PAR modification of α-syn PFF increases toxicity by 25 fold (FIGS. 78 and 79). PAR-α-syn PFF significantly increased p-α-syn immunoreactivity at higher concentrations (FIGS. 78 and 79). Phospho-α-syn immunoreactivity at different time points was also monitored in cultured neurons exposed to α-syn PFF or PAR-α-syn PFF. In the absence of PAR, α-syn PFF treatment leads to barely detectable p-α-syn immunoreactivity 1 day post treatment, while PAR-α-syn PFF treatment leads to detectable levels of p-α-syn immunoreactivity as early as 1 day post treatment and markedly enhances immunoreactivity at 7 days (FIG. 25). Immunoblot analysis of α-syn indicates that aggregated and phosphorylated α-syn are detectable at 4 days, while in the absence of PAR these species of α-syn are only detectable after 7 days of treatment. In the presence of PAR there is an increase in the aggregated form of α-syn (FIG. 26).

Figure 27:
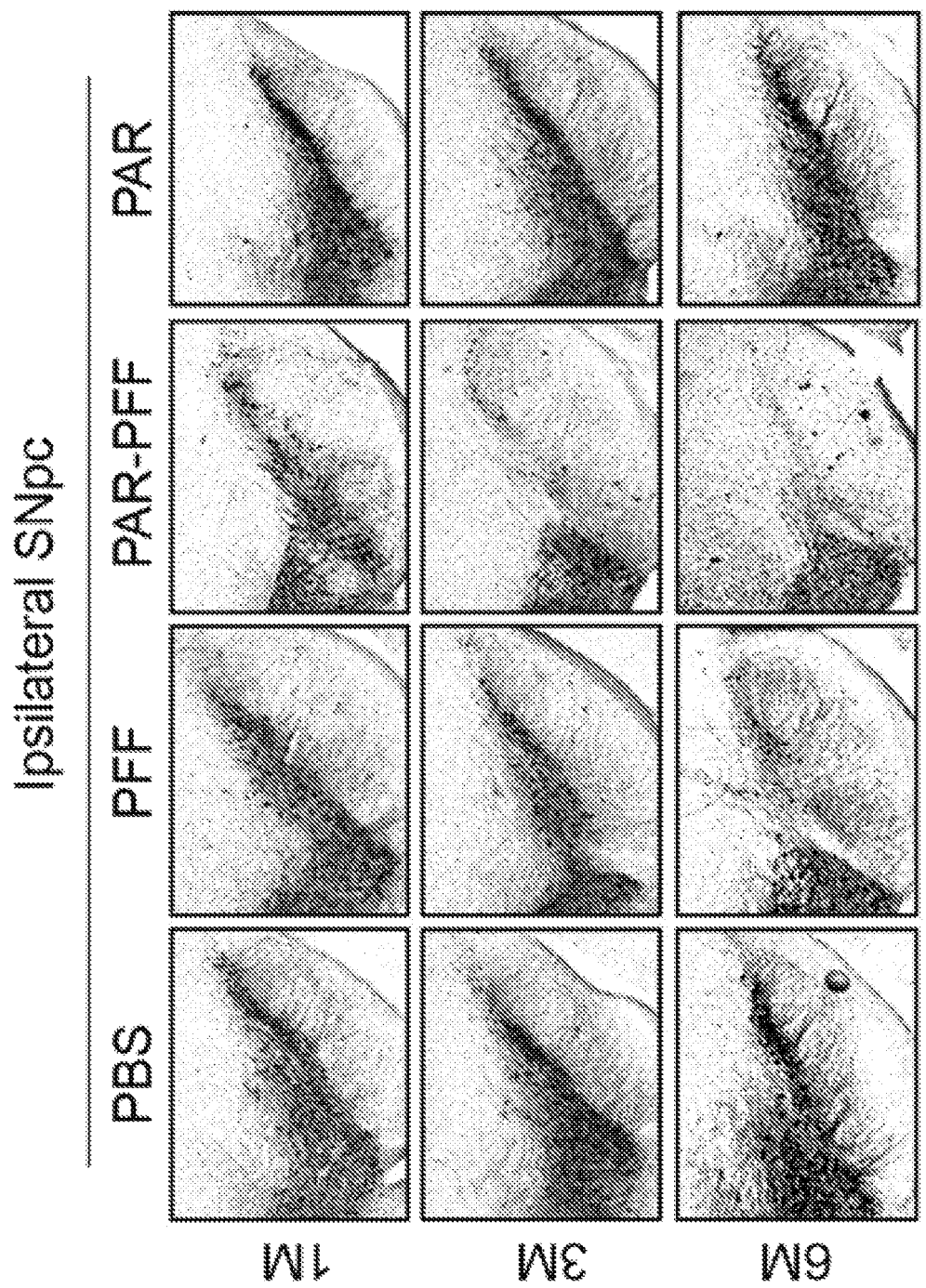
FIG. 27 shows representative TH and Nissl staining of SNpc DA neurons of WT mice at 1, 3, and 6 months after instrastriatal PBS, α-syn PFF, PAR-α-syn PFF, or PAR injection.
Figure 28:
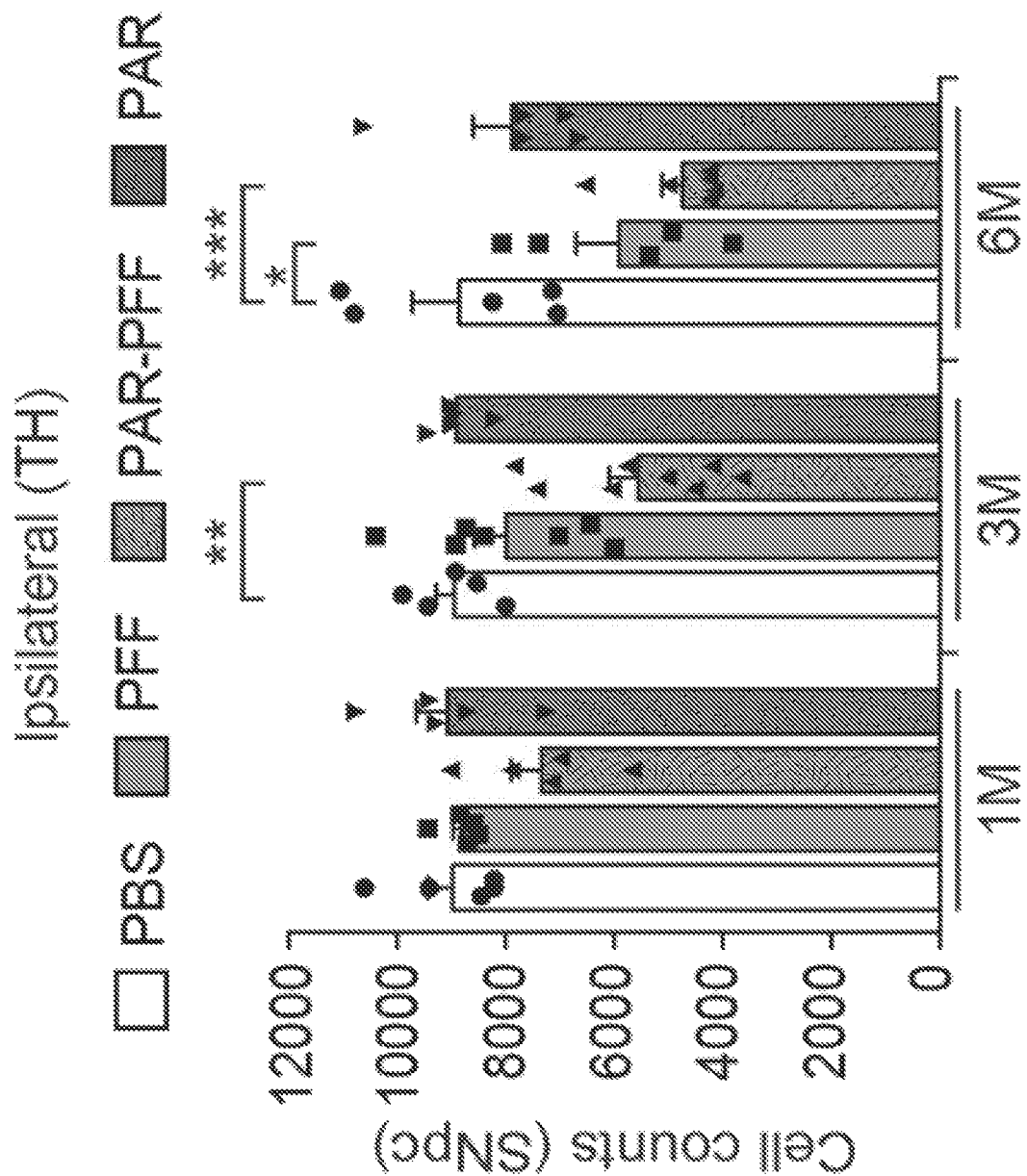
FIG. 28 shows stereological counts. Bars represent mean±s.e.m. One-way ANOVA followed by Tukey's post hoc test (n=5 to 8 mice per group).
Figure 29:
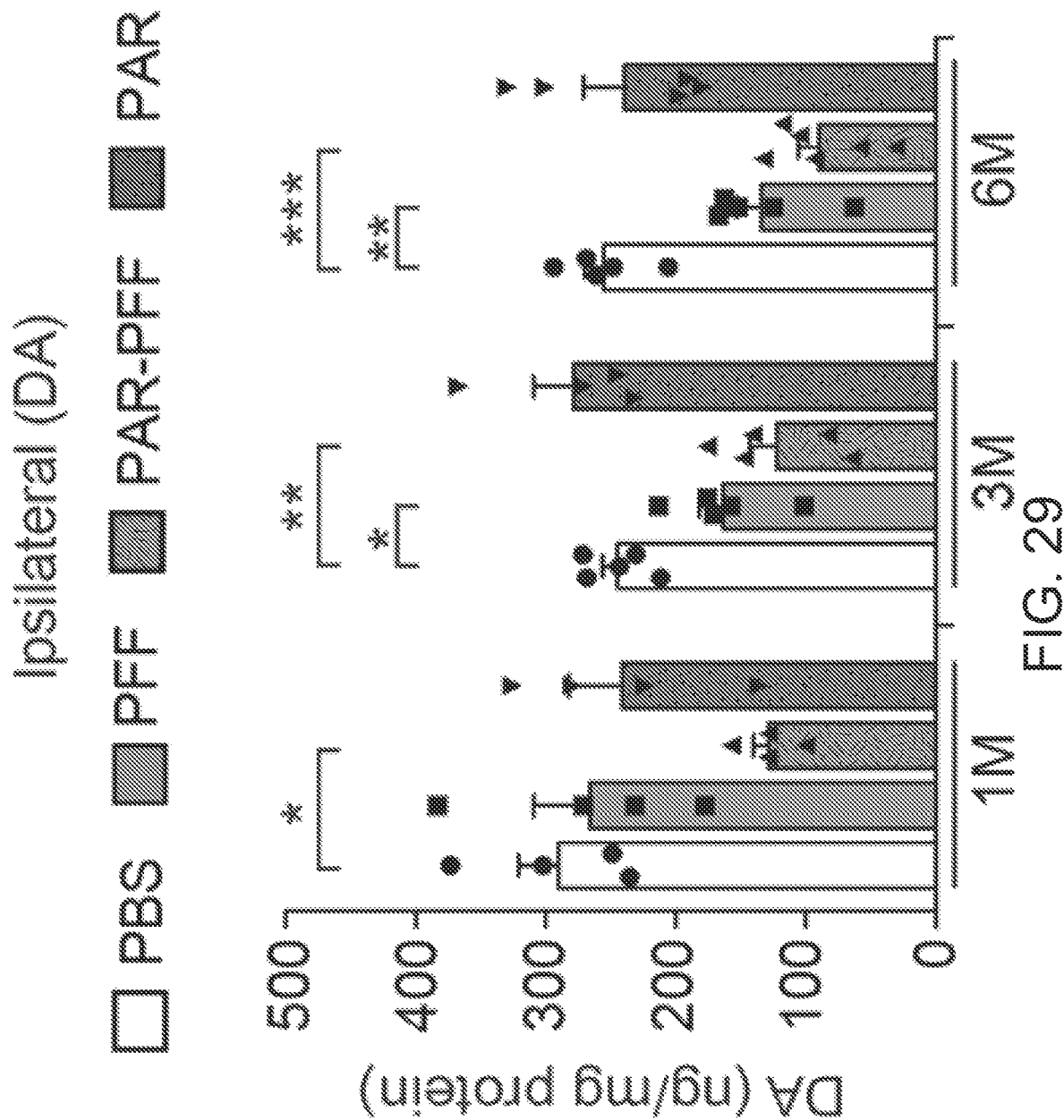
FIG. 29 shows DA concentrations in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group).
Figure 30:
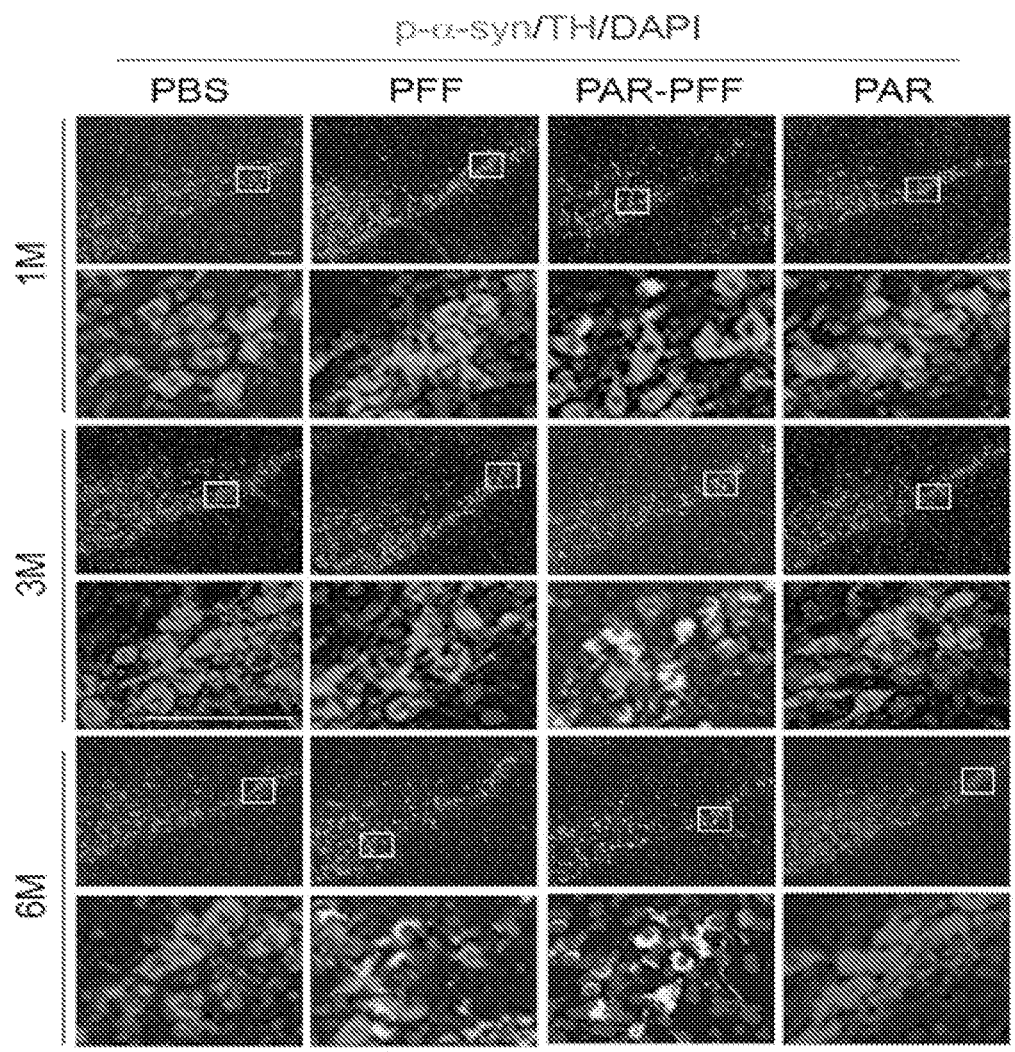
FIG. 30 shows representative p-α-syn immunostaining in the SNpc of WT mice at 1, 3, and 6 months after instrastriatal PBS, α-syn PFF, PAR-α-syn PFF, or PAR injection. Scale bar, 100 μm.
Figure 31:
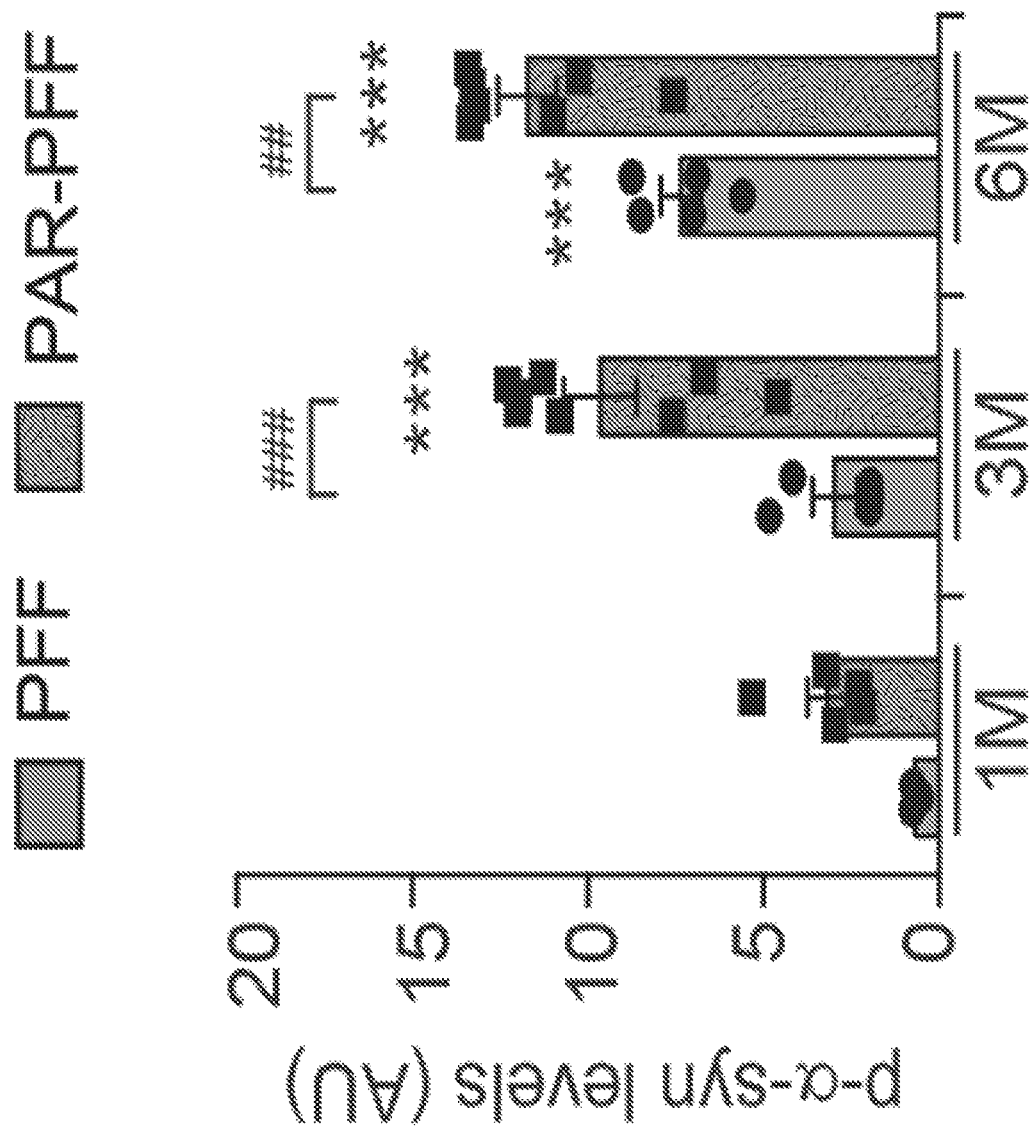
FIG. 31 shows quantification of p-α-syn levels. Bars represent mean±s.e.m. One-way ANOVA followed by Tukey's post hoc test (n=5 to 8 mice per group).
Figure 32:
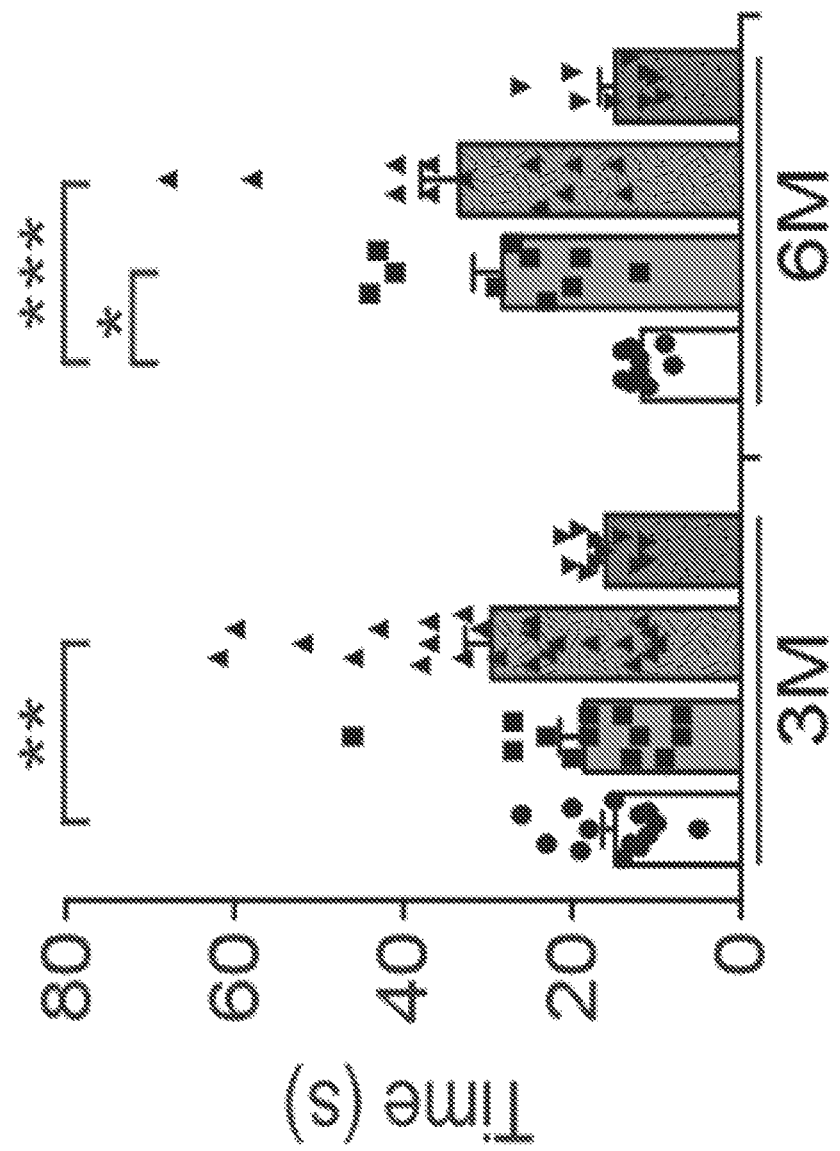
FIG. 32 shows behavioral abnormalities of PBS, α-syn PFF, PAR-α-syn PFF, or PAR-injected mice at 1, 3, and 6 months measured by pole test. Data are the means±s.e.m. One-way ANOVA followed by Tukey's post hoc test (n=9 to 14 mice per group).
Figure 33:
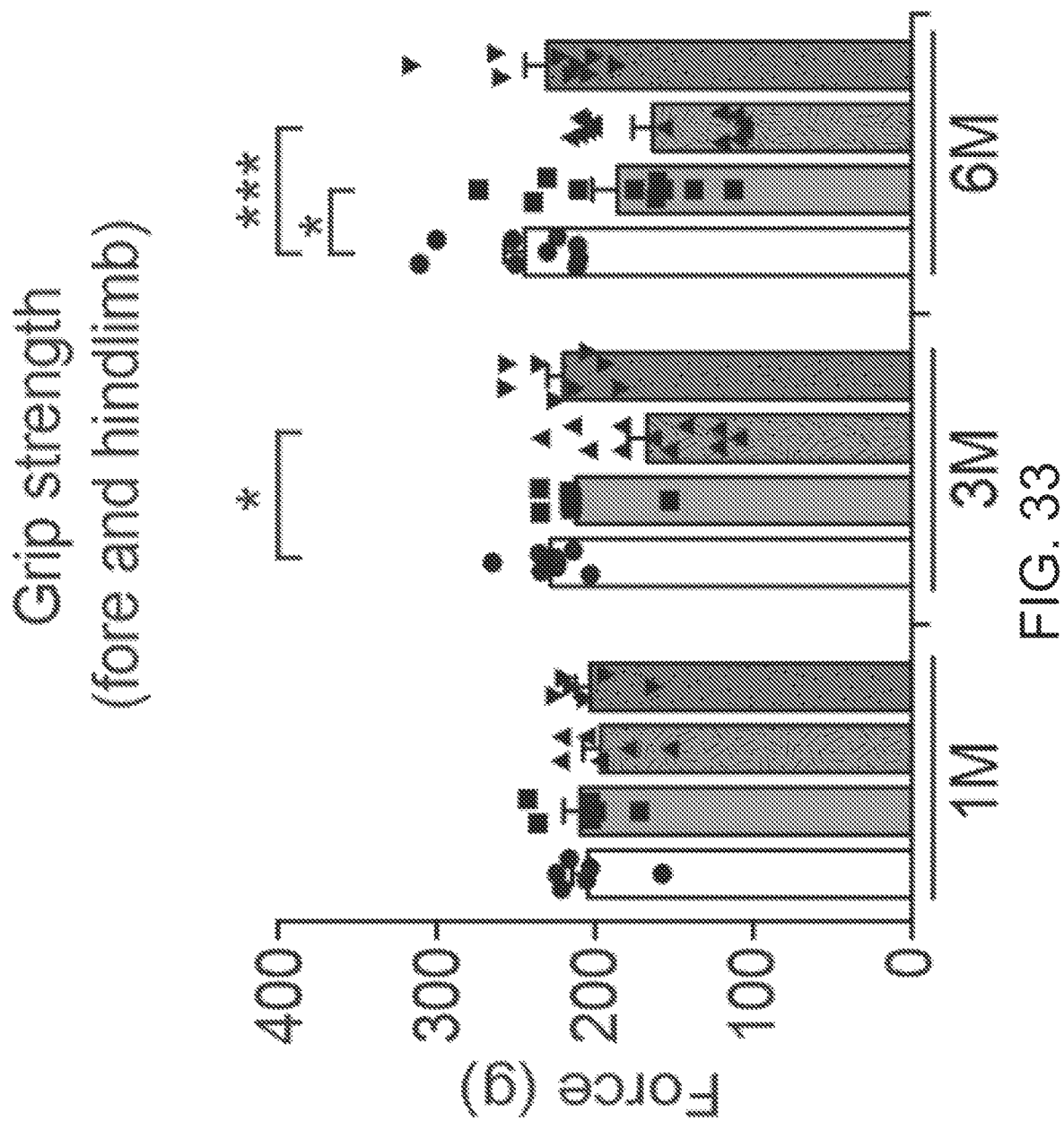
FIG. 33 shows behavioral abnormalities of PBS, α-syn PFF, PAR-α-syn PFF, or PAR-injected mice at 1, 3, and 6 months measured by grip strength test. Data are the means s.e.m. One-way ANOVA followed by Tukey's post hoc test (n=9 to 14 mice per group).
Figure 80:
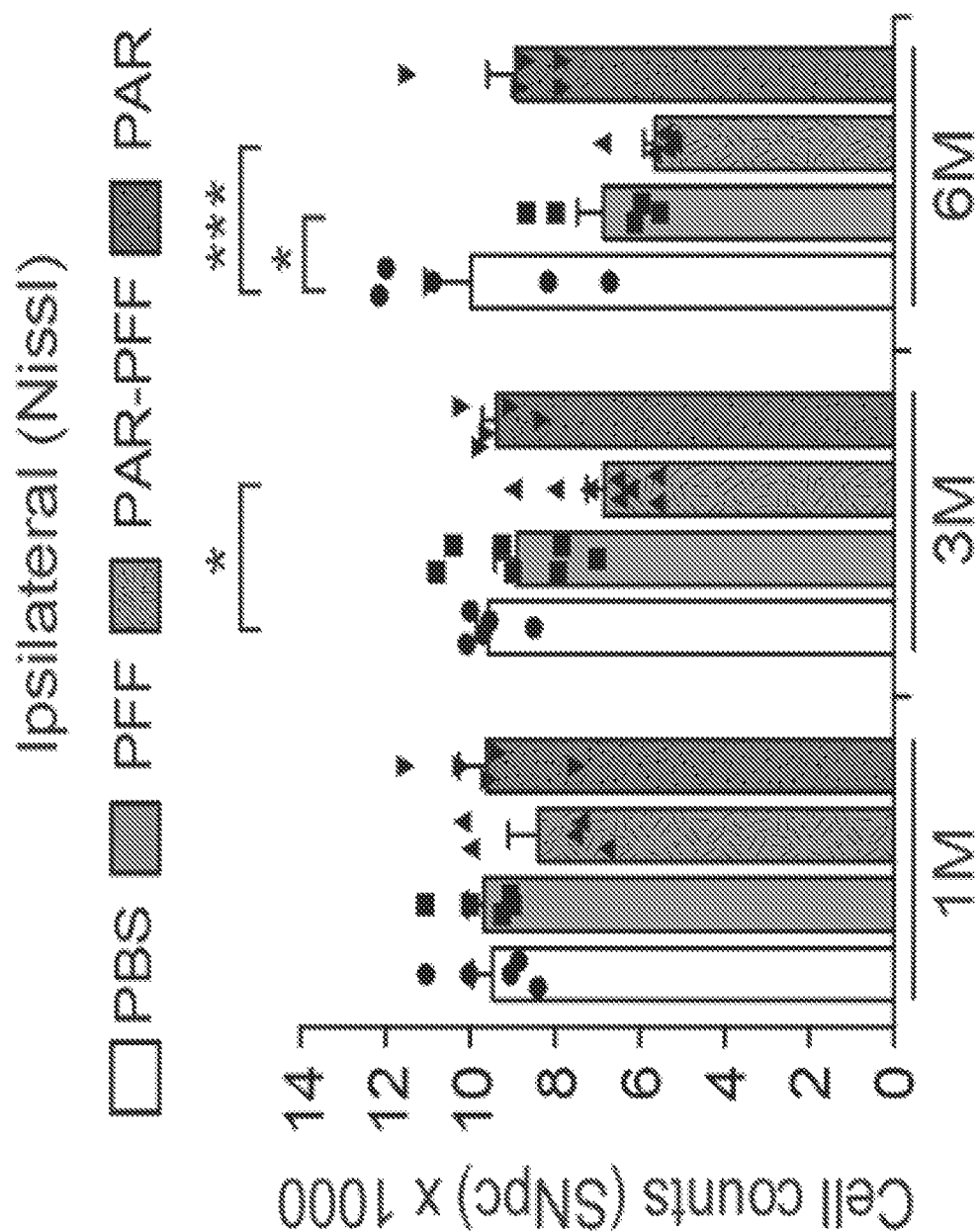
FIG. 80 shows stereological counts of SNpc DA neurons of WT mice at 1, 3, and 6 months after instrastriatal PBS, α-syn PFF, PAR-α-syn PFF, or PAR injection. (A) Ipsilateral Nissl-neurons were counted. Bars represent mean±s.e.m. One-way ANOVA followed by Tukey's post hoc test (n=5 to 8 mice per group). *$P<0.05$, ***$P<0.001$.
Figure 81:
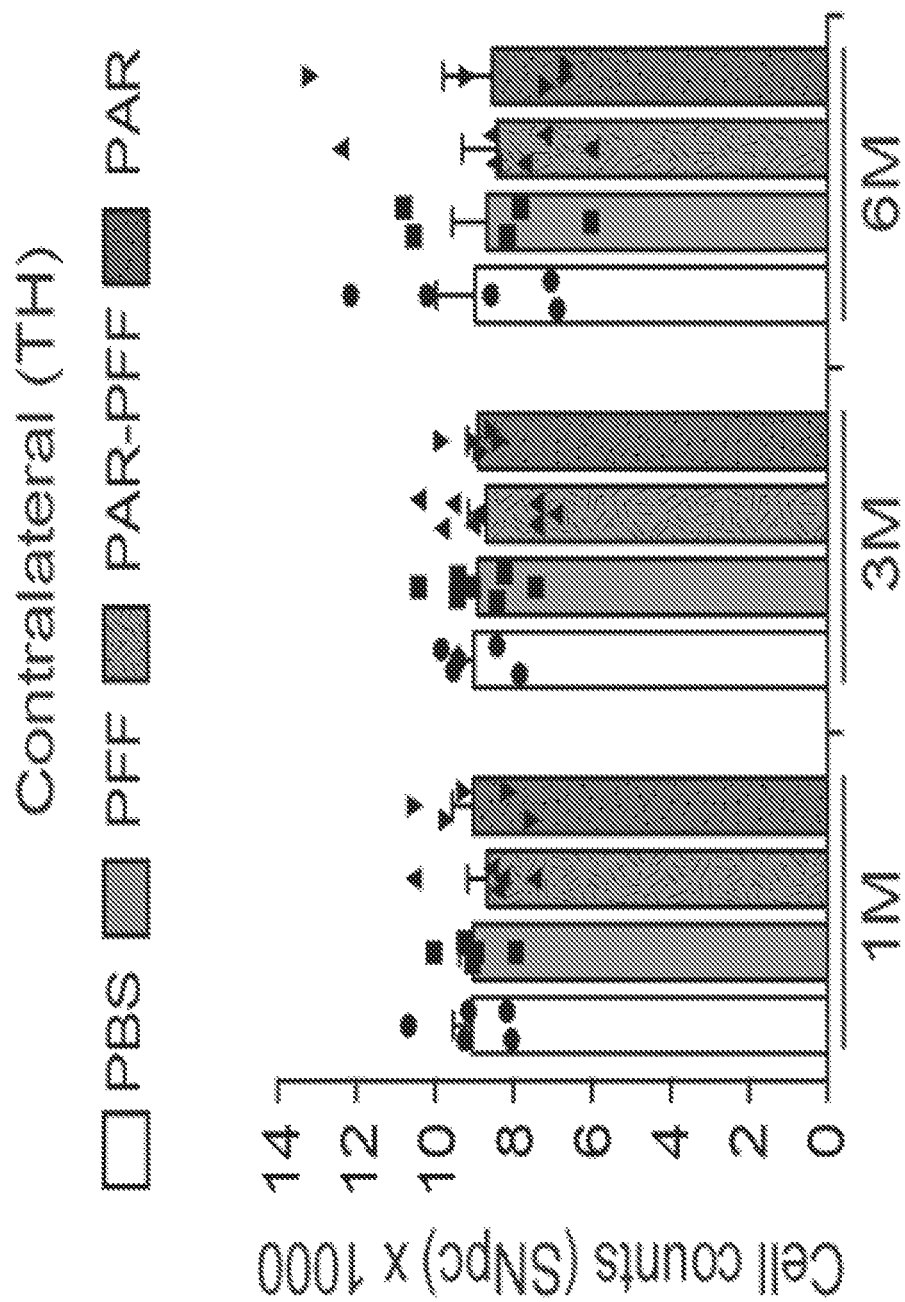
FIG. 81 shows stereological counts of SNpc DA neurons of WT mice at 1, 3, and 6 months after instrastriatal PBS, α-syn PFF, PAR-α-syn PFF, or PAR injection. contralateral TH-neurons were counted. Bars represent mean±s.e.m. One-way ANOVA followed by Tukey's post hoc test (n=5 to 8 mice per group). *$P<0.05$, ***$P<0.001$.
Figure 82:
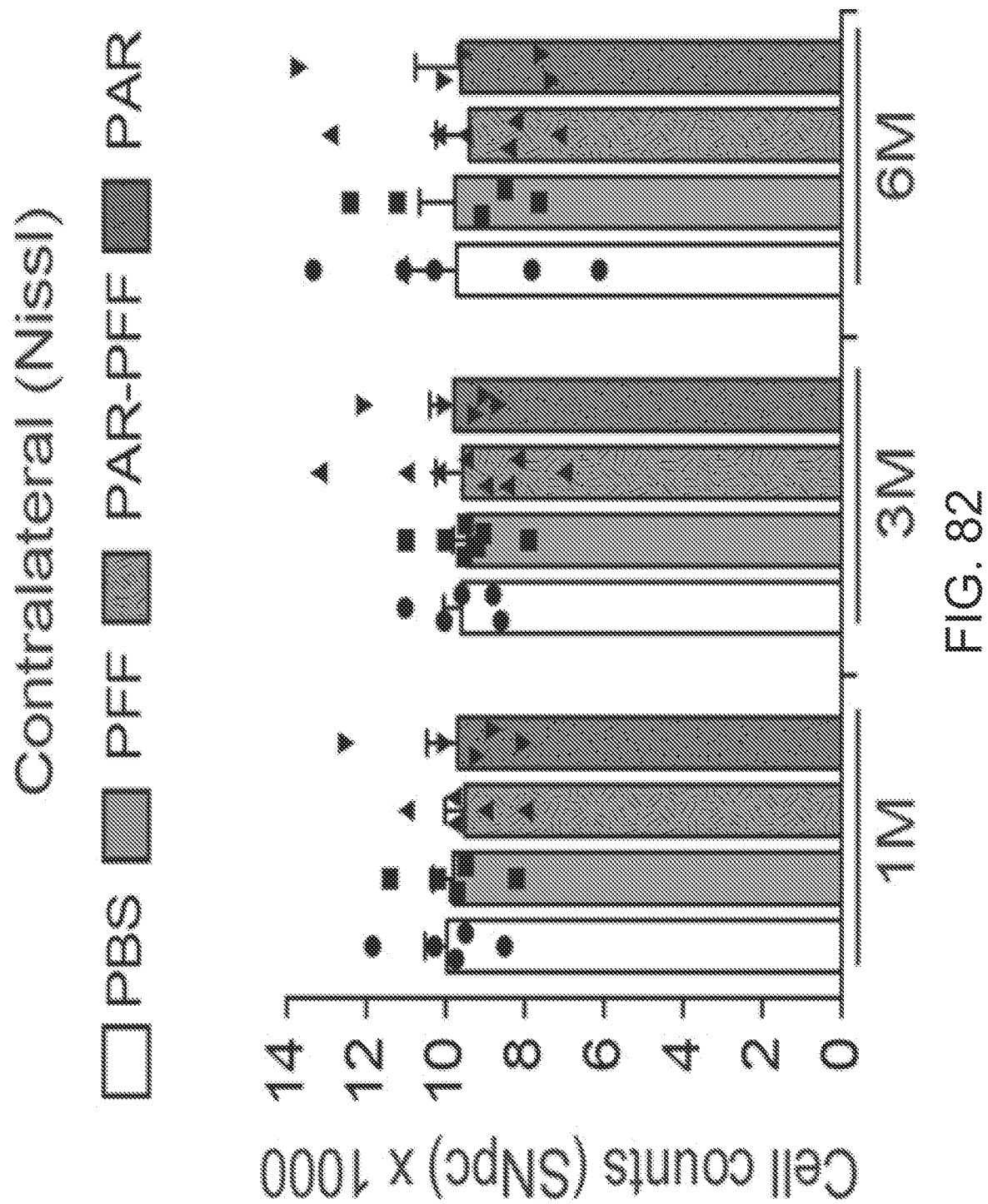
FIG. 82 shows stereological counts of SNpc DA neurons of WT mice at 1, 3, and 6 months after instrastriatal PBS, α-syn PFF, PAR-α-syn PFF, or PAR injection. Nissl-positive neurons were counted. Bars represent mean±s.e.m. One-way ANOVA followed by Tukey's post hoc test (n=5 to 8 mice per group). *$P<0.05$, ***$P<0.001$.
Figure 83:
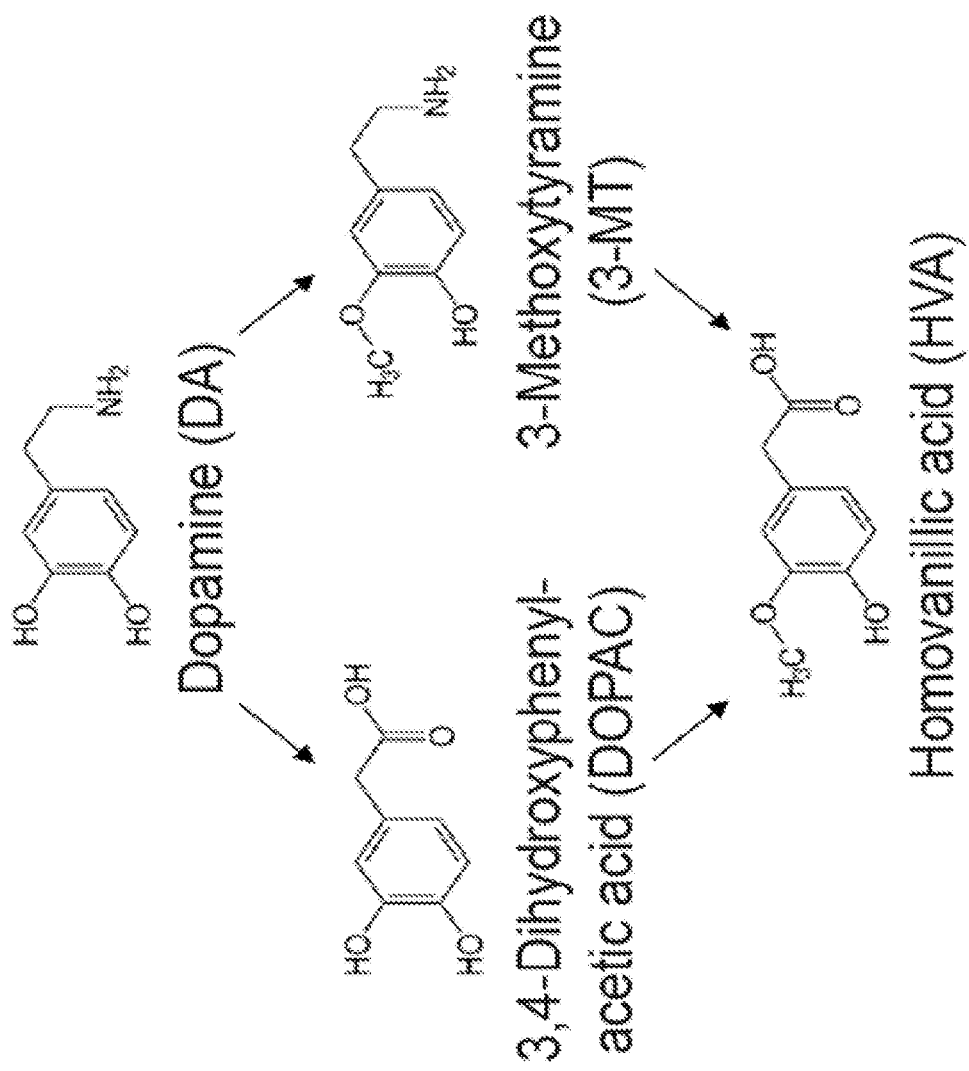
FIG. 83 shows a schematic diagram of dopamine metabolism.
Figure 84:
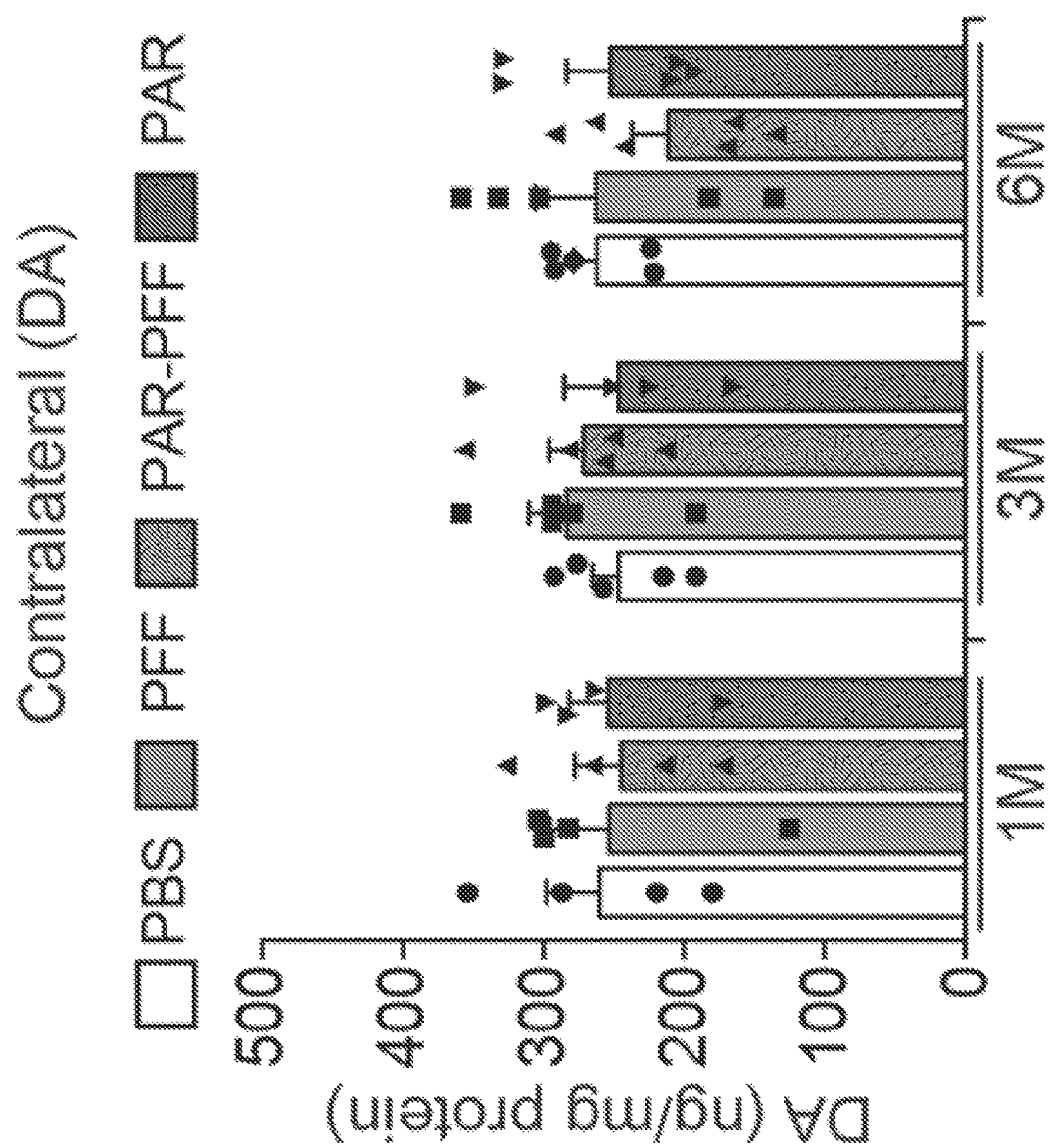
FIG. 84 shows no significant difference of DA concentration in the contralateral striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test.
Figure 85:
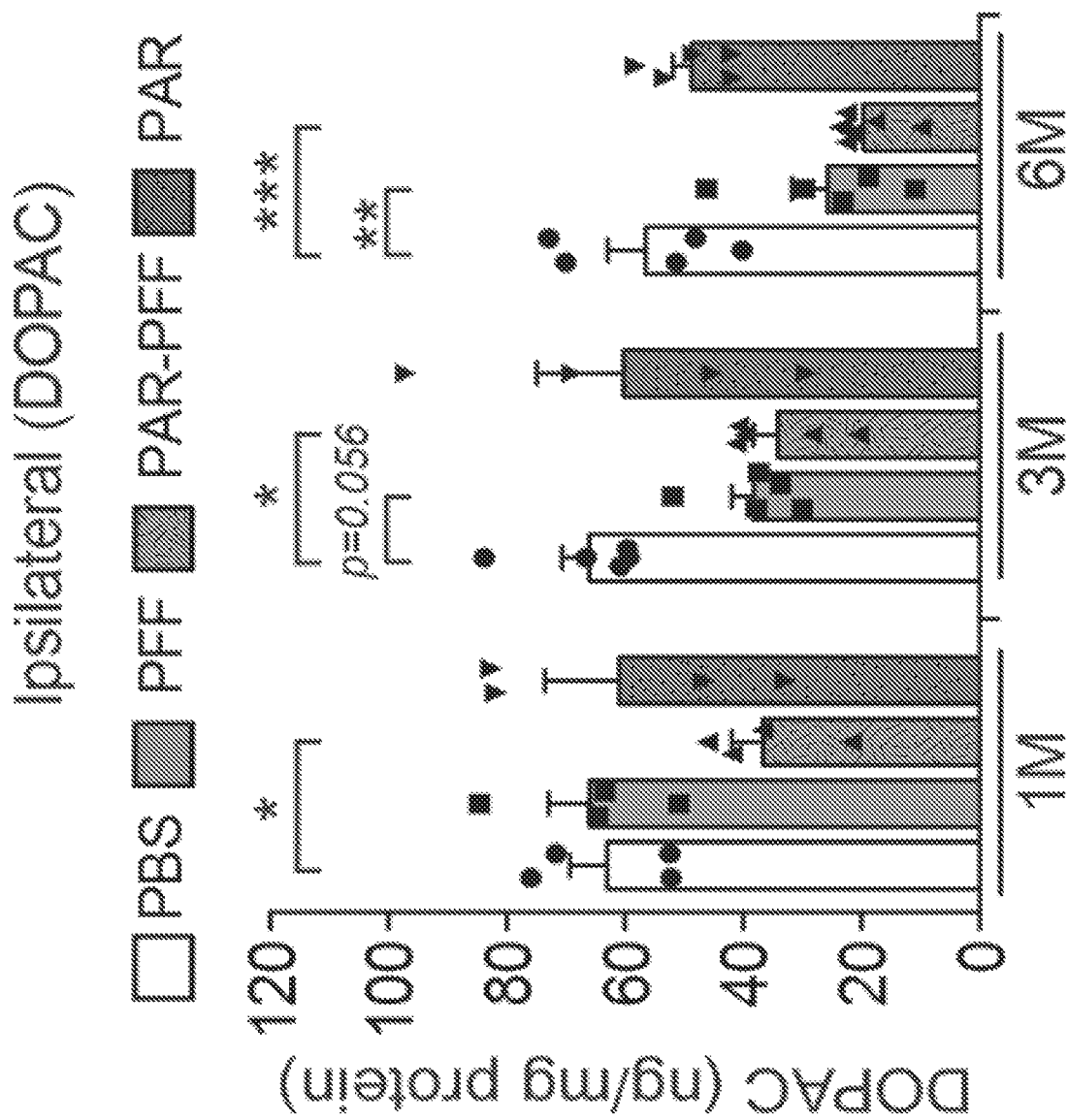
FIG. 85 shows ipsilateral DOPAC concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *$P<0.05$, $P<0.005$, *$P<0.001$.
Figure 86:
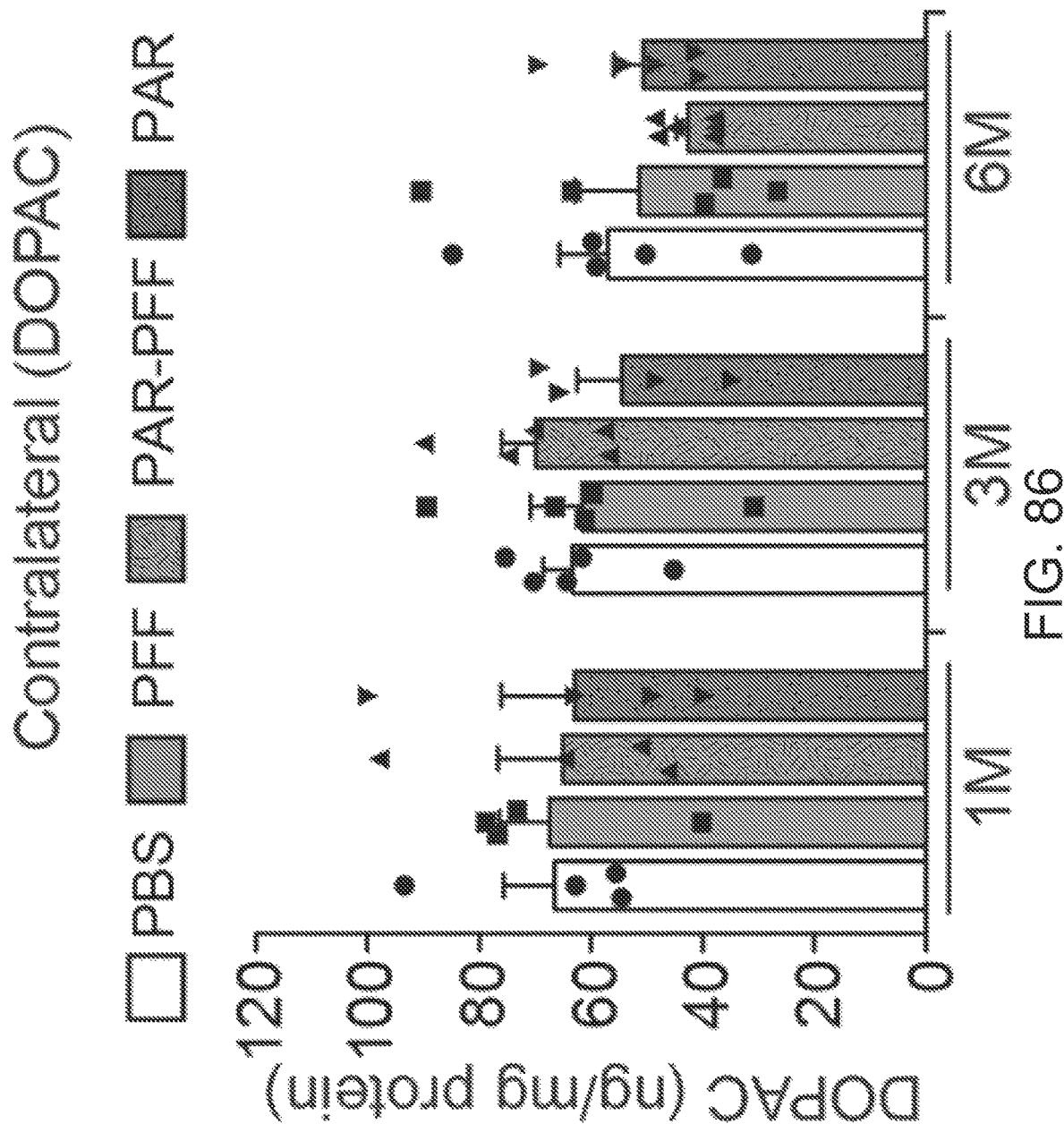
FIG. 86 shows contralateral DOPAC concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *$P<0.05$, $P<0.005$, *$P<0.001$.
Figure 87:
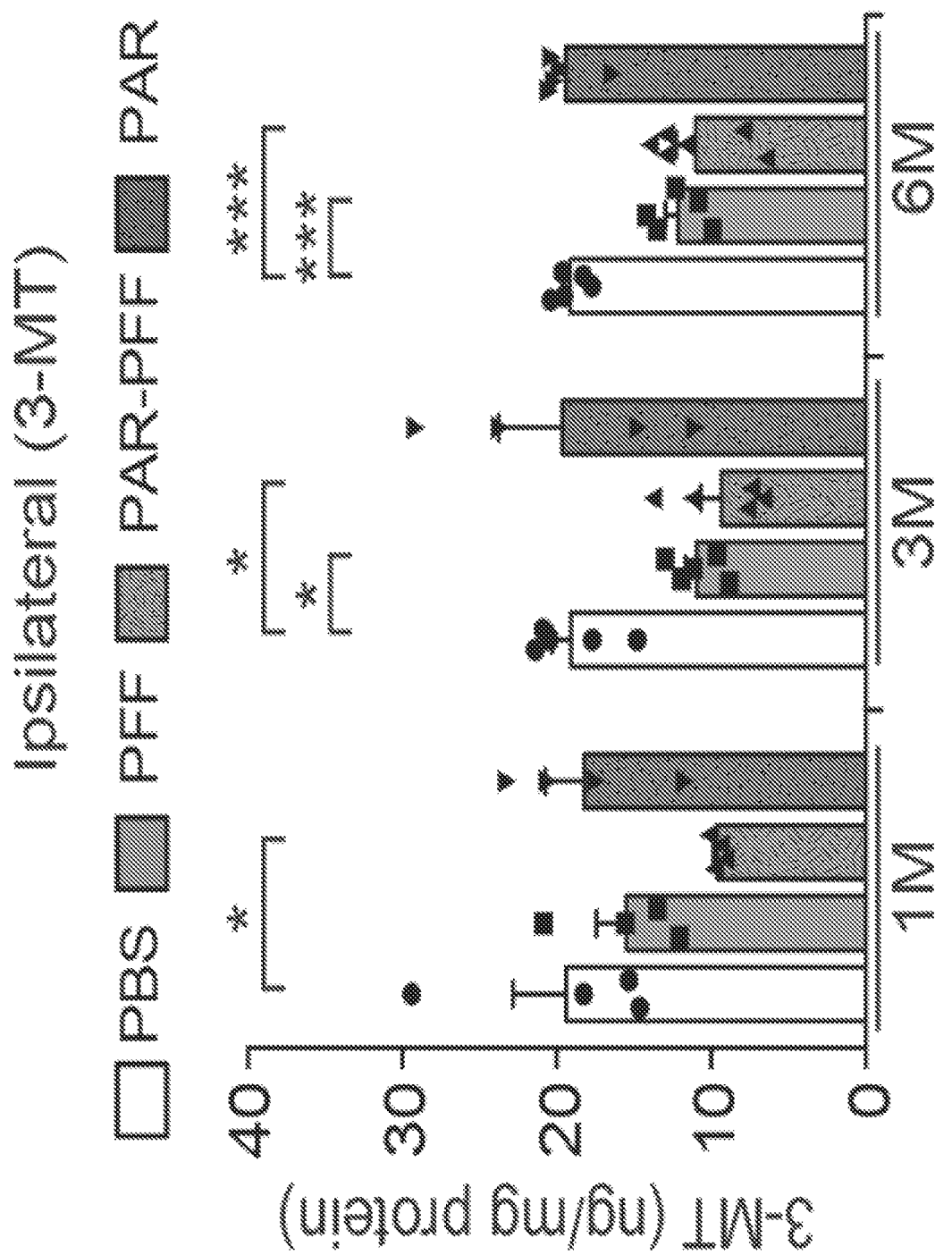
FIG. 87 shows ipsilateral 3-MT concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *$P<0.05$, $P<0.005$, *$P<0.001$.
Figure 88:
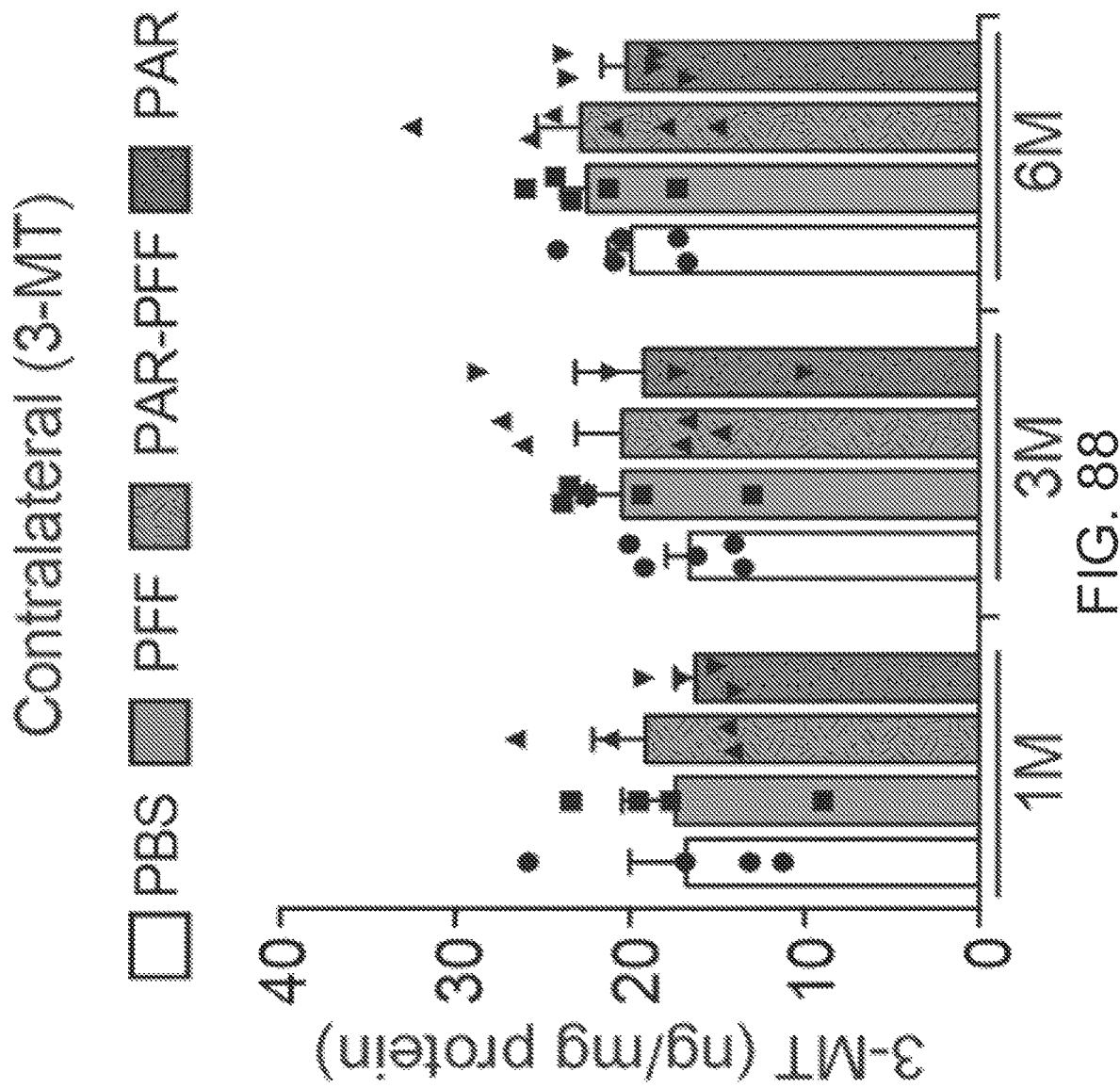
FIG. 88 shows contralateral 3-MT concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *$P<0.05$, $P<0.005$, *$P<0.001$.
Figure 89:
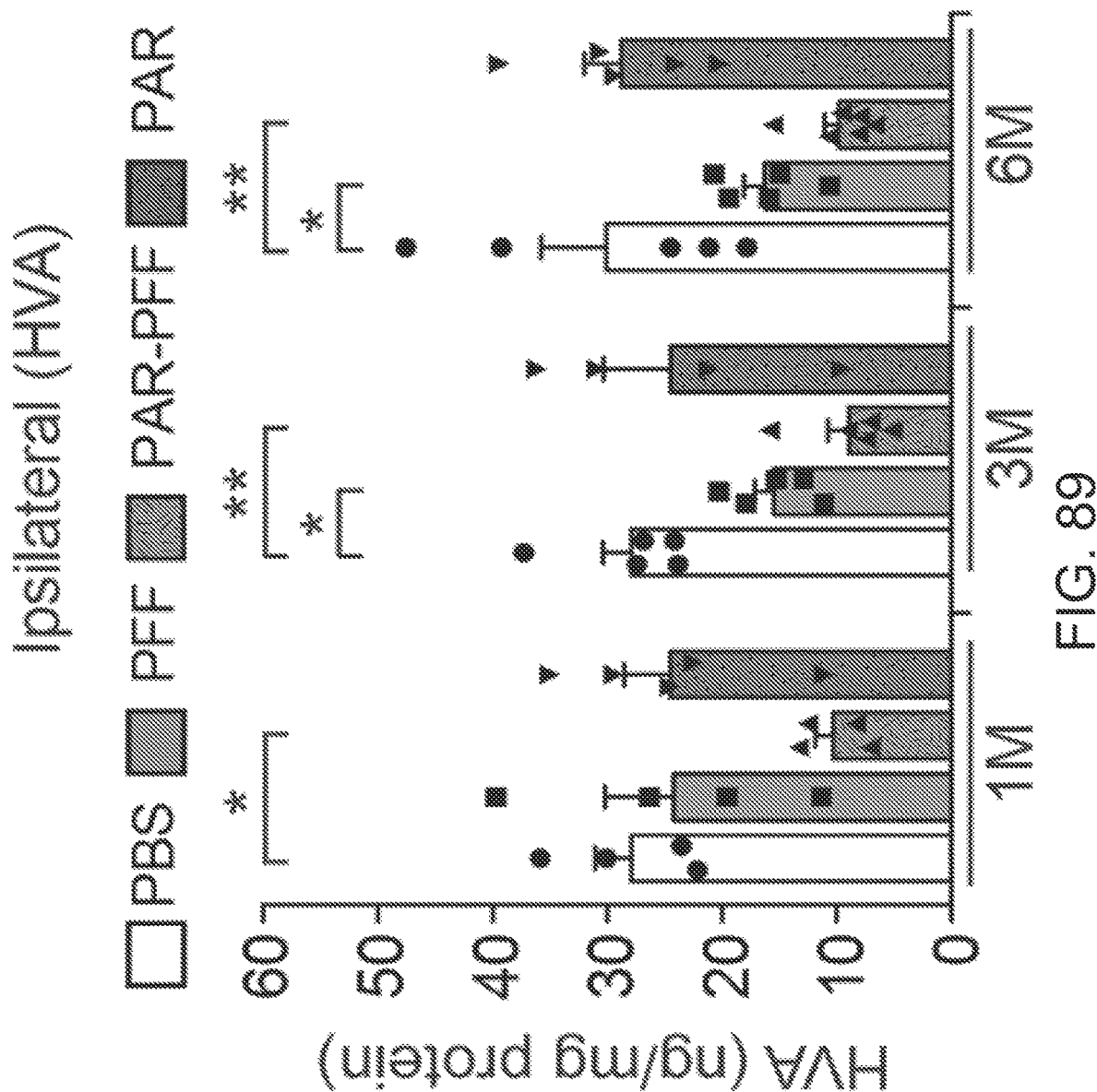
FIG. 89 shows ipsilateral HVA concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *$P<0.05$, $P<0.005$, *$P<0.001$.
Figure 90:
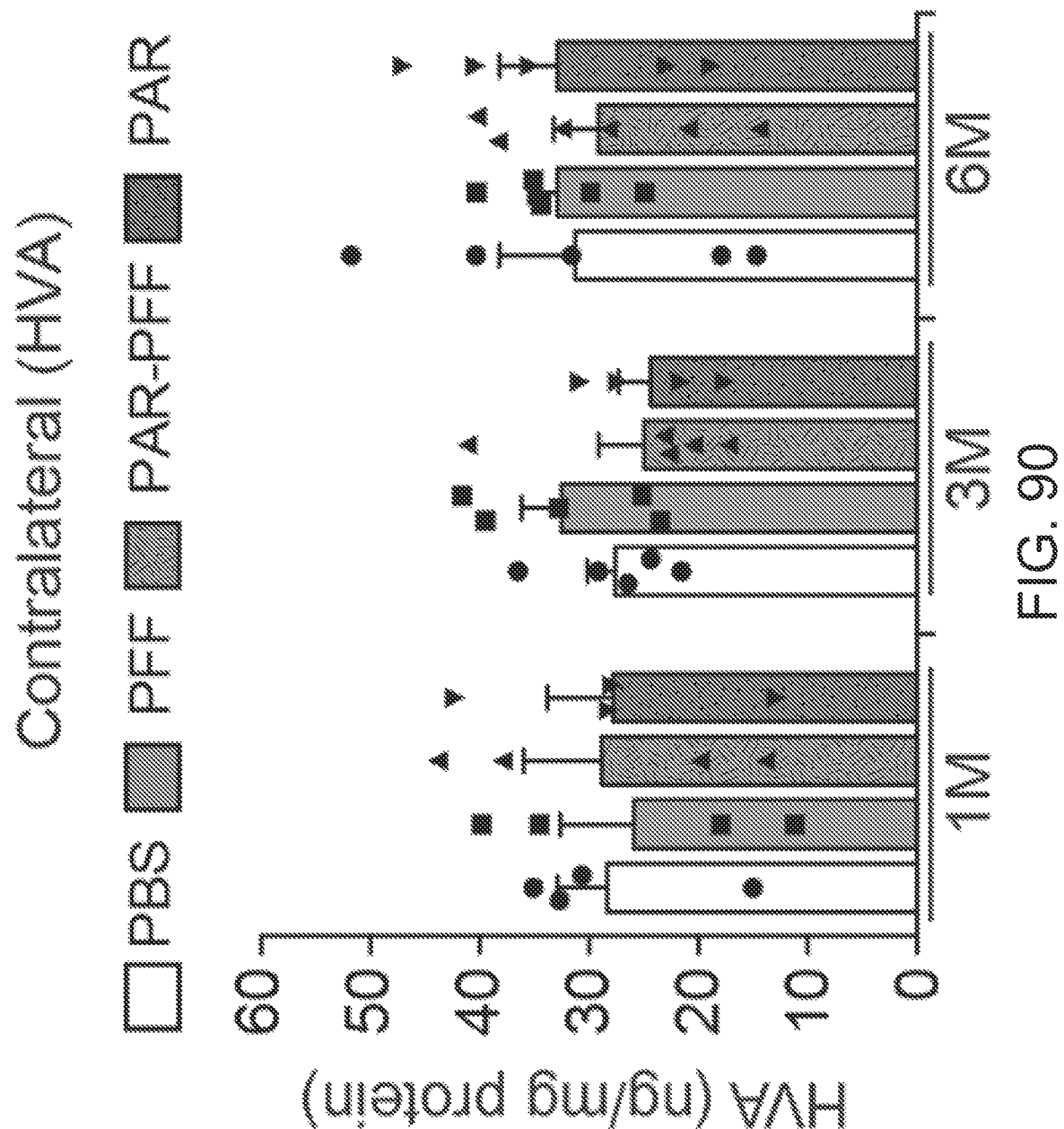
FIG. 90 shows contralateral HVA concentration in the striatum of PBS, α-syn PFF, PAR-α-syn PFF, or PAR-injected mice at 1, 3, and 6 months measured by HPLC. Bars represent mean±s.e.m. One-way ANOVA followed by Tukey's post hoc test (n=4 to 6 mice per group). *P<0.05, P<0.005, *P<0.001.
Figure 91:
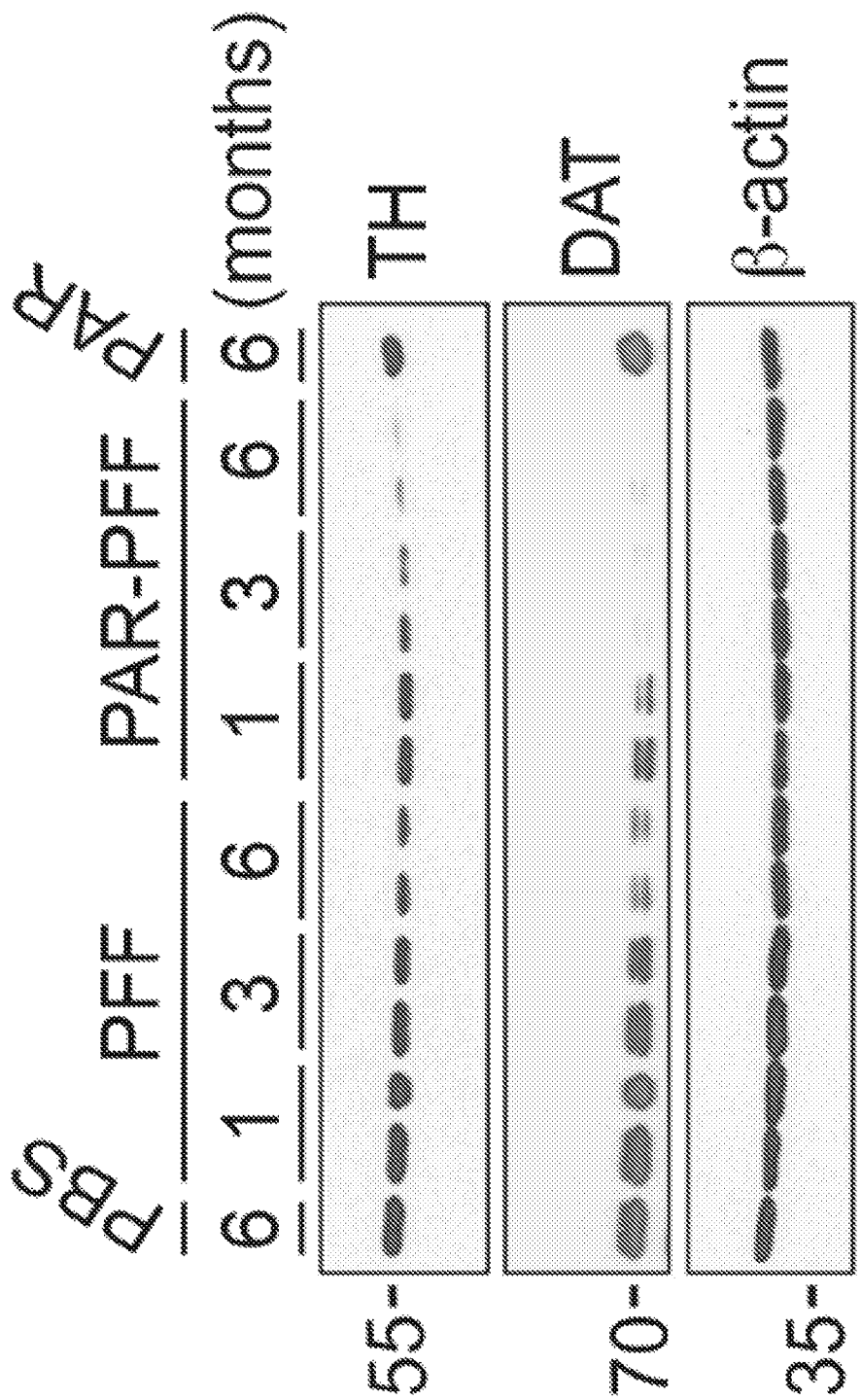
FIG. 91 shows representative immunoblots of TH, DAT, and β-actin in the striatum of PBS, α-syn PFF, PAR-α-syn PFF, or PAR-injected mice at 1, 3, and 6 months.
Figure 92:
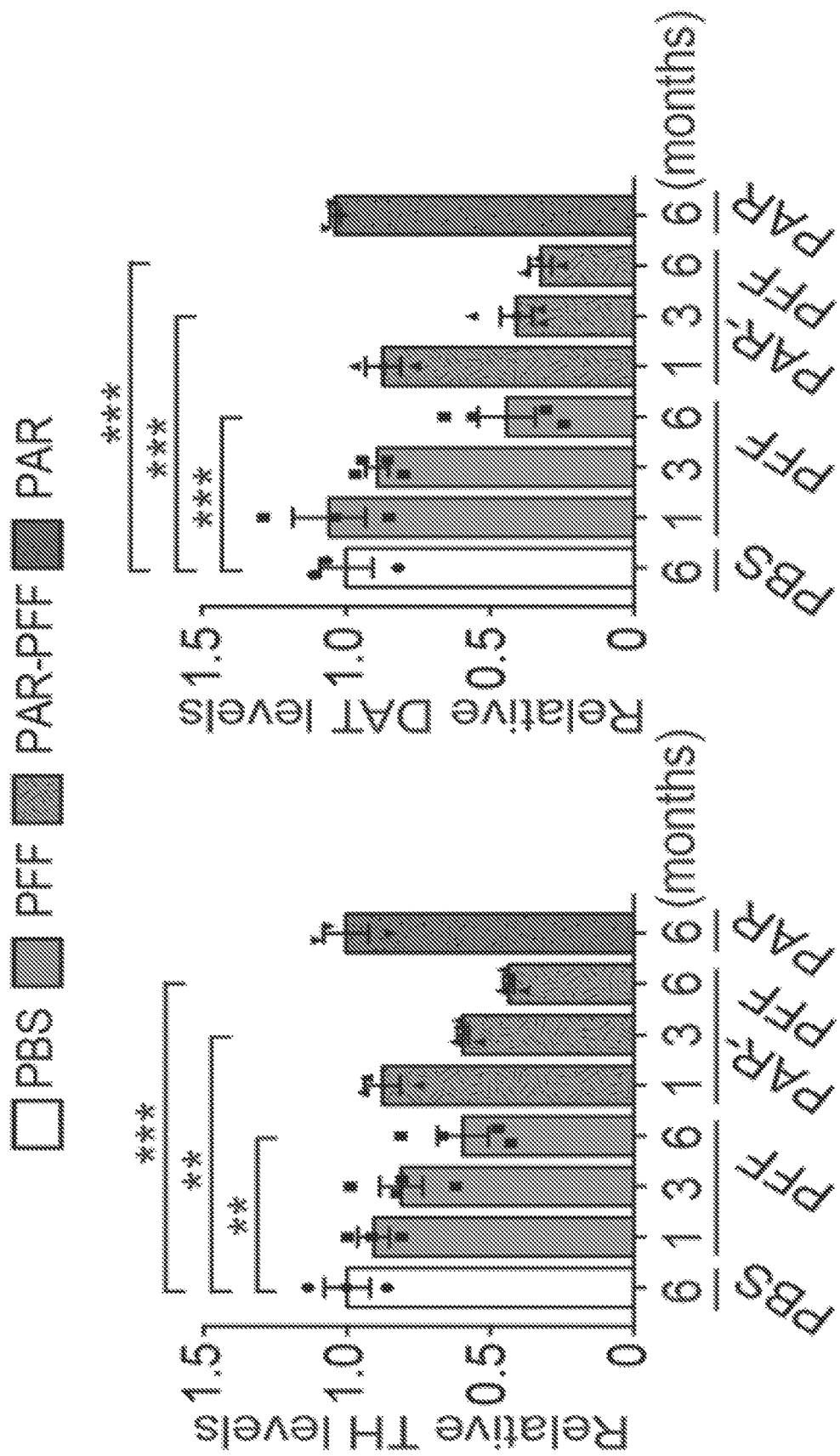
FIG. 92 shows quantification of TH and DAT levels in the striatum normalized to β-actin. Error bars represent the mean±s.e.m. One-way ANOVA followed by Tukey's post hoc test (n=3-4).
Figure 93:
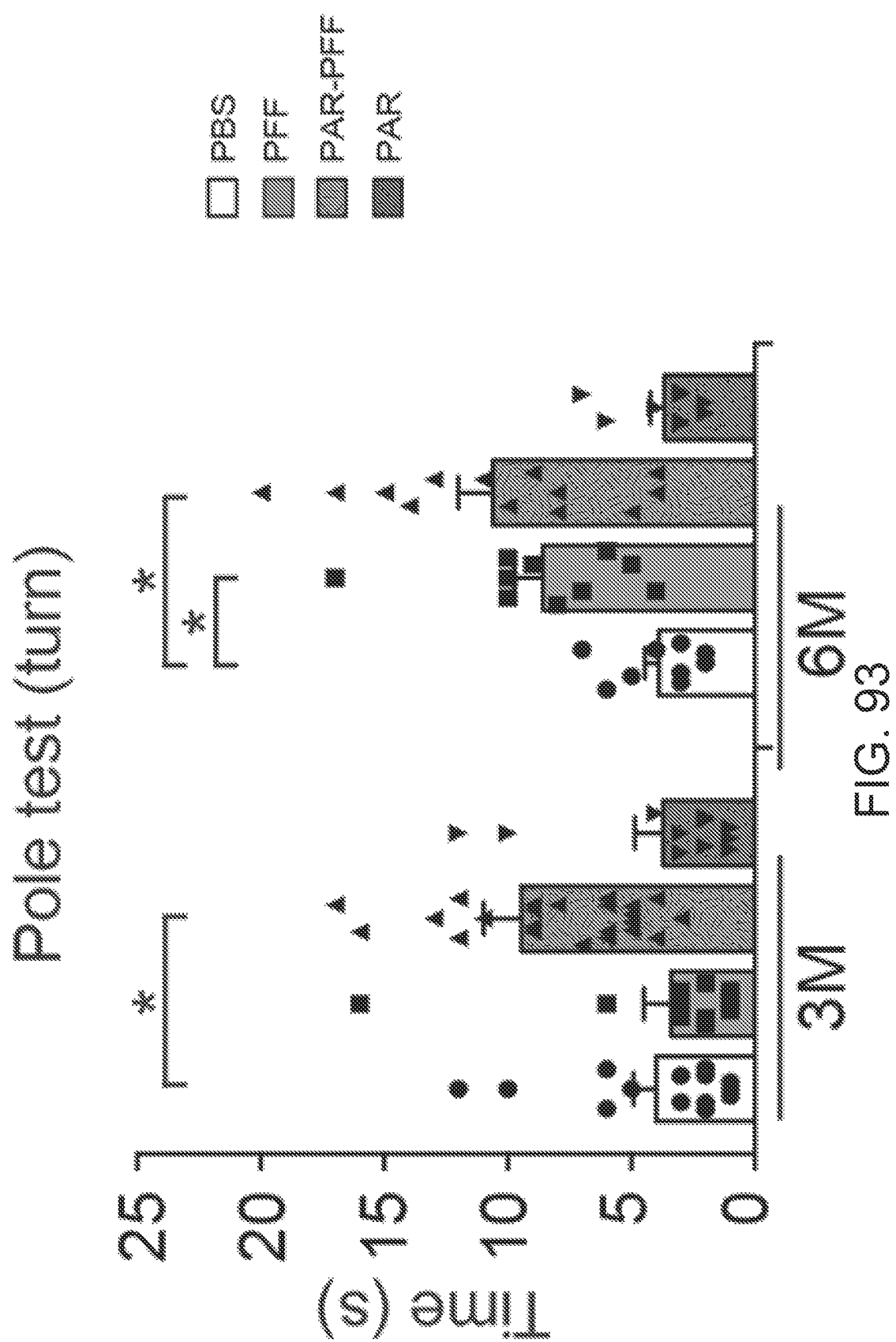
FIG. 93 shows behavioral abnormalities of PBS, α-syn PFF, PAR-α-syn PFF, or PAR-injected mice at 1, 3, and 6 months measured by pole test. Data are the means±s.e.m. One-way ANOVA followed by Tukey's post hoc test. *P<0.05, P<0.005, *P<0.001.
Figure 94:
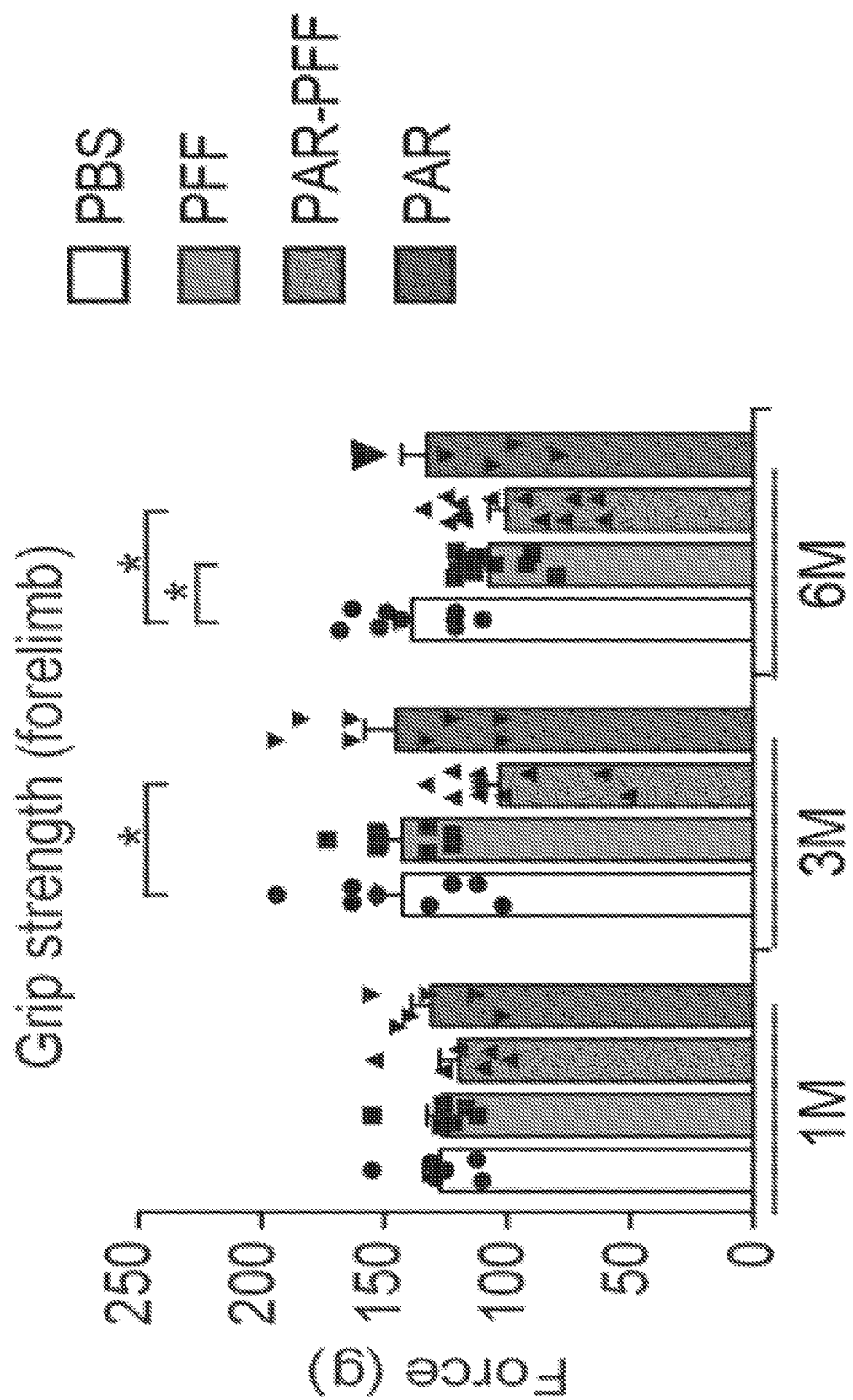
FIG. 94 shows behavioral abnormalities of PBS, α-syn PFF, PAR-α-syn PFF, or PAR-injected mice at 1, 3, and 6 months measured by grip strength test. Data are the means s.e.m. One-way ANOVA followed by Tukey's post hoc test. *P<0.05, P<0.005, *P<0.001.

To determine whether the PAR-α-syn PFF strain exhibits enhanced neurotoxicity in vivo, a single intrastriatal injection of PAR-α-syn PFF (5 μg) was compared to that of α-syn PFF (5 μg). There is trend toward the loss of DA neurons ipsilateral to the injection side of SNpc after one month and a significant loss of DA neurons after 3 months following PAR-α-syn PFF injection, while α-syn PFF injection has no effect at these time points (FIGS. 27, 28 and 80). Six months after PAR-α-syn PFF or α-syn PFF injection there is no significant difference in the loss of DA neurons (FIGS. 27, 28 and 80). There is no significant loss of DA neuron contralateral to the injection side at any time point (FIGS. 81 and 82). PAR injection by itself has no effect on DA neuron number (FIGS. 27, 28, and 80). PAR-α-syn PFF also accelerate the loss of striatal DA and its metabolites as determined by HPLC with significant reductions in DA and its metabolites being observed 1 month after the PAR-α-syn PFF injection in contrast to α-syn PFF (FIGS. 29 and 83 to 90). Three and 6 months after PAR-α-syn PFF or α-syn PFF injection there is no significant difference in the loss of DA and its metabolites (FIGS. 29 and 83 to 90). TH and DAT levels are also reduced after PAR-α-syn PFF compared to α-syn PFF as determined by western blot analysis three months after the injection, while there is no difference in the degree of loss at 6 months (FIGS. 91 to 94). α-syn pathology as assessed by immunostaining for p-α-syn in DA neurons was increased by PAR-α-syn PFF compared to α-syn PFF at 3 months and 6 months after injection (FIGS. 30 and 31). PAR-α-syn PFF caused a deficit on the pole test at 3 months consistent with loss of DA neurons and DA deficits at 3 months, whereas there are no significant deficits in α-syn PFF or PAR injected mice (FIGS. 32 and 93). Both forelimb plus hindlimb and forelimb grip strength were also reduced in PAR-α-syn PFF, but not α-syn PFF or PAR inject mice at 3 months (FIGS. 33 and 94). At 6 months there is no significant difference in the behavioral deficits induced by PAR-α-syn PFF or α-syn PFF (FIGS. 32, 33, 92 and 94). Taken together, these results indicate that PAR-α-syn PFF are substantially more neurotoxic then α-syn PFF in vivo.

Figure 34:
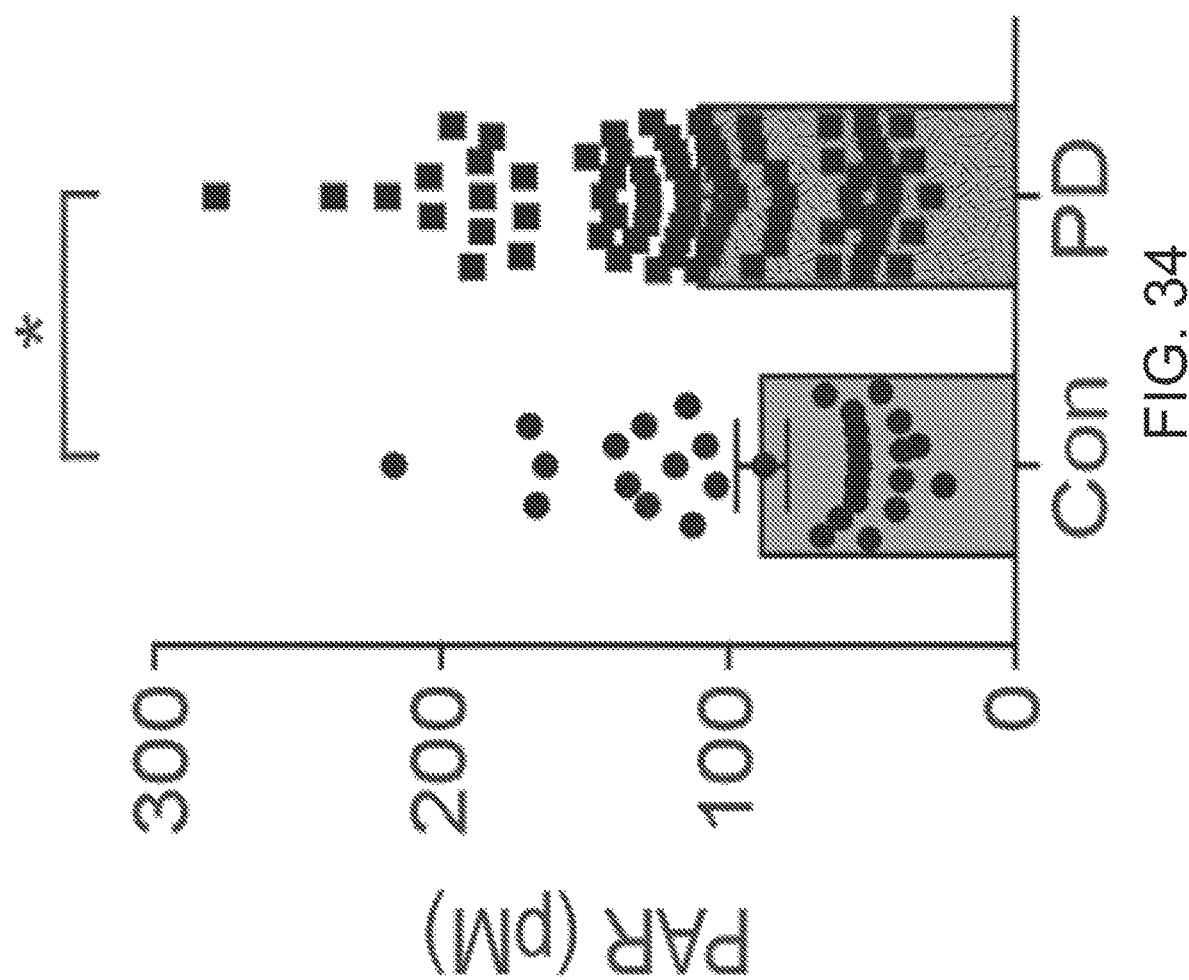
FIG. 34 shows increase of PAR in CSF of PD patients. The levels of PAR in CSF of healthy controls (n=31) and PD patients (n=80) were determined by PAR ELISA. Bars represent mean±s.e.m. Student t test with Welch's correction.
Figure 35:
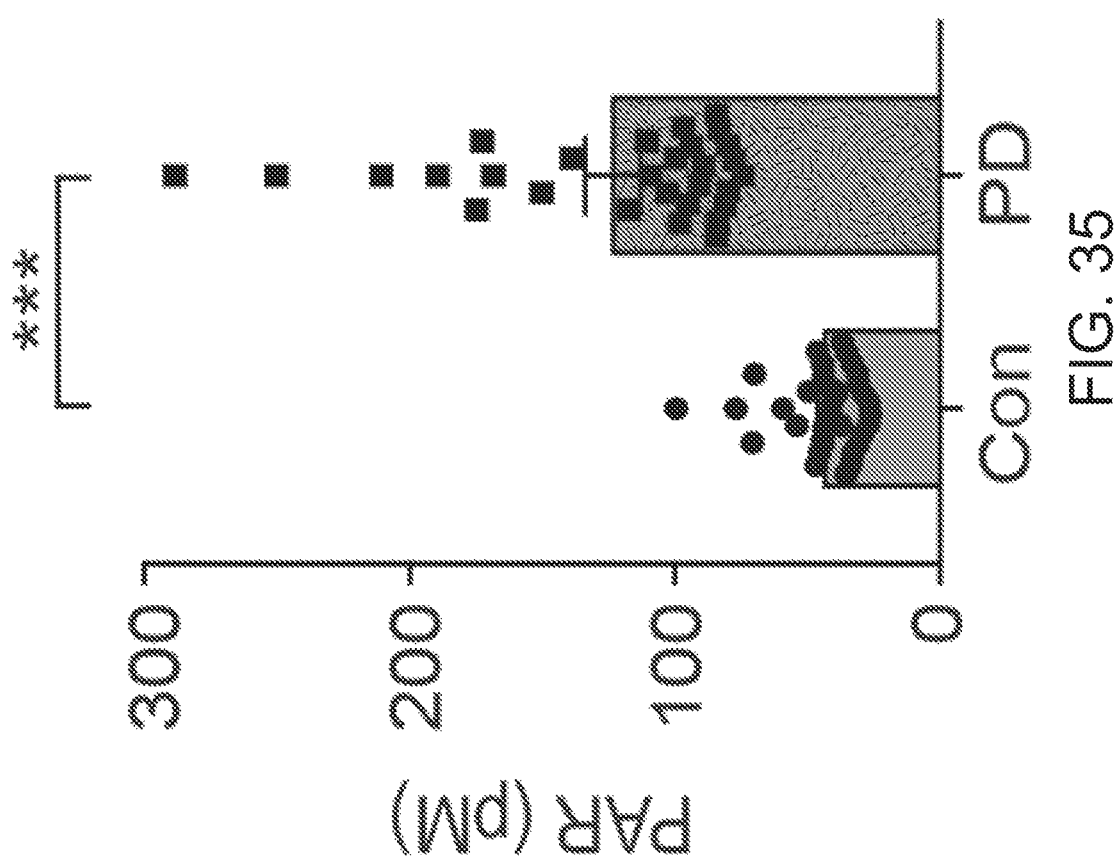
FIG. 35 shows increase of PAR in CSF of PD patients. The levels of PAR in CSF of healthy controls (n=33) and PD patients (n=21) were determined by PAR ELISA. Bars represent mean±s.e.m. Student t test with Welch's correction.
Figure 36:
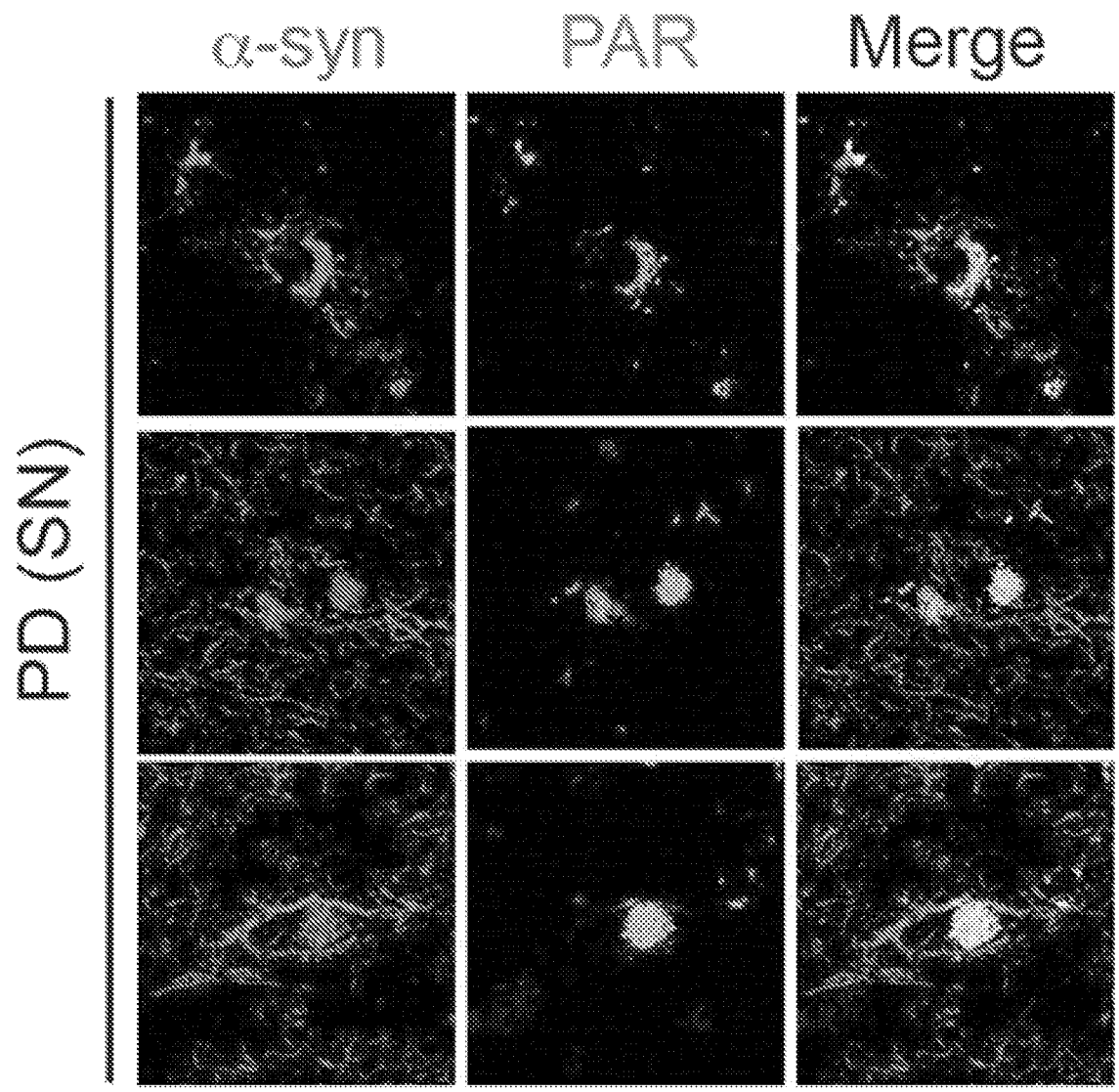
FIG. 36 shows increase and co-localization of PAR in Lewy body of PD patients. Representative α-syn (red) and PAR (green) immunostaining in the SNpc of PD patients.
Figure 95:
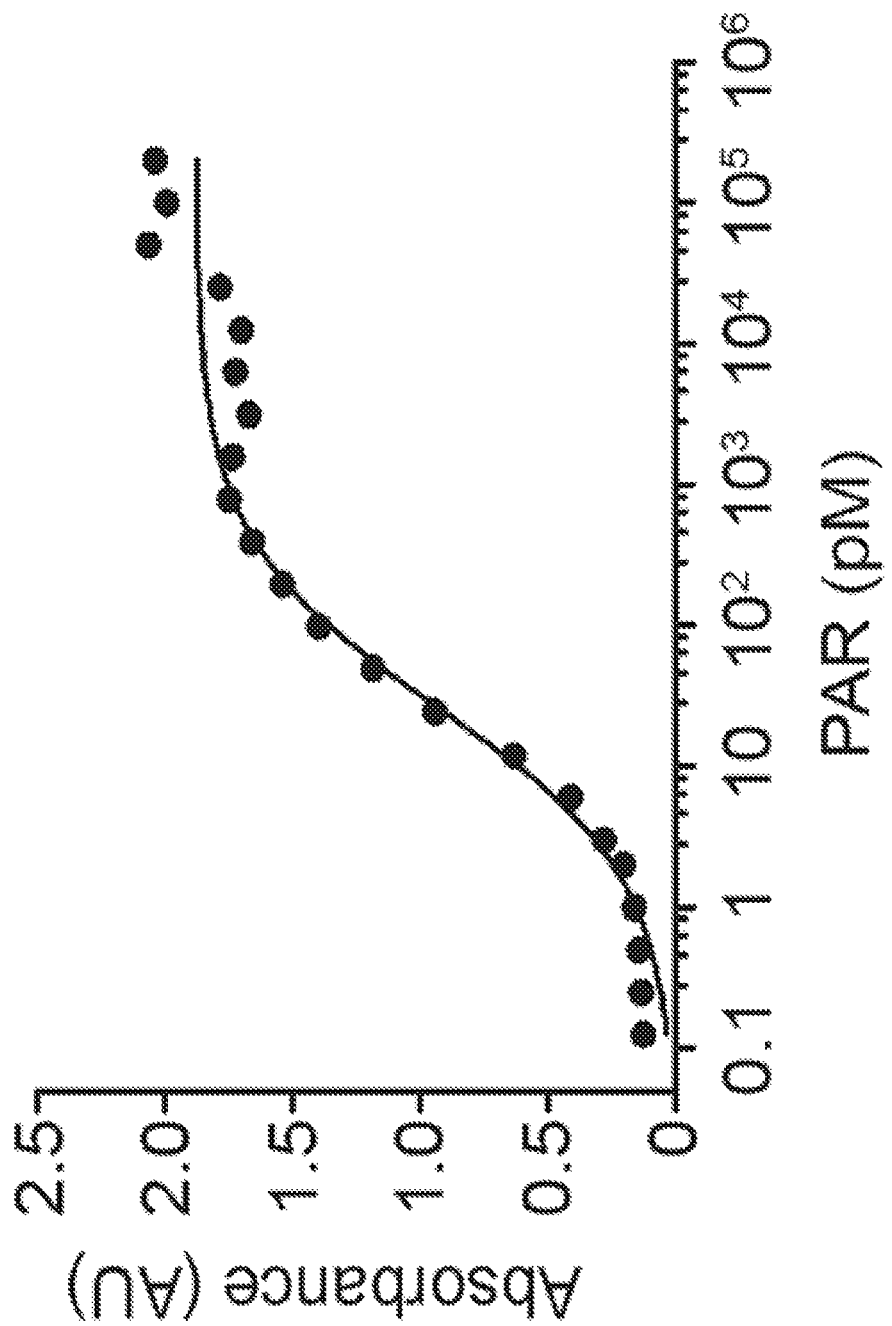
FIG. 95 shows establishment of PAR ELISA. ELISA detected the PAR as low as 3 pM and was saturated at 50 nM.
Figure 96:
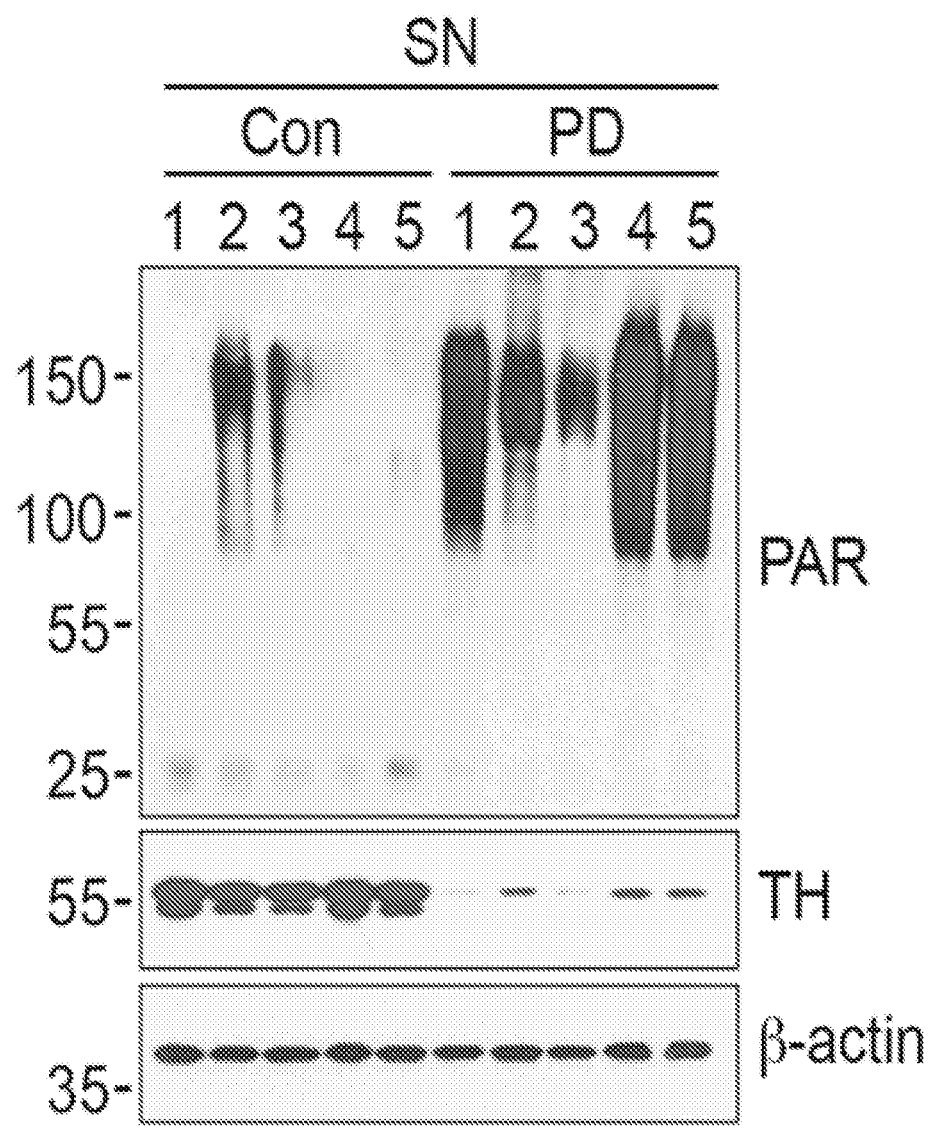
FIG. 96 shows representative immunoblots of PAR, TH, and β-actin in the substantia nigra of control and PD patients.
Figure 97:
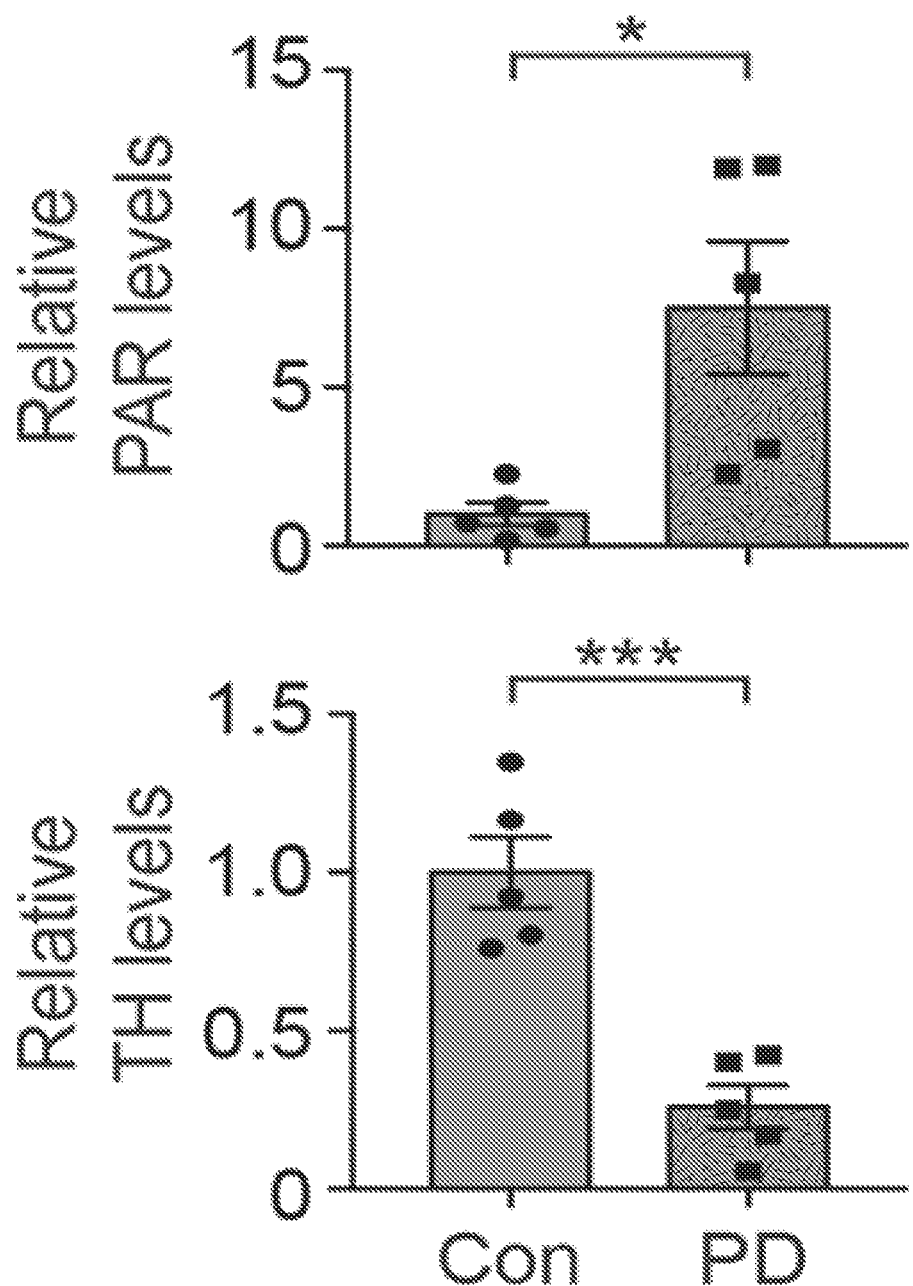
FIG. 97 shows quantification of PAR and TH levels normalized to β-actin. Error bars represent the mean±s.e.m. One-way ANOVA followed by Tukey's post hoc test (n=5). *P<0.05, ***P<0.001.

To determine whether PAR plays a role in patients with PD, PAR levels were monitored in the CSF of patients with PD versus controls (Table 1) using a sensitive ELISA for PAR (FIG. 95). PAR levels are elevated in PD patients compared to controls in two independent patient cohorts (FIGS. 34 and 35). As previously reported, PAR levels are increased in the substantia nigra of patients with PD compared to controls (FIGS. 96 and 97, and Table 2). PAR immunoreactivity is colocalized with α-syn in Lewy Bodies of PD patients (FIG. 36).

The results indicate that α-syn PFF kills neurons both in vitro and in vivo via activation of PARP-1 in a cell death process designated parthanatos. Knockout of PARP-1 and inhibition of PARP prevents the neurodegeneration and behavioral deficits initiated by an intrastriatal α-syn PFF injection. Activation of parthanatos seems to be the primary driver of α-syn PFF neurodegeneration since necroptosis and autophagy inhibitors have no effect on α-syn PFF neurotoxicity and there is only modest protection by caspase inhibition. It is known that α-syn PFF induce inflammatory mediator activation, which likely contributes, in part, to cell death and accounts for the modest neuroprotection by the broad spectrum caspase inhibitor, ZVAD.

Recent studies have identified conformational variants of α-syn strains that exhibit distinct neurotoxicity, seeding abilities and propagation, which contribute to different properties of α-synucleinopathies. Given that α-syn PFF induces PARP activation and PAR accumulation, PAR then accelerates α-syn fibrillization and changes the biochemical properties of α-syn PFF converting it to a more toxic strain. Consistent with this notion are observations that PAR-α-syn PFF shows an approximate 25 fold increase in α-syn aggregation and neurotoxicity compared to the parental α-syn PFF. Moreover PAR-α-syn PFF-injected mice show an accelerated disease progression and phenotype compared to α-syn PFF injected mice. In addition to PAR levels being increased in cultured neurons and mouse brain, it was observed that PAR levels in PD are elevated not only in the substantia nigra, but also the CSF. The elevation of PAR in the CSF and brains of PD patients and evidence of PARP activation in the substantia nigra of PD patients suggests that PARP activation contributes to the pathogenesis of PD through parthanatos and conversion of α-syn to a more toxic strain.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Animals

C57BL/6 mice were obtained from the Jackson Laboratories (Bar Harbor, ME). PARP-1 KO mice were obtained from The Jackson Laboratory (Bar Harbor, ME, USA). The littermates of WT and PARP1 KO mice were used in experiments. All housing, breeding, and procedures were performed according to the NIH Guide for the Care and Use of Experimental Animals and approved by Johns Hopkins University Animal Care and Use Committee.

Preparation of α-syn PFF and PAR-α-syn PFF

Recombinant mouse α-syn proteins were purified. α-syn PFF were prepared in PBS by constantly agitating α-syn with a thermomixer (1,000 rpm at 37° C.) (Eppendorf). After 7 days of incubation, the α-syn aggregates were diluted to 0.1 mg/ml with PBS and sonicated for 30 s (0.5 sec pulse on/off) at 10% amplitude (Branson Digital Sonifier, Danbury, CT, USA). The α-syn PFF were kept at −80° C. until use. Synthesis and purification of PAR polymer were performed as described elsewhere. PAR-α-syn PFF was prepared by adding 5 nM or indicated dose of PAR in α-syn fibrillization reaction.

Stereotaxic Injection of α-Syn PFF

Two to 3-month-old WT and PARP1 KO mice were deeply anesthetized with a mixture of ketamine (100 mg/kg) and xylazine (10 mg/kg). PBS, α-syn PFF, PAR-α-syn PFF or PAR was unilaterally injected into striatum (2 μl per hemisphere at 0.4 μl/min) with the following coordinates: anteroposterior (AP)=+2.0 mm, mediolateral (ML)=±2.0 mm, dorsoventral (DV)=+2.8 mm from bregma. After the injection, the needle was maintained for an additional 5 min for a complete absorption of the solution. After surgery, animals were monitored and post-surgical care was provided. Behavioral tests were performed 1, 3 and 6 months after injection and mice were euthanized for biochemical and histological analysis. For biochemical studies, tissues were immediately dissected and frozen at −80° C. For histological studies, mice were perfused with PBS and 4% PFA and brains were removed, followed by fixation in 4% PFA overnight and transfer to 30% sucrose for cryoprotection.

Thioflavin T (ThT) Binding Assay

α-syn fibrillization with or without PAR was monitored with ThT fluorescence. Aliquots of 5 μL from the incubation mixture were taken at various time points, diluted to 100 μL with 25 μM ThT in PBS, and incubate for 10 min at room temperature. The fluorescence was recorded at 450 nm excitation and 510 nm emission using SpectraMax plate reader (Molecular Devices, Sunnyvale, CA). The experiments were performed in triplicate.

Transmission Electron Microscopy (TEM) Measurements

α-syn PFF or PAR-α-syn PFF were adsorbed to glow discharged 400 meshed carbon coated copper grids (Electron Microscopy Sciences) for 2 min, quickly washed twice with Tris-HCl (50 mM, pH 7.4), and floated upon two drops of 0.75% uranyl formate for 30 s each. The grids were allowed to dry before imaging on a Phillips CM 120 TEM operating at 80 kV. The images were captured and digitized with an ER-80 CCD (8 megapixel) by advanced microscopy techniques.

Intracellular Delivery of PAR

Purified PAR was intracellularly delivered using BioPORTER (Genelnatis, San Diego, CA) according to the manufacturer's instructions. PAR polymer was diluted to desired concentration with PBS. The diluted solution was added to the dried BioPORTER reagent and mixed gently, followed by incubation at room temperature for 5 min. The BioPORTER-PAR complex was added to cell culture after a wash in serum-free media and incubated for 3-4 h at 37° C. Cultures were subsequently used for experiments.

Tissue Lysate Preparation and Western Blot Analysis

Human post mortem brain (Table 1) or mouse brain tissue were homogenized and prepared in lysis buffer [50 mM Tris-HCl (pH 7.4), 150 mM NaCl, 1 mM EDTA, 1% TRITON® x-100 (surfactant), 0.5% SDS, 0.5% sodium-deoxycholate, phosphatase inhibitor mixture I and II (Sigma-Aldrich, St. Louis, Mo., USA), and complete protease inhibitor mixture (Roche, Indianapolis, Ind., USA)], using a Diax 900 homogenizer (Sigma-Aldrich). After homogenization, samples were rotated at 4° C. for 30 min for complete lysis, the homogenate was centrifuged at 15,000 g for 20 min and the supernatants were used for further analysis. Protein levels were quantified using the BCA assay (Pierce, Rockford, Ill., USA), samples were separated using SDS-polyacrylamide gels and transferred onto nitrocellulose membranes. The membranes were blocked with 5% non-fat milk in TBS-T (Tris-buffered saline with 0.1% TWEEN-20® (Polysorbate 20)) for 1 h, probed using primary antibodies (Table 3) and incubated with appropriate HRP-conjugated secondary antibodies. The bands were visualized by ECL substrate.

TABLE 1

Clinical Information of Control and PD CSF used in FIG. 34

| Group | Age | Sex |
|---|---|---|
| Control (n = 31) | 72 | F |
| | 82 | F |
| | 82 | M |
| | 56 | F |
| | 70 | F |
| | 69 | F |
| | 67 | F |
| | 57 | F |
| | 70 | F |
| | 66 | F |
| | 78 | M |
| | 46 | F |
| | 61 | F |
| | 68 | M |
| | 54 | F |
| | 66 | F |
| | 46 | F |
| | 76 | M |
| | 68 | M |
| | 74 | M |
| | 57 | F |
| | 64 | F |
| | 65 | F |
| | 69 | F |
| | 82 | F |
| | 71 | M |
| | 55 | M |
| | 67 | F |
| | 60 | M |
| | 74 | F |
| | 69 | M |
| PD (n = 80) | 66 | M |
| | 70 | M |
| | 87 | M |
| | 56 | F |
| | 69 | F |
| | 55 | F |
| | 72 | M |
| | 66 | M |
| | 56 | F |
| | 78 | M |
| | 70 | F |
| | 59 | F |
| | 57 | M |
| | 61 | M |
| | 61 | M |
| | 73 | M |
| | 71 | M |
| | 57 | M |
| | 69 | F |
| | 62 | M |
| | 51 | F |
| | 68 | F |
| | 59 | F |
| | 61 | M |
| | 70 | M |
| | 64 | F |

TABLE 1-continued

Clinical Information of Control and PD CSF used in FIG. 34

| Age | Sex |
|---|---|
| 74 | M |
| 63 | M |
| 70 | M |
| 67 | M |
| 67 | M |
| 74 | F |
| 67 | M |
| 57 | M |
| 72 | M |
| 56 | F |
| 77 | F |
| 68 | M |
| 75 | F |
| 67 | M |
| 52 | M |
| 55 | M |
| 75 | M |
| 67 | M |
| 63 | M |
| 65 | F |
| 74 | F |
| 69 | M |
| 76 | M |
| 64 | M |
| 56 | M |
| 60 | F |
| 58 | F |
| 49 | M |
| 49 | M |
| 66 | M |
| 54 | M |
| 74 | F |
| 64 | M |
| 64 | M |
| 68 | M |
| 68 | F |
| 67 | F |
| 68 | M |
| 70 | M |
| 63 | M |
| 64 | M |
| 78 | M |
| 69 | M |
| 58 | F |
| 61 | M |
| 68 | M |
| 79 | M |
| 66 | M |
| 56 | F |
| 66 | M |
| 68 | M |
| 74 | M |
| 75 | M |
| 64 | F |

Summarized information

| Group | Mean age ± s.e.m. | F/M ratio (%) |
|---|---|---|
| Control | 66.9 ± 1.69 | 67.7/32.3 |
| PD | 66.0 ± 0.85 | 31.2/68.8 |

Cell Culture, Transfection, Primary Neuronal Culture and Treatment

SH-SYSY cells (ATCC) were cultured in DMEM containing 10% fetal bovine serum and penicillin/streptomycin at 37° C. under 5% CO2. The cells were transfected using PolyFect reagent (Qiagen) according to the manufacturer's instructions. Primary cortical neurons from WT or PARP1 KO embryos were prepared. Briefly, the primary cortical neurons were cultured at embryonic day 16 in neurobasal media supplemented with B-27, 0.5 mM L-glutamine, penicillin and streptomycin (Invitrogen, Grand Island, NY). The neurons were replaced to fresh medium every 3-4 days. ABT-888 (10 µM), AG-014699 (1 µM), BMN 673 (10 µM), Z-VAD (20 µM), Nec-1 (20 µM) or 3-MA (500 µM) was pretreated to neurons 1 h before α-syn PFF treatment. α-syn PFF were added at 7 days in vitro (DIV) and further incubated for indicated times followed by cell death assay or biochemical experiments. Primary neurons were infected with AAV2-control sgRNA or AAV2-PARP1 sgRNA (ViGene Bioscineces, Rockville, MD, USA), and AAV-α-syn WT or AAV-α-syn A53T at DIV 4-5.

Cell Death Assessment

Primary cultured cortical neurons were treated with α-syn PFF or PAR-α-syn PFF for 14 days. Percent of cell death was determined by staining with 7 µM Hoechst 33342 and 2 µM propidium iodide (PI) (Invitrogen, Carlsbas, CA). Images were taken and counted by Zeiss microscope equipped with automated computer assisted software (Axiovision 4.6, Carl Zeiss, Dublin, CA, USA).

Microfluidic Chambers

Triple compartment microfluidic devices (TCND1000) were obtained from Xona Microfluidic, LLC (Temecula, CA, USA). Glass coverslips were prepared and coated before being affixed to the microfluidic device. Approximately 100,000 WT or PARP1 KO neurons were plated per chamber individually. At 7 DIV, 0.5 mg α-syn PFF were added into chamber 1. To control for direction of flow, a 50 µl difference in media volume was maintained between chamber 1 and chamber 2 and chamber 2 and chamber 3. Neurons were fixed on day 14 after α-syn PFF treatment using 4% paraformaldehyde in PBS. The chambers were then processed for immunofluorescence staining with p-α-syn antibody.

Behavioral Tests

The behavioral deficits in α-syn PFF injected WT or PARP-1 KO mice, α-syn PFF injected mice fed ABT-888, and α-syn PFF or PAR-α-syn PFF injected mice were assessed by the pole test and the grip strength test 1 week prior to sacrifice. All the experiments were performed in a blind fashion.

Pole test. A metal rod (75 cm long with a 9 mm diameter) wrapped with bandage gauze was used as the pole. Before the actual test, the mice were trained for two consecutive days and each training session consisted of three test trials. Mice were placed on 7.5 cm from the top of the pole and the time to turn and total time to reach the base of the pole were recorded. The end of test was defined as placing all 4 paws on the base. The maximum cutoff time to stop the test and recording was 60 s. After each trial, the maze was cleaned with 70% ethanol.

Grip strength test. Neuromuscular function was measured by determining the maximal peak force developed by the mice using an apparatus (Bioseb, USA). Mice were placed onto a metal grid to grasp with either fore or both limbs that are recorded as 'fore limb' and 'fore and hindlimb', respectively. The tail was gently pulled and the force applied to the grid before the mice lose grip was recorded as the peak tension displayed in grams (g).

Dopamine and Derivatives Measurement Using HPLC

Biogenic amine concentrations were measured by high-performance liquid chromatography with electrochemical detection (HPLC-ECD). The striatum was rapidly removed from the brain, weighted and sonicated in ice cold 0.01 mM of perchloric acid containing 0.01% EDTA. The 60 ng of 3,4-dihydroxybenzylamine (DHBA) was used as an internal standard. After centrifugation at 15,000 g for 30 min at 4° C., the supernatant was cleaned using a 0.2 µm filter and 20 µl of supernatant was analyzed in the HPLC column (3 mm×150 mm, C-18 reverse phase column, Acclaim™ Polar Advantage II, Thermo Scientific, USA) by a dual channel coulochem III electrochemical detector (Model 5300, ESA, Inc. Chelmsford, MA, USA). The protein concentrations of tissue homogenates were measured using the BCA protein assay kit (Pierce, Rockford, IL, USA). Data were normalized to protein concentrations and expressed in ng/mg protein.

Immunohistochemistry and Immunofluorescence

Mice were perfused with PBS and 4% PFA and brains were removed, followed by fixation in 4% PFA overnight and transfer to 30% sucrose for cryoprotection. Immunohistochemistry (IHC) and immunofluorescence (IF) was performed on 40 µm thick serial brain sections. Primary antibodies and working dilutions are detailed in Table 2. For histological studies, Free-floating sections were blocked with 10% goat serum in PBS with 0.2% TRITON® X-100 (surfactant) and incubated with TH or p-a-syn antibodies followed by incubation with biotin-conjugated anti-rabbit or mouse antibody, respectively. After three times of washing, ABC reagent (Vector laboratories, CA, USA) was added and the sections were developed using SIGMAFAST™ (DAB peroxidase substrate with metal enhancer) (Sigma-Aldrich). Sections were counterstained with Nissl (0.09% thionin). For the quantification, both TH- and Nissl-positive DA neurons from the SNpc region were counted through optical fractionators, the unbiased method for cell counting, using a computer-assisted image analysis system consisting of an Axiophot photomicroscope (Carl Zeiss) equipped with a computer controlled motorized stage (Ludl Electronics, Hawthorne, N. Y., USA), a Hitachi HV C20 camera, and Stereo Investigator software (MicroBright-Field, Williston, Vt., USA). The total number of TH-stained neurons and Nissl counts were analyzed. For immunofluorescent studies, double-labeled sections with TH and p-a-syn antibodies were incubated with a mixture of ALEXA FLUOR™ 488- and 594-, molecular probes conjugated secondary antibodies (Invitrogen, Carlsbad, Calif., USA). The fluorescent images were acquired by confocal scanning microscopy (LSM710, Carl Zeiss). All the images were processed by the Zen software (Carl Zeiss). The selected area in the signal intensity range of the threshold was measured using ImageJ software.

TABLE 2

Clinical Information of Control and PD CSF used in FIG. 35

| Group | Age | Sex |
|---|---|---|
| Control | 71 | M |
| (n = 33) | 62 | F |
|  | 63 | M |
|  | 63 | F |
|  | 74 | F |
|  | 65 | M |
|  | 62 | M |
|  | 64 | M |
|  | 79 | M |
|  | 66 | M |
|  | 27 | M |
|  | 60 | F |
|  | 55 | M |
|  | 60 | M |
|  | 62 | F |
|  | 60 | F |
|  | 65 | F |
|  | 66 | F |
|  | 27 | M |
|  | 63 | F |
|  | 62 | M |
|  | 62 | F |
|  | 60 | F |
|  | 74 | M |
|  | 61 | M |
|  | 66 | M |
|  | 76 | F |
|  | 65 | F |
|  | 61 | F |
|  | 71 | M |
|  | 71 | F |
|  | 63 | F |
|  | 74 | M |
| PD | 50 | M |
| (n = 21) | 67 | F |
|  | 76 | M |
|  | 57 | F |
|  | 54 | M |
|  | 51 | F |
|  | 56 | F |
|  | 50 | M |
|  | 66 | M |
|  | 53 | M |
|  | 56 | F |
|  | 50 | M |
|  | 43 | M |
|  | 75 | M |
|  | 58 | F |
|  | 69 | M |
|  | 62 | F |
|  | 62 | M |
|  | 85 | M |
|  | 73 | F |
|  | 82 | F |

Summarized information

| Group | Mean age ± s.e.m. | F/M ratio (%) |
|---|---|---|
| Control | 62.76 ± 1.83 | 48.5/51.5 |
| PD | 61.67 ± 2.52 | 42.9/57.1 |

PK Digestion of α-Syn PFF

PK digestion was performed. Ten micrograms of α-syn PFF or PAR-α-syn PFF were mixed with 0.5 to 2.5 µg/ml of PK in PBS and incubated at 37° C. for 30 min. The reaction was stopped by adding 1 mM PMSF, boiled with SDS-sample buffer for 5 min. The bands of the PK digestion products were detected by immunoblotting using epitope-specific α-syn antibodies (Table 3).

TABLE 3

List of Some of the Antibodies Tested in this Study

| Antibody | Source | Identifier | Dilution |
|---|---|---|---|
| PAR | Made in Dawson lab | N/A | 1:2,000 (WB) 1:500 (IF) |
| PARP-1 | BD Bioscience | 611039 | 1:2,000 (WB for human) |
|  | Cell Signaling | 9532 | 1:1,000 (WB for mouse) |
| α-syn | BD Bioscience | 610787 | 1:3,000 (WB) 1:500 (IHC) |
| α-syn (121-125), Syn211 | Sigma | S5566 | 1:3,000 (WB) |
| α-syn (N-term) | LSBio | LS-C352877 | 1:3,000 (WB) |
| α-syn (115-122), LB509 | Abcam | ab27766 | 1:3,000 (WB) |
| α-syn (61-95), 5C2 | Novus | NBP1-04321 | 1:3,000 (WB) |

TABLE 3-continued

List of Some of the Antibodies Tested in this Study

| Antibody | Source | Identifier | Dilution |
|---|---|---|---|
| p-α-syn (Ser129) | Biolegend | 825701 | 1:1,000 (WB) 1:500 (IF) |
| TH | Novus Biologicals | NB300-19 | 1:2,000 (WB) 1:1,000 (IHC, IF) |
| DAT | Sigma | D6944 | 1:1,000 (WB) |
| GAPDH | Abcam | ab8245 | 1:5,000 (WB) |
| β-actin-HRP | Sigma | A3854 | 1:20,000 (WB) |

Human Clinical Trials
Human CSF Samples and PAR ELISA

Participants at the Johns Hopkins University site of the NINDS Parkinson's Disease Biomarker Program (PDBP) underwent extensive clinical and cognitive testing and a lumbar puncture annually. The CSF was centrifuged, aliquoted, and stored at −80° C. within one hour of acquisition. Two different clones (#19 and #25) of monoclonal anti-PAR antibody were used for PAR ELISA. Anti-PAR antibody (capture antibody, clone #19) (5 µg/ml) was coated on 96-well microtiter plate (NUNC™ polystyrene plates, Cat #46051), various concentration of purified PAR (0-200 nM, positive control) and CSF samples from either normal or PD patients were added to each well and incubated for 1 h at room temperature (RT). After washing the plates five times with PBST (0.05% TWEEN-20® (Polysorbate 20) in PBS buffer), the biotinylated PAR antibody (detection antibody, clone #25) was incubated for 1 h at RT. The color change was detected via HRP-conjugated streptavidin antibody (Thermo Scientific). The assay can detect the PAR as low as 3 PM and is saturated at 50 nM.

Clinical Dementia Rating

The Clinical Dementia Rating (CDR) scale is a five-point scale used to assess six different areas of cognitive and functional performance applicable to patients with neurological degeneration and dementia. See Hughes C P, Berg L, Danziger W L, Coben L A, Martin R L, "A New Clinical Scale for the Staging of Dementia," *Br J Psychiatry*, (1982) 140:566-72 which is incorporated by reference for its teaching thereof. The six areas are memory, orientation, judgment & problem solving, community affairs, home & hobbies, and personal care. All patients were assessed using the CDR scale and a personal interview to determine if they had normal cognition, mild cognitive impairment, or dementia.

Student's t-test were used to compare the concentration of PAR between controls and individuals with PD and those with normal cognition and cognitive impairment. A generalized linear model then evaluated the determinants of change in PAR concentration and whether PAR concentration was associated with cognitive changes.

Human Combinatorial Antibody Library

The HuCAL® technology presents an alternative method to the conventional methods of obtaining custom antibodies. Whereas the production of monoclonal antibodies requires immunizing a mouse, rabbit, or goat, and subsequently extracting the B cells from the spleen to recover the antibodies presented, HuCAL® technology allows for faster production time. Through the use of library of complementarity determining regions (CDR), 6 light chain variable regions ($V_L$) and 7 heavy chains ($V_H$), it is possible to generate billions of antibodies in vitro. This is paired with a phage display that incorporates the antibody genes into bacteriophages that presents the antibody on the coating via a disulfide bond, thereby presenting a physical linkage of the phenotype and genotype. Reductive cleavage of the disulfide bond allows for the recovery of the antibodies following a screening, independent of the affinity to the antigen. AbD Serotec was provided with synthetic purified terminally-biotinylated PAR polymer. It was synthesized through reductive amination of pure PAR polymer (2-300 mer). The antibody clones were selected for binding to only polymers and oligomers, and not the ADP-ribose monomer.

The HuCAL® antibody generation process begins with the immobilization of the antigen (PAR) using a covalent coupling to magnetic beads. These are subsequently incubated with the HuCAL® library where nonspecific antibodies are washed out and the specific antibody-phages are eluted. *E. coli* cultures are subjected to infection from the specific antibody-phages to generate an enriched antibody library for the subsequent round of phage screening. The DNA from these enriched antibody-phases is retrieved and subcloned into Fab expression vectors and plated into *E. coli* colonies to produce the Fab fragments. Following this are the colony picking, primary screening, where the colonies were grown in a 384-microtiter plate. Antibody expression is induced and collected after lysing the cultures. These cultures are screened by ELISA with the terminally labelled-PAR antigen. The positive hits from the primary screening are then sequenced to identify the unique antibodies, which are stored for future synthesis for reproducibility. Secondary screening was performed to select out PAR monomer binding antibodies. Finally, expression and purification through affinity chromatography was performed to obtain antibody clones.

Sandwich-ELISA

Anti-PAR antibody (capture antibody, clone #19) (5 µg/ml) was coated on a 96-well microtiter plate (NUNC™ polystyrene plates, Cat #46051). Different concentrations of purified PAR (0-200 nM, positive control) and CSF samples from either normal or PD patients were added to each well, and incubated for 1 hr at room temperature (RT). After washing the plates five times with PBST (0.05% TWEEN-20® (Polysorbate 20) in PBS buffer), the biotinylated PAR antibody (detection antibody, clone #25) was incubated for 1 hr at RT. The color change was detected via HRP-conjugated streptavidin antibody. This assay detects the PAR concentration as low as 3 PM and is saturated at 50 nM.

Results

One hundred ten individuals contributed CSF at baseline (80 PD, 30 control), 94 individuals contributed CSF at the first follow-up (68 PD, 26 controls), 71 individuals contributed CSF at the second follow-up (51 PD, 20 controls), and 36 individuals contributed CSF at the third follow-up (28 PD, 8 controls). At baseline, the average age for both PD and controls was approximately 66 years (p=0.71) and 67% of PD patients were men while 37% of controls were men (p<0.01). Mean PD duration was 6.7 years. There were differences in the mean concentration of PAR between individuals with PD and controls at the first three visits, with a trend toward a difference in the 4th visit (visit 1: PD mean 112.13, control mean 87.99 p=0.04; visit 2: PD mean 145.49, control mean 110.63 p=0.04; visit 3: PD mean 132.29, control mean 86.06 p=0.01; visit 4: PD mean 151.88, control mean 111.07 p=0.08).

| | PAR Concentration (pM) | |
|---|---|---|
| | PD Patients | Healthy Controls |
| Visit 1 | 112.13 | 87.99 |
| Visit 2 | 145.49 | 110.63 |

-continued

| | PAR Concentration (pM) | |
|---|---|---|
| | PD Patients | Healthy Controls |
| Visit 3 | 132.29 | 86.06 |
| Visit 4 | 151.88 | 111.07 |

Figure 3:
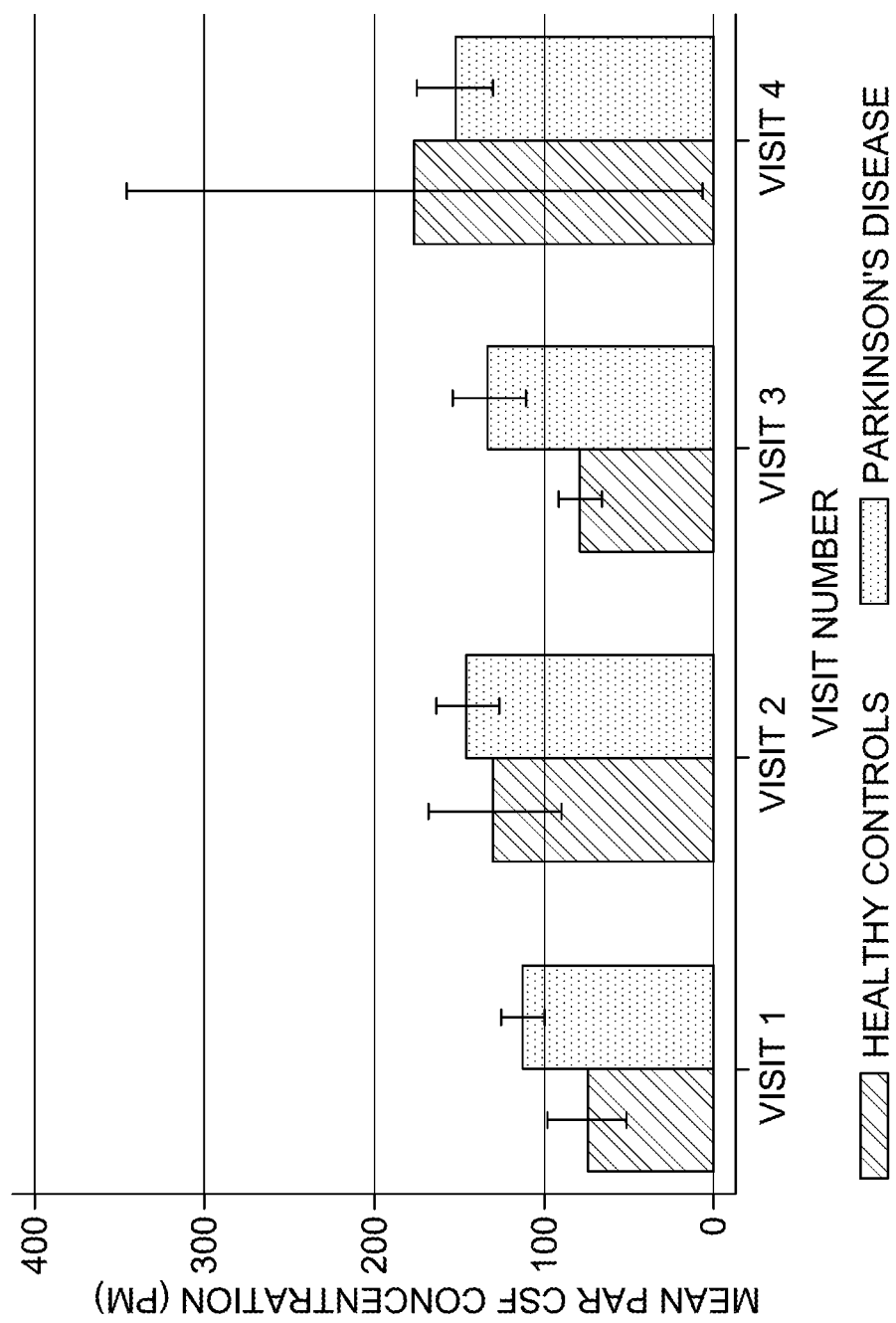
FIG. 3 is a bar graph of the concentration of PAR in the CSF of a PD patient versus healthy controls.
Figure 4:
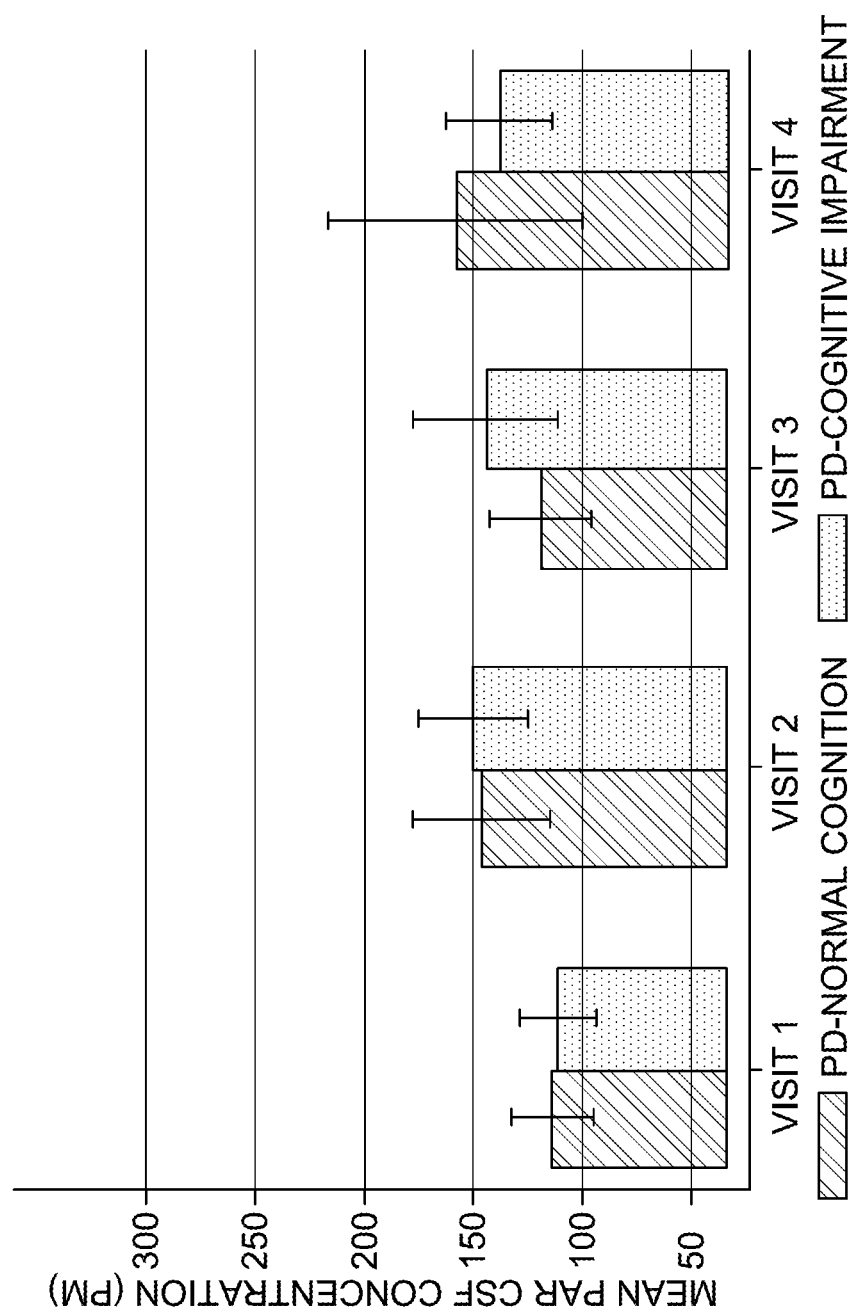
FIG. 4 is a bar graph of the concentration of PAR in PD-normal patients vs PD-cognitively impaired patients.

Disease status was a significant predictors of PAR concentration ($p<0.01$), even after controlling for age, gender, MDS-UPDRS Motor scores, levodopa equivalent dosing, and cognitive impairment (see FIGS. 3 and 4). PAR concentration at visit 2 and visit 4 were significantly different from PAR concentration at visit 1 ($p<0.01$, $p=0.01$) Among only PD participants, PAR concentration ($p=0.03$) and MDS-UPDRS Motor scores ($p<0.01$) were significant predictors of cognitive decline.

Statistical Analysis

All data are represented as mean±s.e.m. with at least 3 independent experiments. Statistical analysis was performed using GraphPad Prism. Differences between 2 means and among multiple means were assessed by unpaired two-tailed student t test and ANOVA followed by Tukey's post hoc test, respectively. Significance was assessed as *$P<0.05$, $P<0.005$, and *$P<0.001$.

In summary, there was a significant difference in the PAR concentration between PD and control patients. There was also a significant difference in the PAR concentration between patients on subsequent sample collection visits.

What is claimed is:

1. A method for monitoring disease progression of a patient with Parkinson's disease (PD) comprising:
   a) measuring a first poly (ADP-ribose) (PAR) concentration in a first sample of cerebrospinal fluid (CSF) from a patient;
   b) administering to the patient a first medical treatment for PD;
   c) subsequent to a) and b), measuring a second PAR concentration in a second sample of CSF from the patient; and
   d) continuing administering the first medical treatment for PD to the patient when the second PAR concentration is the same or lower than the first PAR concentration, or administering a second medical treatment for PD to the patient when the second PAR concentration is higher than the first PAR concentration,
   wherein an increase in PAR concentration in CSF is indicative of disease progression, and
   wherein the first medical and the second medical treatment for PD are selected from the group consisting of surgery, levodopa, dopamine agonists, amantadine, anticholinergics, COMT inhibitors, MAO-B inhibitors and PARP1 inhibitors, thereby monitoring disease progression.

2. The method of claim 1, wherein measuring is by a sandwich ELISA that can detect between about 3 pM and 50 nM PAR.

3. The method of claim 2, wherein the sandwich ELISA comprises at least a capture antibody and a detection antibody, and the capture antibody, the detection antibody or both are anti-PAR monoclonal antibodies.

4. The method of claim 3, wherein the capture antibody is coupled to a solid support.

5. The method of claim 3, wherein the anti-PAR monoclonal antibodies are fully human.

6. The method of claim 3, wherein the detection antibody is conjugated to biotin.

7. The method of claim 1, wherein the sample of cerebrospinal fluid is frozen within one hour of acquisition.

8. The method of claim 1, wherein the first sample of CSF is a control CSF sample collected from the patient at an earlier time period than the second sample of cerebrospinal fluid.

9. The method of claim 8, wherein the control sample was collected at least 1 month prior to the second sample of cerebrospinal fluid from the patient.

10. The method of claim 1, wherein administering the second medical treatment comprises increasing or decreasing a dose of a medicament; increasing or decreasing a frequency of administration of the medicament; eliminating administration of the medicament, administering a different medical treatment from the first medical treatment or a combination thereof.

* * * * *